US012672819B2

(12) United States Patent
Nakae et al.

(10) Patent No.: US 12,672,819 B2
(45) Date of Patent: Jul. 7, 2026

(54) REFERENCE STIMULUS

(71) Applicants: Osaka University, Osaka (JP); PaMeLa, Inc., Osaka (JP)

(72) Inventors: Aya Nakae, Osaka (JP); Koutarou Nomura, Osaka (JP)

(73) Assignees: Osaka University, Osaka (JP); PaMeLa. Inc, Osaka (JP)

( * ) Notice: Subject to any disclaimer, the term of this patent is extended or adjusted under 35 U.S.C. 154(b) by 941 days.

(21) Appl. No.: 17/606,404

(22) PCT Filed: Apr. 24, 2020

(86) PCT No.: PCT/JP2020/017658
§ 371 (c)(1),
(2) Date: Oct. 25, 2021

(87) PCT Pub. No.: WO2020/218493
PCT Pub. Date: Oct. 29, 2020

(65) Prior Publication Data
US 2022/0211324 A1    Jul. 7, 2022

(30) Foreign Application Priority Data

Apr. 26, 2019    (JP) ................................. 2019-085779

(51) Int. Cl.
*A61B 5/00*        (2006.01)
*A61B 5/372*       (2021.01)
(Continued)

(52) U.S. Cl.
CPC ............ *A61B 5/4824* (2013.01); *A61B 5/372* (2021.01); *A61B 5/383* (2021.01); *A61B 5/7246* (2013.01); *G16H 50/50* (2018.01)

(58) Field of Classification Search
CPC ....... A61B 5/4824; A61B 5/372; A61B 5/383; A61B 5/7246; A61B 5/377; G16H 50/50; G16H 50/20; G16H 50/70
See application file for complete search history.

(56) References Cited

U.S. PATENT DOCUMENTS

2016/0015289 A1    1/2016 Simon et al.
2019/0247662 A1*   8/2019 Poltroak ............ A61N 1/36025

FOREIGN PATENT DOCUMENTS

JP        2009018047 A     1/2009
JP        5215508 B1       3/2013
        (Continued)

OTHER PUBLICATIONS

A International Search Report issued in connection with corresponding PCT Application No. PCT/JP2020/017658 on Jul. 21, 2020.
(Continued)

*Primary Examiner* — Tse W Chen
*Assistant Examiner* — Joseph A Tombers
(74) *Attorney, Agent, or Firm* — MUNCY, GEISSLER, OLDS & LOWE, P.C.

(57)        ABSTRACT

Provided is a method for building a model for identifying a reaction of an organism, the method comprising:
    acquiring a reaction data from an organism, including:
        acquiring a first reaction data on the organism being in the first state and stimulation is applied to the organism;
    acquiring a second reaction data on the organism being in the first state and no stimulation is applied to the organism;
    acquiring a third reaction data on the organism being in the second state and stimulation is applied to the organism; and
    acquiring a fourth reaction data on the organism being in the second state and no stimulation is applied to the organism; and (Continued)

building a model unique to the organism for identifying the reaction of the organism, based on the acquired first to fourth reaction data.

5 Claims, 66 Drawing Sheets

(51) Int. Cl.
*A61B 5/383* (2021.01)
*G16H 50/50* (2018.01)

(56) References Cited

FOREIGN PATENT DOCUMENTS

| JP | 6049224 | B2 | 12/2016 |
| JP | 6125670 | B2 | 4/2017 |
| JP | 2017536946 | A | 12/2017 |
| JP | 6371366 | B2 | 7/2018 |
| JP | 6373402 | B2 | 7/2018 |
| JP | 2018166935 | A | 11/2018 |
| JP | 2018187287 | A | 11/2018 |
| JP | 2019032767 | A | 2/2019 |
| WO | WO2017/222997 | A1 | 12/2017 |
| WO | 2019009420 | A1 | 1/2019 |
| WO | 2019022242 | A1 | 1/2019 |

OTHER PUBLICATIONS

Aoki et al., "On the Fluctuations in Electroencephalogram during Pain Sensation", Graduate School of Information Sciences, Tohoku University, Miyagi University of Education, 71-78.

Yoneda et al., "Measurement of Event-related Potentials to Novel Electrical Stimuli with Pain Sensation", Graduate School of Information Sciences, Tohoku University, Miyagi University of Education, 7-12.

* cited by examiner

FIG. 1

Analysis condition (4class)

Time window

- Time window = 15 samples
- Features: 147

(Example of sequence input)

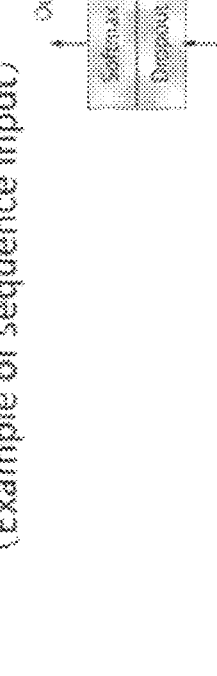

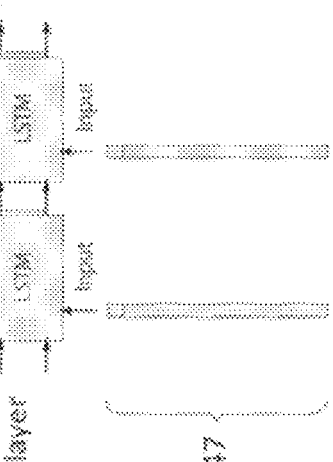

15

147

1 layer

- The following network was used.

layers =
6x1 Layer sequence having the following layers:
1 Sequence input, 15-dimensional sequence input
2 LSTM, LSTM with 300 hidden units
3 Drop-out, 50% drop-out
4 Full binding, 4 full binding layers
5 Softmax, softmax
6 Classification output, crossentropyex Hyper parameter
- Parameter update methodology: Adam
- Learning rate : 0.001
- Mini batch size : 128
- Epoch count: 20
- L2 regularization (λ) : 0.01
- Drop-out : 0.5

Raw data (actual performance)

(1)artifact1

※There was deficiency in noise task data collection, and use for model creation was not possible Close eyes tightly Off-line chronological data analysis
(actual performance)

(1)artifact1

[Noise test, open eyes]

→In 4-class, it should be determined as no pain with noise (2), but an error of differentiation is observed.

Raw data (for model creation)

(2)artifact2

Close eyes tightly　　Stretch body　　Read out loud

Off-line chronological data analysis
(for model creation)

(2)artifact2

[Noise test, open eyes]

→In 4-class, it should be determined as no pain with noise (2),
but since it is for model creation, correct determination is carried out.

Raw data (actual performance) (3)artifact_pain1

Fp1

Fp2

Trigger

Thermal stimulation

Having pain + noise task

Off-line chronological data analysis (actual performance)

(3)artifact_pain1

[Noise test upon pain stimulation, open eyes]

→In 4-class, no pain with noise (2) and having pain with noise (3) alternately appear, and thus determination is carried out successfully.

Off-line chronological data analysis
(for model creation)

(4)artifact_pain2

[Noise test upon pain stimulation, open eyes]

→In 4-class, no pain with noise (2) and having pain with noise (3)
alternately appear, and thus determination is carried out successfully.

Off-line chronological data analysis
(for model creation)

(5)ref

[Pain stimulation, rest, closed eyes]

→In 4-class, since having noise with no noise (1) appears upon
pain stimulation, a model is successfully created.

Off-line chronological data analysis (actual performance)

(6)main1

[Pain stimulation, rest, closed eyes]

→In 4-class, since having noise with no noise (1) appears upon pain stimulation, differentiation is carried out successfully.

Raw data (actual performance)     (7)main2

Off-line chronological data analysis
(actual performance)

(7)main2

[Pain stimulation, rest, closed eyes]

→Where there is no pain stimulation in the latter half, with noise
(2 or 3) is determined, where there are more errors in differentiation.

Off-line chronological data analysis
(actual performance)
[Noise test upon pain stimulation, closed eyes]

(8)main3

→Overall, it is determined as having noise (2 or 3),
where there are more differentiation errors in 2-class.

Off-line chronological data analysis
(actual performance)

(9)2temp

[Pain stimulation, open eyes]

→Overall, it is determined as having noise (2), wherein there are more errors in differentiation. It is considered that this is because a closed-eye task had not been carried out.

FIG. 21
Off-line chronological data analysis     (10)2temp_artifact
(actual performance)
[Noise test upon pain stimulation (46°C and 48°C), open eyes]
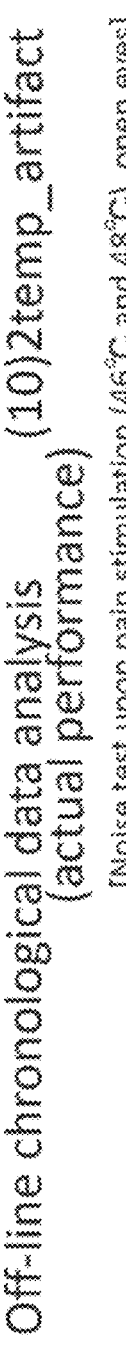
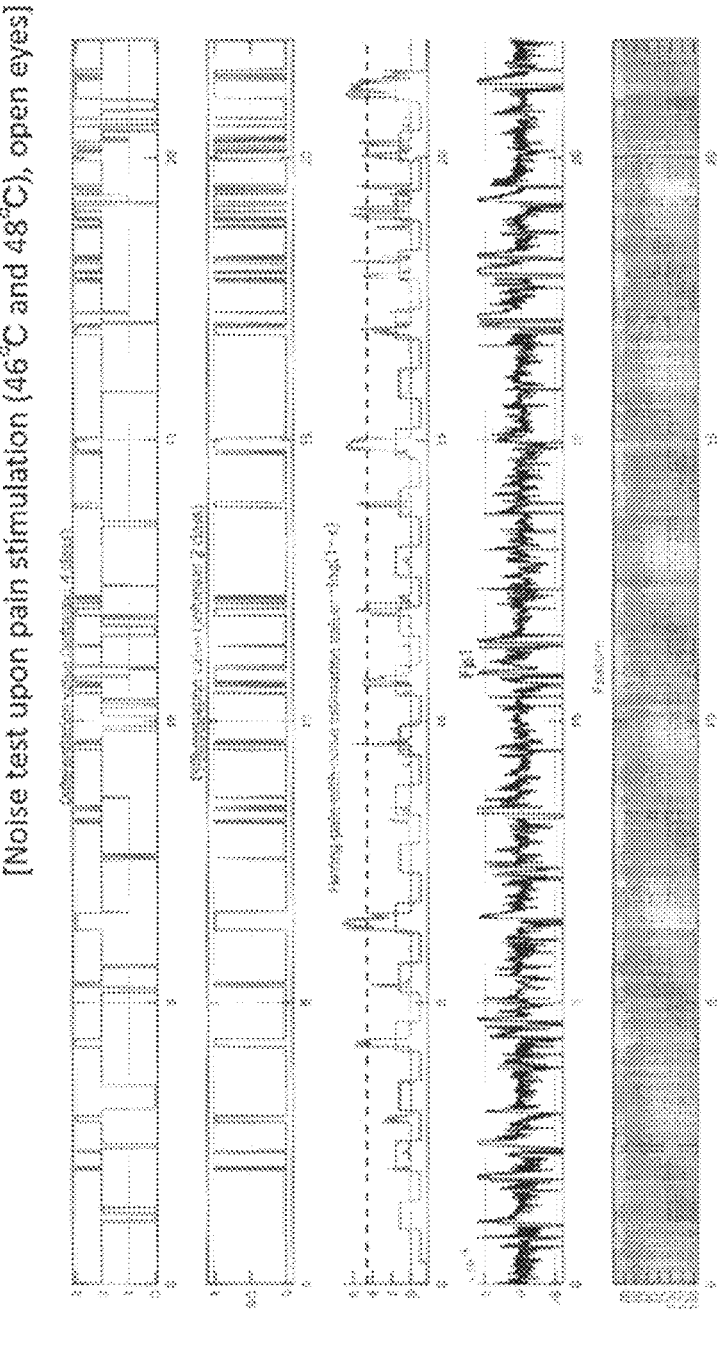
→Although closed-eye task is not carried out, there is slight improvement in differentiation precision, which may be due to the practice of the task of reacting to pain upon pain stimulation.

FIG. 22

| | True Result | |
|---|---|---|
| | Positive | Negative |
| Prediction Result — Positive | TP | FP |
| Prediction Result — Negative | FN | TN |

(Differentiation Accuracy) Accuracy=(TP+TN)/(TP+FP+TN+FN)

(Precision) Precision=TP/(TP+FP)

(Recall) Recall=TP/(TP+FN)

(F1 Value) F1-score=2*Recall*Precision/(Recall+Precision)

FIG. 23 Differentiation Accuracy

| ID | accuracy | 2class | 4class |
|---|---|---|---|
| 1 | 0119_Osaka038_artifact_pain1 | 79.8 | 75.8 |
| 2 | 0119_Osaka038_artifact_pain2 | 70.9 | 81.7 |
| 3 | 0119_Osaka038_ref | 84.1 | 83.5 |
| 4 | 0119_Osaka038_main1 | 80.1 | 80.2 |
| 5 | 0119_Osaka038_main2 | 68.7 | 78.0 |
| 6 | 0119_Osaka038_main3 | 52.8 | 69.8 |
| 7 | 0119_Osaka038_2temp | 61.3 | 67.3 |
| 8 | 0119_Osaka038_2temp_artifact | 66.9 | 64.8 |
| | mean | 69.3 | 73.9 |

Comparison of differentiation accuracy (accuracy) between 4 classes and 2 classes

Precision

| ID | precision | 2class | 4class |
|---|---|---|---|
| 1 | 0119_Osaka038_artifact_pain1 | 76.8 | 80.3 |
| 2 | 0119_Osaka038_artifact_pain2 | 70.3 | 83.1 |
| 3 | 0119_Osaka038_ref | 63.5 | 62.7 |
| 4 | 0119_Osaka038_main1 | 81.5 | 83.3 |
| 5 | 0119_Osaka038_main2 | 45.5 | 56.7 |
| 6 | 0119_Osaka038_main3 | 36.2 | 46.7 |
| 7 | 0119_Osaka038_2temp | 44.9 | 75.9 |
| 8 | 0119_Osaka038_2temp_artifact | 64.9 | 87.8 |
| | mean | 60.4 | 72.1 |

Comparison of precision (precision) between 4 classes and 2 classes

Recall

| ID | recall | 2class | 4class |
|----|--------|--------|--------|
| 1 | 0119_Osaka038_artifact_pain1 | 95.3 | 79.2 |
| 2 | 0119_Osaka038_artifact_pain2 | 92.2 | 88.5 |
| 3 | 0119_Osaka038_ref | 99.7 | 99.4 |
| 4 | 0119_Osaka038_main1 | 39.0 | 38.1 |
| 5 | 0119_Osaka038_main2 | 85.7 | 76.2 |
| 6 | 0119_Osaka038_main3 | 92.4 | 66.2 |
| 7 | 0119_Osaka038_2temp | 32.4 | 8.5 |
| 8 | 0119_Osaka038_2temp_artifact | 62.4 | 28.1 |
| | mean | 74.9 | 60.5 |

Comparison of recall (recall) between 4 classes and 2 classes

■ 2class  ▩ 4class

F1 Value

| ID | F1-score | 2class | 4class |
|---|---|---|---|
| 1 | 0119_Osaka038_artifact_pain1 | 85.0 | 79.7 |
| 2 | 0119_Osaka038_artifact_pain2 | 79.8 | 85.7 |
| 3 | 0119_Osaka038_ref | 77.6 | 76.9 |
| 4 | 0119_Osaka038_main1 | 62.8 | 52.3 |
| 5 | 0119_Osaka038_main2 | 59.5 | 65.0 |
| 6 | 0119_Osaka038_main3 | 52.0 | 54.8 |
| 7 | 0119_Osaka038_2temp | 37.6 | 15.3 |
| 8 | 0119_Osaka038_2temp_artifact | 63.6 | 42.6 |
| | mean | 63.5 | 59.0 |

Comparison of F1 value (F1-score) between 4 classes and 2 classes

Mean Value of Evaluation Standards

| mean | 2class | 4class |
|---|---|---|
| accuracy | 69.3 | 73.9 |
| precision | 60.4 | 72.1 |
| recall | 74.9 | 60.5 |
| F1-score | 63.5 | 59.0 |

Comparison of mean value of evaluation standards between 4 classes and 2 classes Flow of 2 class LSTM analysis (prior art)

(A) For model creation
(5)ref (B) Actual performance (Test)

(Learning)

Model (5)ref

Reference
• Mean Value
• Standard Deviation (Label)
No pain
Having pain (1) artifact1
(2) artifact2
(3) artifact_pain1
(4) artifact_pain2
(6) main1
(7) main2
(8) main3
(9) 2temp
(10) 2temp_artifact Raw data (actual performance)        (1)artifact1

:X: There was deficiency in noise task data collection, and
use for model creation was not possible Close eyes tightly FIG. 32
Raw data (actual performance)
(2)artifact2
{noise test, open eyes}
→ It should have been determined as (0) no pain since the classes were 2 classes; however, mis-differentiation, having pain, was made.

off-line chronological data analysis (actual performance) (3)artifact_pain1

[Noise test upon pain stimulation, open eyes]

→ In 2 classes, (0) no pain and (1) having pain appeared alternately; thus, the differentiation was made well.

off-line chronological data analysis (actual performance)     (4)artifact_pain2

[Noise test upon pain stimulation, open eyes]

differentiation value (softmax: 2 classes)

having-pain estimation value :−log(1−x)

features

→ In 2 classes, (0) no pain and (1) with noise appeared alternately;
thus, the differentiation was made well.

Raw data (for model creation)

(5)ref

Fp1

Fp2

Clean reference section

No pain        Having pain        No pain

Trigger

Thermal stimulation

Off-line chronological data analysis (for model creation)     (5)ref

[Pain stimulation, rest, eyes closed]

In 2 classes, (1) having pain appeared when there was a pain stimulation; thus, the model was created well.

off-line chronological data analysis (actual performance)   (6)main1

[Pain stimulation, rest, eyes closed]

→ In 2 classes, (1) having pain appeared when there was a pain stimulation; thus, the differentiation was made well.

Off-line chronological data analysis (actual performance)    (7)main2

[Pain stimulation, rest, eyes closed]

⇒ Where there was no pain stimulation in the second half, it was determined as with noise (1), and the number of mis-differentiation increased.

FIG. 44
Off-line chronological data analysis (actual performance)     (8)main3
[Noise test upon pain stimulation, eyes closed]
→ Overall, it was determined as having pain (1), and the number of mis-differentiation increased in 2 classes.

Off-line chronological data analysis (actual performance)

(9)2temp

[Pain stimulation, open eyes]

differentiation value (softmax: 2 classes)

having-pain estimation value −log(1−x)

features

→ Overall, the number of mis-differentiation increased. It is conceivable that this was because no eye-closing task was performed.

FIG. 49

Mounting Locations of Brain-Wave Electrodes

※ Odd numbers represent left and
even numbers represent right

Z: brow (middle of forehead)

A1, A2: earlobe

F7, F8: over glabellar eyebrows
C3, C4: temple at eyebrow edge
T5, T6: behind the ears

| | | | |
|---|---|---|---|
| Ch1 | Fp1 | | |
| Ch2 | Fp2 | | |
| Ch3 | F7 | | |
| Ch4 | F8 | | |
| Ch5 | C3 | | |
| Ch6 | C4 | | |
| Ch7 | T5 | | |
| Ch8 | T6 | | |

* This time, only 6 channels
were used for the analysis

Model search: create 19 types of standardization parameters
and 10 models (regression) corresponding thereto Model search: create 10 types of standardization parameters and 10 models (regression) corresponding thereto

REFERENCE STIMULUS

TECHNICAL FIELD

The present disclosure relates to signal processing using a reference stimulation. More specifically, the resent disclosure relates to techniques that use reference stimulations in the processing of physiological signals. Still more specifically, the present disclosure relates to the use of reference stimulations for brainwaves.

BACKGROUND ART

There is a machine called Pain Vision. This is epoch-making in that the machine quantifies the pain, here the degree of the pain is quantified based on the data notified by pressing a button.

There exists a technique for measuring brain activity in response to a stimulation using brainwaves, call d an evoked potential. It has already been clarified that pain can be measured, and it is known that large brain activity occurs in response to a large stimulation. This research has been preceded overseas. However, it is considered as a means of finding neuropathy, and has not yet reached the point of measuring the magnitude of pain itself.

CITATION LIST

Patent Literature

[PTL 1] Japanese Patent No. 6373402
[PTL 2] Japanese Patent No. 6371366
[PTL 3] Japanese Patent No. 5909748
[PTL 4] Japanese Patent No. 6049224
[PTL 5] Japanese Patent No. 5215508
[PTL 6] Japanese Patent No. 6125670
[PTL 7] Japanese Laid-Open Publication No. 2018-166935
[PTL 8] Japanese National Phase PCT Laid-open Publication No. 2017-536946
[PTL 9] Japanese Laid-Open Publication No. 2018-187287
[PTL 10] Japanese Laid-Open Publication No. 2019-32767
[PTL 11] Japanese Laid-Open Publication No. 2009-18047

SUMMARY OF INVENTION

Technical Problem

The present disclosure has been completed by finding an unexpected improvement in analytical accuracy using a method of [1] stimulating an object in advance, [2] then measuring signals such as brainwaves, [3] performing fitting, and [4] determining some state of the object. In particular, the present disclosure has found unexpected improvement on analysis accuracy using a method of [1] stimulating an object in advance, [2] then measuring signals such as brainwaves, [3] creating a (differentiation) model for an individual, [4] performing fitting, and [5] determining some state of the object using the created model.

In particular, the present disclosure is for conducting an actual diagnosis based on the data acquired b giving a reference stimulation (data acquired in advance), and particular attention is paid to noise processing. One of the features of the present disclosure is that if the purpose of the prior art is to achieve a 70% accuracy rate, the 30% noise can be improved by as much as 20%. The approach of the present disclosure provides a method of performing noise generation behavior (for example, meaningless behavior), acquiring data with noise, labeling the acquired data in four divisions (with or without noise, having pain or no pain), and machine-learning each to create a discriminant, fitting the actually-acquired signal to the discriminant to determine the presence or absence of pain.

Examples of embodiments of the present disclosure include the following:

(Item 1)

A method for building a model for identifying a reaction of an organism, the method comprising:

acquiring a plurality of reaction data from an organism, including:

acquiring a first reaction data on the organism being in a first state; and acquiring a second reaction data on the organism being in a second state; and building a model unique to the organism for identifying the reaction of the organism, based on the plurality of acquired reaction data.

(Item 2)

The method of item 1, wherein the first reaction data is data on the organism being in the first state and stimulation is applied to the organism, and wherein the second reaction data is data on the organism being in the second state and stimulation is applied to the organism.

(Item 3)

The method of item 2, wherein the acquiring the plurality of reaction data from the organism includes:

acquiring a third reaction data on the organism being in the first state and no stimulation is applied to the organism; and acquiring a fourth reaction data on the organism being in the second state and no stimulation is applied to the organism.

(Item 4)

The method of any one of items 1-3, wherein the reaction of the organism includes a reaction with pain and a reaction with no pain.

(Item 5)

The method of any one of items 1-4, wherein the first state is a state in which noise is added to the reaction data, and wherein the second state is a state in which no noise is added to the reaction data.

(Item 6)

The method of item 5, wherein the second state includes a state in which the organism is performing a visual deprivation behavior, a hearing deprivation behavior, or a combination thereof.

(Item 7)

The method of any one of items 1-6, wherein the building the model includes: updating an existing model for identifying a reaction of an organism, based on the plurality of acquired reaction data, to build a model unique to the organism.

(Item 8)

The method of any one of items 1-6, wherein the building the model includes: selecting a model unique to an organism from a plurality of existing models for identifying the reaction of the organism, based on the plurality of acquired reaction data, to build a model unique to the organism.

(Item 9)

The method of any one of items 1-8, wherein the reaction of the organism includes a reaction with pain an a reaction with no pain, and wherein the building the model includes:

a) the step of performing a pain test on a plurality of subjects to acquire a plurality of COVAS data;

b) the step of averaging the plurality of OVAS data to create a COVAS template;

c) the step of performing the pain test on the organism to acquire brainwaves data or analysis data thereof from the organism;

d) the step of cutting out the brainwaves data or analysis date thereof based on the COVAS template; and e) the step of learning the cut out brainwaves data or analysis data thereof as data for learning and a value of a COVAS template corresponding to the cut out brainwaves data or analysis data thereof as a label to create a model.

(Item 10)

A system comprising:

a model built by a method of any one of items 1-9;

an acquisition means of acquiring a reaction data from an organism; and an output means of outputting a result of the model identifying the reaction of the organism based on the reaction data acquired by the acquisition means.

(Item 11)

A system comprising:

an acquisition means of acquiring a reaction data from an organism, the acquisition means including a referencing mode and a measuring mode;

a model building means of building a model using the reaction data acquired from the acquisition means as a reference stimulation, wherein the model is built by building a model unique to the organism for identifying the reaction of the organism, based on a plurality of reaction data acquired by:

acquiring a plurality of reaction data from the organism in the referencing mode, including:

acquiring a first reaction data on the organism being in a first state; and acquiring a second reaction data on the organism being in a second state; and an output means of outputting a result of the model identifying the reaction of the organism based on the reaction data acquired by the acquisition means in the measuring mode.

(Item 12)

The system of item 11, further comprising a standard model, wherein the model building means corrects the standard model based on the plurality of reaction data.

(Item 13)

A program for building a model for identifying a reaction of an organism, the program being executed by a computer system equipped with a processor, wherein the program causes the processor to execute processing that includes: building a model unique to the organism for identifying the reaction of the organism, based on a first reaction data on the organism being in a first state and a second reaction data on the organism being in a second state.

The present disclosure is intended so that one or more of the aforementioned characteristics can be provided not only as the explicitly disclosed combinations, but also as other combinations thereof. Additional embodiments and advantages of the present disclosure are recognized by those skilled in the art by reading and understanding the following detailed description as needed.

Advantageous Effects of Invention

Pain sensitivity is completely different among the elderly and the young, and there is no absolute standard, which makes it impossible to conduct accurate diagnosis. Under such circumstances, the present disclosure has the effect that pain can be standardized for each individual by giving a reference stimulation to each object and collecting data. In addition, every patient has noise (especially electromyogram), and the noise cannot be removed, which makes it impossible to conduct accurate diagnosis. As an improved invention, the present disclosure also provides capability to conduct accurate testing even in the presence of noise.

BRIEF DESCRIPTION OF DRAWINGS

FIG. 1 shows the analysis condition for 4 class LSTM analysis.

FIG. 21 shows results of performing an off-line chronological data analysis on the raw data shown in FIG. 20. Although no eye-closing task was performed, a task to respond to pain was performed during pain stimulation. Thus, the differentiation accuracy was improved a little.

FIG. 22 shows evaluation standards in a comparison of LSTM between 4 classes and 2 classes.

FIG. 32 shows results of performing an off-line chronological data analysis on the raw data shown in FIG. 31. It should have been determined as (0) no pain since the classes were 2 classes; however, mis-differentiation, having pain, was made.

FIG. 44 shows results of performing an off-line chronological data analysis on the raw data shown in FIG. 43. Overall, it was determined as having pain (1), aid the number of mis-differentiation increased in 2 classes.

FIG. 49 is a schematic diagram of a stand-alone type system.

DESCRIPTION OF EMBODIMENTS

Figure 2:
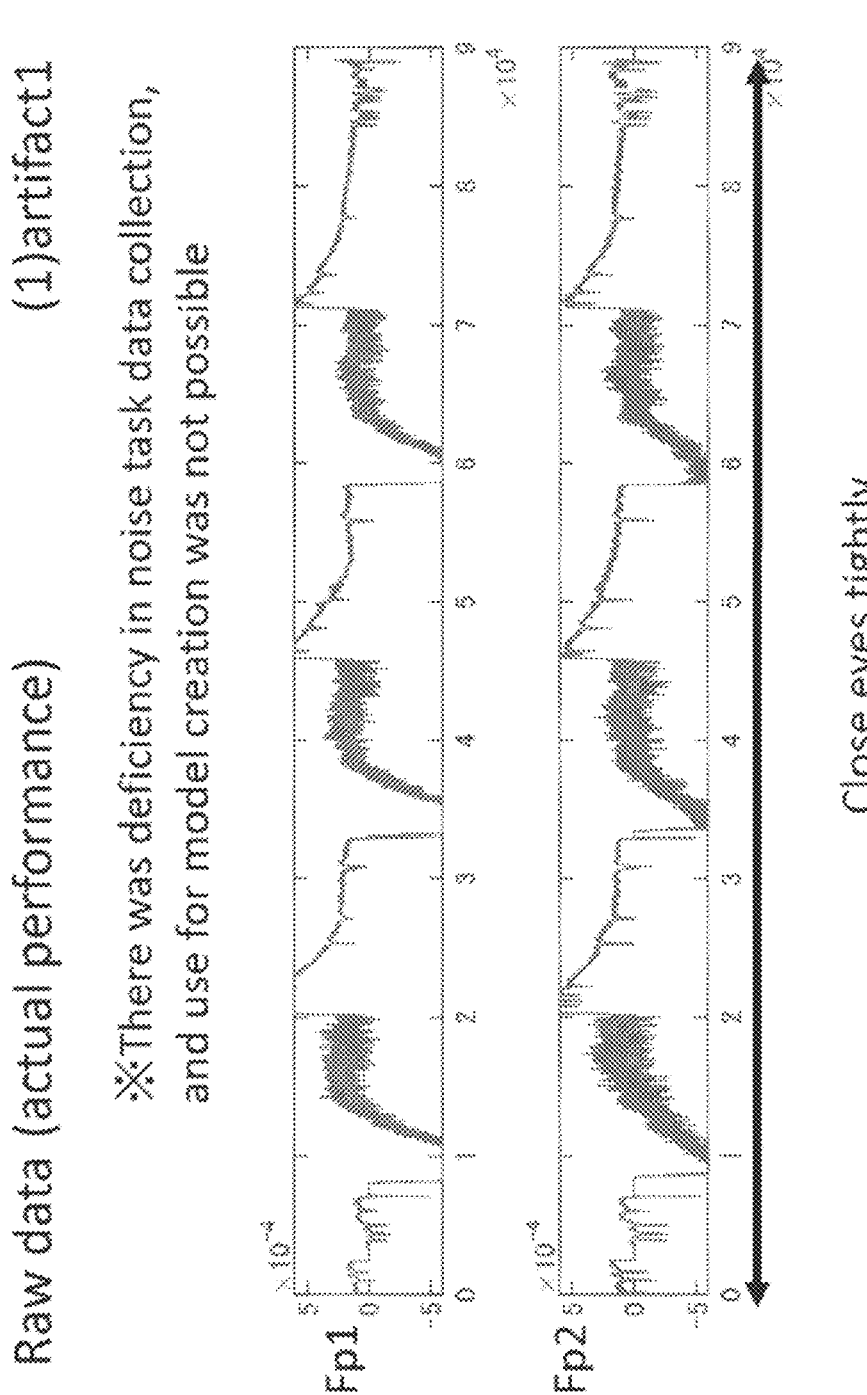
FIG. 2 shows raw data (artifact1) used for class LSTM analysis. The conditions for artifact1 are noise test (tightly closing the eyes, stretching the body, reading out loud), eyes opened. Due to a defect in the data collection of the noise task, model creation based on this data is not performed.

The present disclosure will be described hereinafter with reference to the best mode. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present disclosure pertains. In case of a contradiction, the present specification (including the definitions) takes precedence.

Definition, Etc

The definitions and/or basic technical contents of terms particularly used in the present specification will be described below as appropriate.

As used herein, "reference stimulation" refers to a stimulation given before an actual test, analysis or diagnosis is performed when a test, analysis or diagnosis is performed based on a certain stimulation. In the present specification, it may be abbreviated as "Ref stimulation" or the like. The reference stimulation may be of any magnitude and is, for example, often smaller than the stimulation given at the time of diagnosis.

As used herein, "reaction of an organism" refers to any phenomenon that occurs in response to a stimulation given to an organism. Examples of the reaction of the organism include sensations that can be recognized by the organism, such as pain, taste, sight, smell, and hearing.

As used herein, "model" or "hypothesis" are used synonymously, which is expressed using mapping describing the relationship of inputted prediction targets to prediction results, or a mathematical function or Boolean expression of a candidate set thereof. For learning with machine learning, a model considered the best approximation of the true model is selected from a model set by referring to training data.

Examples of models include generation model, identification model, function model, and the like. Models show a difference in the direction of classification model expression of the mapping relationship between the input (object being predicted) x and output (result of prediction) y. A generation model expresses a conditional distribution of output y given input x. An identification model expresses a joint distribution of input x and output y. The papping relationship is probabilistic for an identification model and a generation model. A function model has a definitive mapping relationship, expressing a definitive functional relationship between input x and output y. While identification is sometimes considered slightly more accurate in a identification model and a generation model, the e is basically no difference in view of the no free lunch theorem.

As used herein, "machine learning" refers to a technology for imparting a computer the ability to learn without explicit programming. This is a process of improving a faction unit's own performance by acquiring new knowledge/skill or reconfiguring existing knowledge/skill. Most of the effort required for programming details can be reduced by programming a computer to learn from experience. In the machine learning field, a method of constructing a computer program that enables automatic improvement from experience has been discussed. Data analysis/machine learning plays a role in elemental technology that is the foundation of intelligent processing along with field of the algorithms. Generally, data analysis/machine learning is utilized in conjunction with other technologies, thus requiring the knowledge in the cooperating field (domain specific knowledge; e.g., medical field). The range of application thereof includes roles such as prediction (collect data and predict what would happen in the future), search (find a notable feature from the collected data), and testing/describing (find relationship of various elements in the data). Machine learning is based on an indicator indicating the degree of achievement of a goal in the real world. The user of machine learning must understand the goal in the real world. An indicator that improves when an objective is achieved needs to be formularized. Machine learning has the opposite problem that is an ill-posed problem for which it is unclear whether a solution is found. The behavior of the learned rule is not definitive, but is stochastic (probabilistic). Machine learning requires an innovative operation with the premise that some type of uncontrollable element would remain. The tailor-made method of the invention can be considered as a solution to such a problem. It is useful for a user of machine learning to sequentially select data or information in accordance with the real world goal while observing performance indicators during training and operation.

Linear regression, logistic regression, support vector machine, or the like can be used for machine learning, and cross validation (CV) can be performed to calculate differentiation accuracy of each model. After ranking, a feature can be increased one at a time for machine learning (linear regression, logistic regression, support vector machine, or the like) and cross validation to calculate differentiation accuracy of each model. A model with the highest accuracy can be selected thereby. Any machine learning can be used herein. Linear, logistic, support vector machine (SVM), or the like can be used as supervised machine learning.

Machine learning uses logical reasoning. There are roughly three types of logical reasoning, i.e., deduction, induction, and abduction as well as analogy. Deduction, under the hypothesis that Socrates is a human and all humans die, reaches a conclusion that Socrates would die, which is a special conclusion. Induction, under the hypothesis that Socrates would die and Socrates is a human, reaches a conclusion that all humans would die, and determines a general rule. Abduction, under a hypothesis that Socrates would die and all humans die, arrives at Socrates is a human, which falls under a hypothesis/explanation. However, it should be noted that how induction generalizes is dependent on the premise, so that this may not be objective. Analogy is a probabilistic logical reasoning method which reasons that if object A has 4 features and object B has three of the same features, object B also has the remaining one feature so that object A and object B are the same or similar and close.

Feature/attribute in machine learning represents the state of an object being predicted when viewed from a certain aspect. A feature vector/attribute vector combines features (attributes) describing an object being predicted in a vector form.

As used herein, "reaction data" refers to data on a phenomenon that occurs in response to a stimulation to an object. When the object is an organism, it refer to data showing the physiological activity of the objective organism, for example, pain sensation. The reaction data includes, for example, brainwave data.

As used herein, "stimulation" refers to anything that causes some type of a reaction to an object. If the object is an organism, stimulation refers to a factor resulting in a temporarily change in the physiological activity of the organism or a portion thereof.

As used herein, "state" refers to the condition of an object, which changes in response to internal or external stimulations.

As used herein, "behavior" refers to any movement of an object, either active or passive. The active movements include, for example, closing the eyes, and passive movements include, for example, being put on headphones.

As used herein, "visual deprivation" refers to blocking the vision of an object or preventing changes in brainwaves derived from the vision of the object, by any means. Visual deprivation behaviors include, for example, closing the eyes, covering the eyes with a substance that does not allow light to pass through, and being in a space that does not allow light to pass through.

As used herein, "hearing deprivation" refers to blocking the hearing of an object or preventing changes in brainwaves derived from the hearing of the object, by any means. Hearing deprivation behaviors include, for example, wearing earplugs, wearing headphones to hear white noise, and being in a space where the sound is blocked.

(Brainwave Related Matters)

As used herein, "object" is used synonymously with patient and subject and refers to any organism or animal which is subjected to the technology in the disclosure such as pain measurement and brainwave measurement. An object is preferably, but is not limited to, humans. As used herein, an object may be referred to an "object being estimated" when estimating pain, but this has the same meaning as object or the like. There may be a plurality of "objects". In such a case, each individual may be referred to as a "sample" (of objects).

As used herein, "brainwaves" has the meaning that is commonly used in the art and refers to a current generated by a difference in potential due to neurological activity of the brain when a pair of electrodes is placed on the scalp. Brainwaves encompass electroencephalogram (EEG), which is acquired from deriving and recording temporal changes in the current. A wave with an amplitude of about $50\,\mu V$ and a frequency of approximately 10 Hz is considered the primary component at rest. This is referred to as an a wave. During mental activity, a waves are suppressed and a fa t wave with a small amplitude of 17 to 30 Hz appears, which is referred to as a p wave. During a period of shallow sleep, a waves gradually decrease and θ waves of 4 to 8 Hz appear. During a deep sleep, δ waves of 1 to 4 Hz appear. These brainwaves can be expressed by a specific amplitude, frequency, complexity index, correlation, or the like. Brainwaves can be represented by a specific, amplitude and frequency or analysis of amplitude in the present disclosure.

As used herein, "brainwaves data" is any data related to brainwaves (also referred to as "amount of brain activity", "brain feature", or the like), such as amplitude data (EEG amplitude), frequency property, or the like. "Analysis data" from analyzing such brainwaves data can be used in the same manner as brainwaves data, so that such data is collectively referred to as "brainwaves data or analysis data thereof" herein. Examples of analysis data include mean amplitude and peak amplitude (e.g., Fz, Cz, C3, C4), frequency power (e.g., $Fz(\delta)$, $Fz(\theta)$, $Fz(\alpha)$, $Fz(\beta)$, $Fz(\gamma)$, $Cz(\beta)$, $Cz(\theta)$, $Cz(\alpha)$, $Cz(\beta)$, $Cz(\gamma)$, $C3(\delta)$, $C3(\theta)$, $C3(\alpha)$, $C3(\beta)$, $C3(\gamma)$, $C4(\delta)$, $C4(\theta)$, $C4(\alpha c)$, $C4(\beta)$, and $C4(\gamma)$) and the like of brainwaves data. Of course, this does not exclude other data commonly used as brainwaves data or analysis data thereof. For example, raw data sampled out for a certain period of time, when used for differentiation, is also a feature, so this can also be used in the present disclosure.

As used herein, "brainwave feature" or "feature of brainwaves" refers to any feature of brainwaves, encompassing "brainwaves data or analysis data thereof" such as amplitude, interrelation of brainwave features, frequency power, and complexity index. As examples thereof, the amplitude can comprise an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features can comprise potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power can comprise a spectral density, a power spectrum, or a subtype thereof, and the complexity index can comprise at least one selected from entropy (e.g.; multiscale entropy (MSE), sample entropy, self-entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

As used herein, "amplitude data" is one type of "brainwaves data" and refers to data for amplitudes of brainwaves. This is also referred to as simply "amplitude" or "EEG amplitude". Since such amplitude data is an indicator of brain activity, such data can also be referred to as "brain activity data", "amount of brain activity", or the like. Amplitude data can be acquired by measuring electrical signals of brainwaves and is indicated by potential (can be indicated by μV or the like). Amplitude data that can be used include, but are not limited to, mean amplitude.

As used herein, "pain" refers to a sensation that is generated as stimulation, generally upon intense injury such as damage/inflammation to a body part. Pain is not a disease but is a symptom. The state thereof is determined by the combination of three main properties, i.e., central nervous, nociceptive, and neuropathic pain. Acute pain and chronic pain are distinguished, which are different in terms of the associated cerebral site network (connectivity). Chronic pain is sometimes subjectively reported as painful when in fact it is not painful. Chronic pain includes psychogenic factors that cannot be explained by sensational intensity of pain stimulation.

In humans, common sensations are also included as sensations accompanied by strong unpleasant feelings, such as pain. In addition, cutaneous pain and the like also has an aspect as an external receptor to a certain degree, which plays a role in determining the quality such as hardness, sharpness, hotness (thermal pain), coldness (cold pain), or spiciness of an external object in cooperation with other skin sensation or taste. The sensation of pain of humans can occur at almost any part of the body (e.g., pleura, peritoneum, internal organs (visceral pain, excluding the brain), teeth, eyes, ears, and the like) other than the skin and mucous membrane, which can all be sensed as brainwaves or a change thereof in the brain. Additionally, internal sensation of pain represented by visceral pain is also encompassed by sensation of pain. The aforementioned sensation of pain is referred to as somatic pain relative to visceral pain. In addition to somatic pain and visceral pain, sensation of pai called "referred pain", which is a phenomenon where pai is perceived at a surface of a site that is different from a site that is actually damaged, is also reported. The present disclosure can accurately diagnose and analyze the temporal changes of these various pain types, by applying a reference stimulation.

For sensation of pain, there are individual differences in sensitivity (pain threshold), as well as qualitative difference due to a difference in the receptor site or how a pain stimulation occurs. Sensation of pain is classified into dull pain, sharp pain, and the like, but sensation of pain of any type can be measured, estimated, and classified in this disclosure. The disclosure is also compatible with fast sensation of pain (A sensation of pain), slow sensation of pain (B sensation of pain), (fast) topical pain, and (slow) diffuse pain. The present disclosure is also compatible with abnormality in sensation of pain such as hyperalgesia. Two nerve fibers, i.e., "Aδ fiber" and "C fiber", are known as peripheral nerves that transmit pain. For example, when a hand is hit, the initial pain is transmitted as sharp pain from a clear origin (primary pain: sharp pain) by conduction through the Aδ fiber. Pain is then conducted through the C fiber to feel throbbing pain (secondary pain; dull pain) with an unclear origin. Pain is classified into "acute pain" lasting 4 to 6 weeks or less and "chronic pain" lasting 4 to 6 weeks or more. Pain is an important vital sign along with pulse, body temperature, blood pressure, and breathing, but is difficult to express as objective data. Representative pai scales VAS (visual analogue scale) and faces pain rating scale are subjective evaluation methods that cannot compare pain between patients. Meanwhile, the inventors have focused on brainwaves which are hardly affected by the peripheral circulatory system as an indicator for objectively evaluating pain, arriving at the conclusion that pain can be differentiated and classified by observing the change during latency/amplitude in response to pain stimulation and performing trend analysis. In particular, instantaneous pain and throbbing sustained pain can also be distinguishable by the trend analysis of the present disclosure. Since instantaneous pain is pain during a short time segment, associated brain activity can decrease if a time direction averaging method over at least several tens of seconds is used in trend analysis (e.g., significant correlation with pain evaluation is not observed). Meanwhile, sustained pain is continuous, so that significant correction with pain evaluation can be rather strengthened by a time direction averaging method. The inventors have focused on brainwaves that are less susceptible to the effect of the peripheral circulatory system as an indicator for objective evaluation of pain, and have thus found that the accuracy is increased by observing the change in amplitude/latency with respect to the pain stimulation and applying the reference stimulation.

One of the important points of the present disclosure is in the ability to distinguish whether pain is such pain that "requires therapy", rather than the intensity in itself, and this can be diagnosed more accurately by the reference stimulation. Therefore, it is important that "pain" can be clearly categorized based on the concept of "therapy". For example, this leads to "qualitative" classification of pain such as "pleasant/unpleasant" or "unbearable". For example, the position of a "pain index", baseline, and the relationship thereof can be defined. In addition to a case of n=2, cases where n=3 or greater can also be envisioned. When n is 3 or greater, pain can be separated into "not painful", "comfortable pain", and "painful". For example, pain can be differentiated as "unbearable, need therapy", "moderate", or "painful, but not bothersome". When the trend an lysis of the present disclosure is used, "unbearable" and "painful but bearable" pain can be distinguished by identifying a threshold value for long/short duration of a signal associated with strong pain.

As used herein, "subjective pain sensation level" refers to the level of sensation of pain of an object, and can be expressed by conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like.

PREFERRED EMBODIMENTS

The preferred embodiments of the present disclosure are described hereinafter. It is understood that the embodiments provided hereinafter are provided to facilitate better understanding of the present disclosure, so that the scope of the present disclosure should not be limited by the following descriptions. Thus, it is apparent that those skilled in the art can refer to the descriptions herein to make appropriate modifications within the scope of the present disclosure. It is also understood that the following embodiment of the present disclosure can be used individually or as a combination.

Each of the embodiments described below provides a comprehensive or specific example. The numerical values, shapes, materials, constituent elements, positions of arrangement and connection forms of the constituent elements, steps, order of steps, and the like in the following embodiments are one example, which is not intended to limit the Claims. Further, the constituent elements in the following embodiments that are not recited in the independent claims showing the most superordinate concept are described as an optional constituent element.

(Reference Stimulation)

In one aspect, the present disclosure provides a method for building a model for identifying a reaction of an organism, the method comprising: acquiring a plurality of reaction data from an organism, including: acquiring a first reaction data on the organism being in a first state; and acquiring a second reaction data on the organism being in a second state; and building a model unique to the organism for identifying the reaction of the organism, based on the plurality of acquired reaction data. Various analyses, diagnoses, and tests can be performed accurately by applying a reference stimulation.

In one embodiment, the first reaction data is data on the organism being in the first state and stimulation is applied to the organism, and the second reaction data is data on the organism being in the second state and stimulation is applied to the organism.

In one embodiment, the acquiring the plurality of reaction data from the organism includes: acquiring a third reaction data on the organism being in the first state and no stimulation is applied to the organism; and acquiring a fourth reaction data on the organism being in the second state and no stimulation is applied to the organism.

In one embodiment, the reaction of the organism includes a reaction with pain and a reaction with no pain.

In one embodiment, the first state is a state in which noise is added to the reaction data, and the second state is a state in which no noise is added to the reaction data.

In one embodiment, the second state include an action by the organism to block at least one of the five senses. In one embodiment, the second state includes a state in which the organism is performing a visual deprivation behavior, a hearing deprivation behavior, or a combination thereof.

In one embodiment, the building the model includes: updating an existing model for identifying a reaction of an organism, based on the plurality of acquired reaction data, to build a model unique to the organism.

In one embodiment, the building the model includes: selecting a model unique to an organism from a plurality of existing models for identifying the reaction of the organism, based on the plurality of acquired reaction data, to build a model unique to the organism.

In one embodiment, the reaction data acquired upon the application of stimulation can also be obtained by causing the object to recollect the applied stimulation. More accurate response data can be obtained as the interval between the stimulation application and stimulation recollection is shorter. For example, recollection of pain by an object may present reaction data as if the pain was actually applied.

In one aspect, a system is provided that comprises: a model built by a method of the present disclosure; an acquisition means of acquiring a reaction data from an organism; and an output means of outputting a result of the model identifying the reaction of the organism b sed on the reaction data acquired by the acquisition means.

In another aspect, the present disclosure provides a system comprising: an acquisition means of acquiring a reaction data from an organism, the acquisition means including a referencing mode and a measuring mode; a model building means of building a model using the reaction data acquired from the acquisition means as a reference stimulation, wherein the model is built by building a model unique to the organism for identifying the reaction of the organism, based on a plurality of reaction data acquired by: acquiring a plurality of reaction data from the organism in the referencing mode, including: acquiring a fir t reaction data on the organism being in a first state; and acquiring a second reaction data on the organism being in a second state; and an output means of outputting a result of the model identifying the reaction of the organism based on the reaction data acquired by the acquisition means in the measuring mode. Various analyses, diagnoses, and tests can be performed more accurately for individuals by customizing each application of the reference stimulation. This embodiment can be mentioned as an example of accomplishment of Precision Medicine (also referred to as tailor-made machine learning (tailor-made method)).

In another aspect, the present disclosure provides the above system further comprising a standard model where the model building means modifies the standard model based on the plurality of reaction data. Various analyses, diagnoses, and tests can be performed accurately by applying a reference stimulation. Herein, even if a standard model is assumed in advance, it is often the case that such a standard model is not optimized for the individual. Thus, in such a case, various analyses, diagnoses, and tests can be performed accurately by applying a reference stimulation.

(Program)

The present disclosure further provides a program for building a model for identifying a reaction of a organism, the program being executed by a computer system equipped with a processor, where the program causes the processor to execute processing that includes: building a model unique to the organism for identifying the reaction of the organism, based on a first reaction data on the organism being in a first state and a second reaction data on the organism being in a second state.

(Standalone)

In the method for building a model for identifying a reaction of an organism of the present disclosure, all steps can be executed in an analyzer such as a pain analyzer provided to a user, for example. That is, the pain analyzer can be a stand-alone type. An analyzer, such as a stand-alone pain analyzer, conducts a series of operations of applying a reference stimulation to an organism, acquiring the reaction data thereof, and building a model unique to the organism based on the acquired reaction data. As a result, an analyzer such as a pain analyzer can accurately identify the reaction of the organism by using a model unique to the organism without communicating with the outside.

The computer system that executes the program for building the model for identifying the organism reaction of the present disclosure can be, for example, an analyzer such as a pain analyzer provided to the user. The processor of an analyzer, such as a pain analyzer, conducts a species of operations of applying a reference stimulation to an organism, acquiring the reaction data thereof, and building a model unique to the organism based on the acquired reaction data. As a result, an analyzer such as a pain analyzer can accurately identify the reaction of the organism by using a model unique to the organism without communicating with the outside.

(Cloud)

The method for building a model for identifying the reaction of the organism of the present disclosure can be performed, for example, in a system that include an analyzer, such as a pain analyzer, provided to a user and a server device to which the analyzer, such as a pain analyzer, can be connected via a network. Some of the steps of the method for building a model for identifying the reaction of the organism can be performed by the analyzer, such as a pain analyzer, and the rest of the steps can be performed by the server device. For example, the pain analyzer can perform the step of acquiring multiple reaction data from the organism and transmit the acquired multiple reaction data to the server device, and the server device can receive multiple reaction data from the analyzer, such as the pain analyzer, and perform the step of building a biological model for identifying the reaction of the organism, based on the received multiple reaction data. As a result, the processing load of the analyzer such as the pain analyzer can be reduced.

(Large-Scale System)

In another aspect, the present disclosure further provides a system for building a model for identifying a reaction of an organism. The system is equipped with a processor and an analyzer, where the processor executes processing including the building of a model unique to the organism for identifying the reaction of the organism, based on a first reaction data on the organism being in a first state and a second reaction data on the organism being in a second state. Various analyses, diagnoses, and tests can be performed more accurately for individuals by customizing each application of the reference stimulation. This embodiment can be mentioned as an example of accomplishment of Precision Medicine (also referred to as tailor-made machine learning (tailor-made method)). First of all, as an application in a large-scale system, it is possible to attempt to differentiate pain using multiple standard models stored in the database, but such a case is also conceivable that makes fine adjustments each time using a reference stimulation.

(System)

Figure 49:
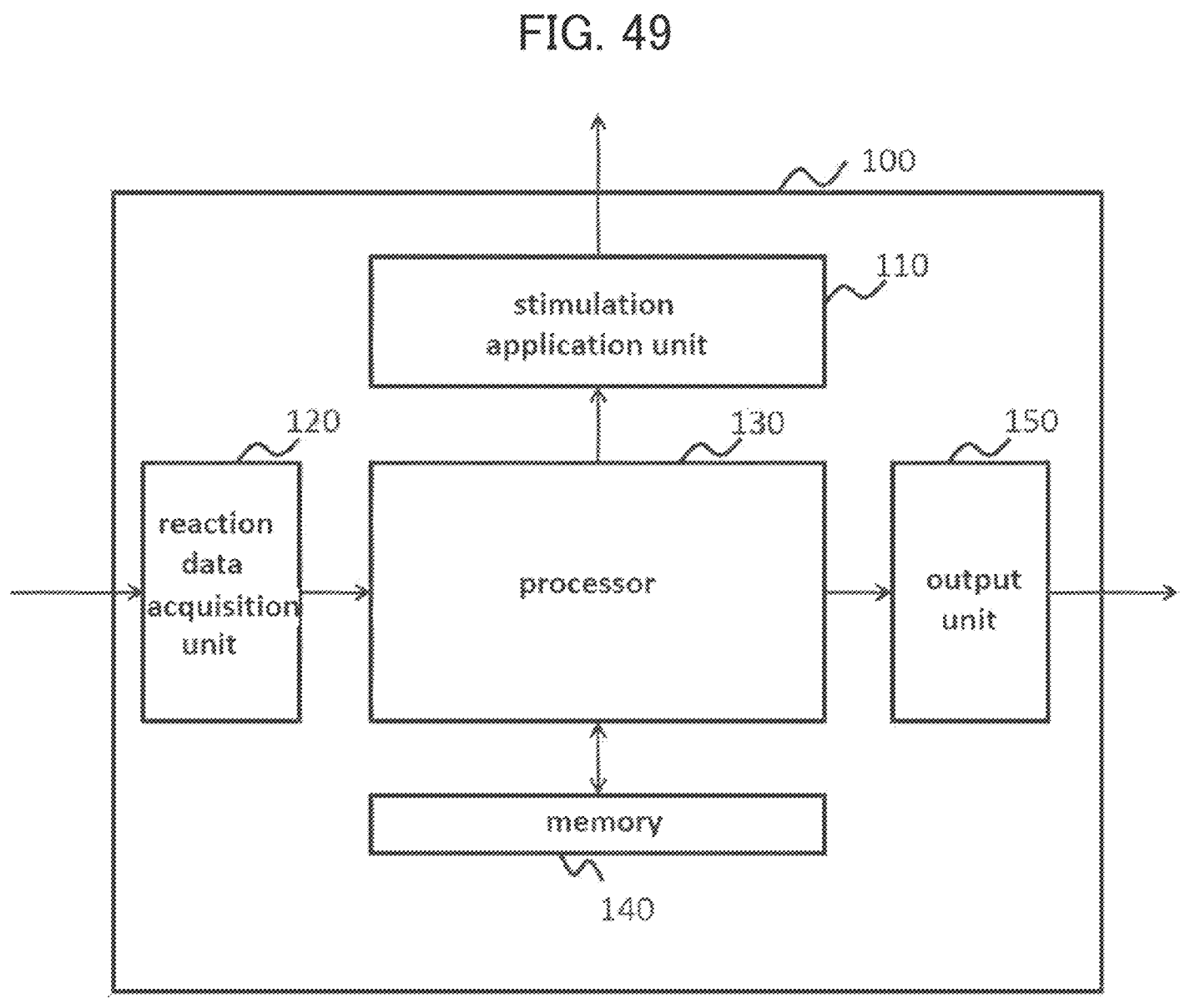

FIG. 49 shows an example of the configuration of a system 100 for building a model for identifying the rea tion of an organism of the present disclosure. Herein, a pain analyzer will be described.

The system 100 may be, for example, a pain analyzer provided to the user.

The system 100 may include a stimulation application unit 110, a reaction data acquisition unit 120, a processor 130, a memory 140, and an output unit 150.

The stimulation application unit 110 is configured to give a stimulation to an organism. The stimulation given by the stimulation application unit 110 can be, for example, at least one of electrical stimulation, cold stimulation, thermal stimulation, physical stimulation, and chemical stimulation. The stimulation application unit 110 may have a configuration according to the stimulation to be applied. As a exemplary configuration that applies electrical stimulation, cold stimulation, thermal stimulation, physical stimulation, and chemical stimulation, a miniaturized Pain Vision (OSACHI). As an exemplary configuration, a miniaturized version of Pain Vision (OSACHI) can be considered for the electrical stimulation and a miniaturized version of Pathway (MEDOC) can be considered for the cold stimulation and thermal stimulation.

The reaction data acquisition unit 120 is configured to acquire reaction data from an organism. The reaction data acquisition unit 120 acquires, for example, reaction data by an organism stimulated by the stimulation application unit 110. The reaction data acquisition unit 120 may acquire the reaction data by, for example, measuring the reaction data by the organism stimulated by the stimulation application unit 110 in real time, or the reaction data acquisition unit 120 may acquire the reaction data from the storage unit, in which the reaction data by the organism stimulated by the stimulation application unit 110 is stored in advance.

The processor 130 executes the processing of the system 100 and controls the operation of the system 100 as a whole. The processor 130 reads a program stored in the memory 140 and executes the program. This allows the system 100 to function as a system that performs desired steps. When the data acquired by the reaction data acquisition unit 120 is in a format unsuitable for processing, the processor 130 may execute processing for converting the data into a format suitable for the processing. The processor 130 may be implemented by a single processor or by a plurality of processors.

The memory 140 stores a program required to execute the processing of the system 100, data required to execute the program, and the like. The memory 140 may store program for causing the processor 120 to execute the processing for building a model for identifying a reaction of an organism (e.g., a program that achieves a part of the flow shown in FIG. 60, and a program that achieves the processing shown in FIG. 61, which will be described below). The processor 120 may store a program for causing the processor 120 to execute the processing to identify a reaction of an organism using the built model. Here, any approaches may be taken to store the program on the memory 140. For example, the program may be pre-installed in the memory 140. Alternatively, the program may be installed on the memory 140 by being downloaded over the network. In this case, any type of network may be used. The memory 140 may be implemented by any storage means.

The output unit 150 is configured to be able to output data to the outside of the system 100. The output unit 150 can output, for example, a built model unique to the organism. The output unit 150 can output the result of identifying the reaction of the organism using, for example, the built model. Any modes may be taken for the output unit 150 to output augmented data. For example, when the output unit 150 is a transmitter, the transmitter may output data by transmitting the data to the outside of the system 100 via a network 500. For example, when the output unit 150 is a data writing device, the data may be output by writing the data to the storage medium or a database unit 200 connected to the system 100. For example, the output unit 150 may output data by converting the data into a format that can be handled by the hardware or software of the data output destination, or by adjusting the response speed that can be handled by the hardware or software of the data output destination.

In the building with the use of the reference stimulation, this can be achieved by referring to, for example, WO 2018/038121, WO 2019/009420, etc., which the present inventors have previously filed, and executing the processing of reference stimulation on them. For example, it can be understood that there are three types of model building methods using a reference stimulation: (i) building of a new model, (ii) update of an existing model, and (iii) selection of an existing model.

Figure 60:
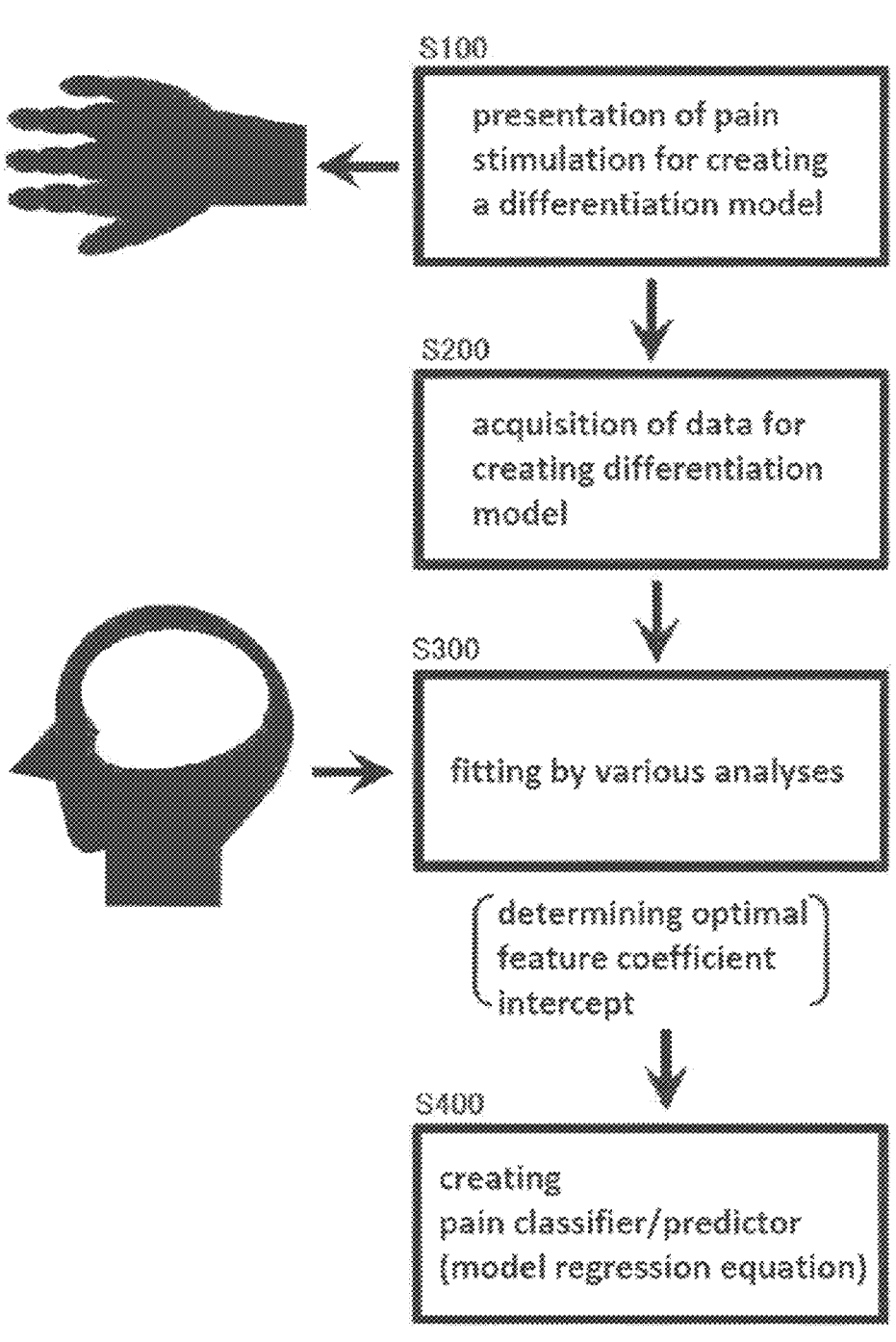
FIG. 60 shows an example of model regression equation generation.
Figure 61:
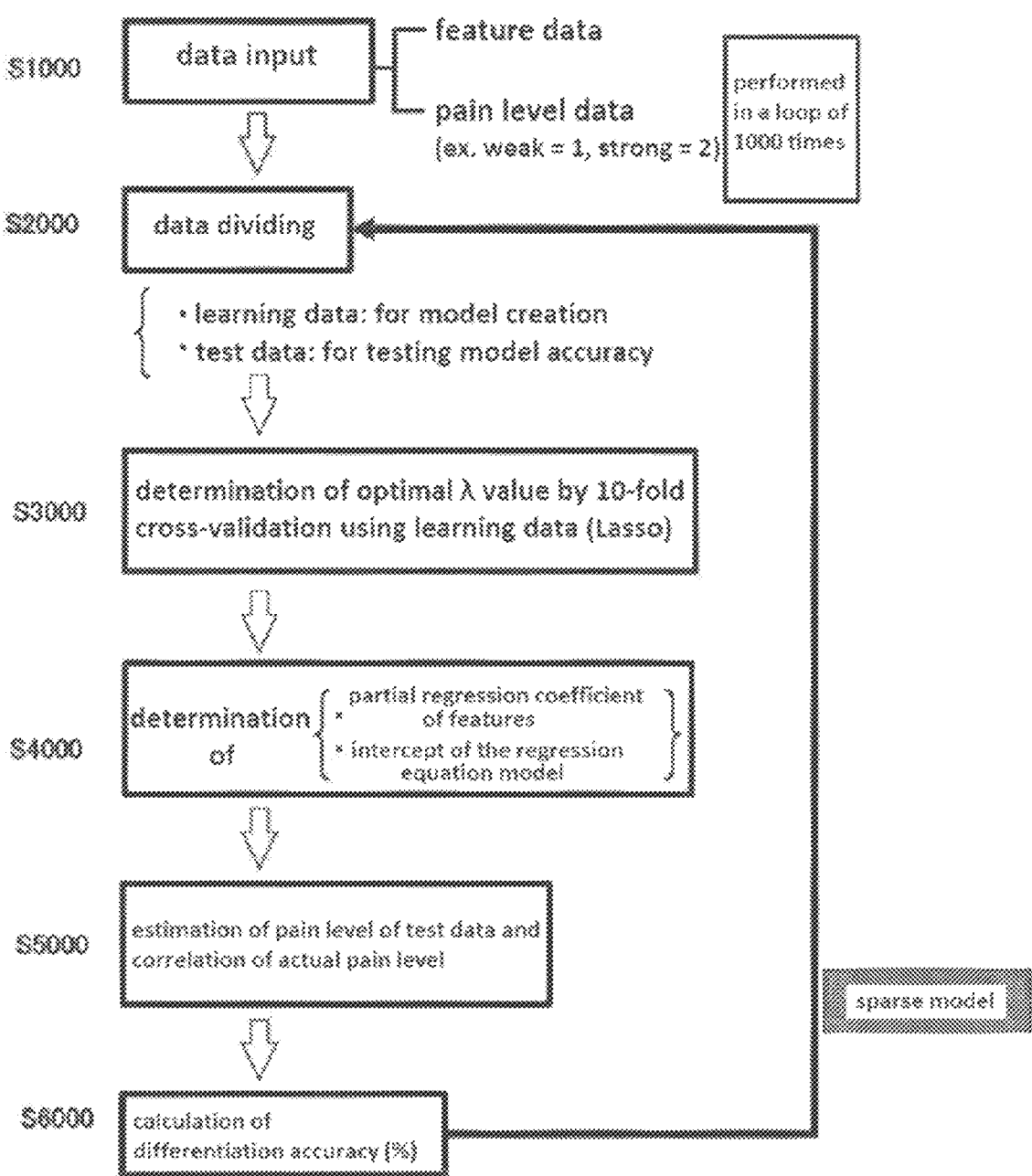
FIG. 61 is an example of a flowchart showing a flow of sparse model analysis.

An exemplary approach for calculating a pain level will be described with reference to FIG. 60.

In the step (S200) of acquiring model brain wave data corresponding to the stimulation intensity for t e model (presentation of pain stimulation for creating a differentiation model, S100) or analysis data thereof (acquisition of data for creating differentiation model), the object being estimated is stimulated with a plurality of levels (strength or greatness) of stimulations (e.g., low temperature stimulations, electrical stimulations, or the like) to acquire the brainwaves. The number of types of the stimulation intensities may be a number required for fitting to the pain function, which generally needs to b, for example, at least three types, weak, moderate and great. This number of types is not necessarily required since the application to model building is possible even with one type or two types by combining with previously acquired information. Meanwhile, when the application is newly performed, it may be generally advantageous to perform stimulating with at least 3 types, preferably four types, five types, six types or more types of levels of stimulations. If there are three types, it is preferable because weak, medium and strong can be observed. If there are more types than that, the function pattern can be understood in more detail, which is ideal, but the present invention not limited thereto. In this regard, since burden on the object being estimated should be as little as possible, the stimulation intensity has high invasiveness to the object being estimated (in other words, the intensity that a subject cannot bear) and it is preferable that the number thereof be minimum or zero. Meanwhile, since stimulation with high invasiveness to an object being estimated may be required for a more accurate fitting, a minimum number can be taken in in accordance with the purpose. For example, the number of types of levels with high invasiveness to an object being estimated may be at least one type, at least two types, or at least three types, or may be four types or more when allowed by the object being estimated. The brainwaves data or analysis data thereof is also referred to as brain activity data or brain activity amount. For example, the data includes amplitude data ("EEG amplitude"), frequency characteristics, and the like. Such brainwaves data can be acquired by using any approach well known in the art. The brainwaves data can be acquired by measuring the electric signal of the brainwaves, and is displayed by the electric potential (which can be displayed in μv or the like) as amplitude data or the like. The frequency characteristics are displayed in terms of power spectral density or she like.

S300 is a step of: setting a target pain level; introducing the model brainwave features and the pain level into sparse model analysis, finding an appropriate A (preferably an optimal λ); determining a parameter (partial regression coefficient) of the model brainwave features and a constant (intercept) of the algorithm, corresponding to the appropriate λ (preferably the optimal λ); and generating a regression model. Here, the pain level is set, and a regression model (pain classifier/predictor (model regression equation)) is created using the brainwave features acquired in Step b) (S400). The regression model can be created using any approach known in the art. As such a specific an lysis approach, for example, LASSO can be mentioned.

As an example of model building using a reference stimulation, model building using sparse modeling will be described hereinafter.

<Regression Model Generation>

Shown below is a method for generating a regression model for differentiating or estimating the pain of an object being estimated, based on the brainwaves of the object being estimated. This method includes the steps of: a) acquiring model brainwaves data corresponding to the reference stimulation or analysis data thereof; b) extracting model brainwave features from the brainwaves data or analysis data thereof; and c) setting a target pain level, introducing the model brainwave features (independent variable) and the pain level (dependent variable) into sparse model analysis, finding an appropriate A (preferably an optimal A), determining a parameter (partial regression coefficient) of the model brainwave features and a constant (intercept) of the algorithm, corresponding to the appropriate A (preferably the optimal A), and generating a regression model.

In the sparse model analysis, data input, algorithm determination of the differentiation/estimation nit, and output of differentiation/estimation can be performed multiple times (for example, 1000 times or more or less) to obtain an appropriate value (preferably optimization). For example, the above may be performed 2000 times, 3000 times, 5000 times, 10000 times.

The appropriate (preferably optimal) λ coefficient is used to determine the feature parameter (coefficient) and the algorithm constant (intercept). This is repeated 1000 times during the differentiation and estimation of the test data, and the average thereof is the differentiation accuracy. It can be said that the strictness is considerably different from the accuracy determination of the prior art. In using a regression model generated for the general public, it is preferable to perform calibration for each individual. It is possible to add a technique for correcting the feature parameter (coefficient) and algorithm constant (intercept) used in this model for each individual.

In performing sparse model analysis when modeling is performed in the present disclosure, the following points should be noted for the modeling. For example, in LASSO, all the coefficients are multiplied by the λ value in the same way to make them regular, so the features used need co be treated in the same unit.

<Sparse Modeling>

A more detailed procedure for exemplary sparse modeling will be described below.

In S1000, data is input, and feature data a d pain level data are input.

In S2000, the data is divided. Here, it is divided into learning data and test data, and the learning data is used for model determination while the test data is used for testing model accuracy.

In S3000, an appropriate (preferably optimal) A value is determined by cross-validation using learning data (10-fold cross-validation is illustrated in the figure) (for example, LASSO analysis).

In S4000, the parameter (partial regression coefficient) of the features and the constant (intercept) of the regression equation model are determined.

In S5000, the pain level of the test data is estimated and the actual pain level is collated. For collation, there is an existing regression model, for example, and the estimated value thereof is determined as follows: strong pain≥0.3 and weak pain<0.3. Accordingly, when the pain is ≥0.3, it is set to "2", and when the pain is <0.3, it is set to "1". Here, since the actual pain level is also expressed with "strong=2" and "weak=1", the differentiation accuracy is calculated as a correct answer if both are collated and match each other.

In S6000, the differentiation accuracy (%) s calculated. After returning from S6000 to S2000, the repetition accuracy is calculated a plurality of times (1000 times in FIG. 61).

In each embodiment described herein, generation of a sample for differentiating the reaction of an organism to pain may be performed by, for example, the following method. In other words, a method comprising:

a) the step of performing a pain test on a plurality of subjects to acquire a plurality of COVAS data;

b) the step of averaging the plurality of COVAS data to create a COVAS template;

c) the step of performing the pain test on the organism to acquire brainwaves data or analysis data thereof from the organism;

d) the step of cutting out the brainwaves data or analysis date thereof based on the COVAS template; and e) the step of learning the cut out brainwaves data or analysis data thereof as data for learning and a value of a COVAS template corresponding to the cut out brainwaves data or analysis data thereof as a label to create a model.

This method is characterized in that a pain test is performed beforehand to a plurality of subjects that are not an object, where the plurality of COVAS data acquired from the pain test is averaged to create a COVAS template.

The pain test is a test of imposing any pain, where the pain is imposed on a plurality of subjects in accordance with a predetermined profile. The pain may be, for example, electrical stimulation, or may be thermal stimulation. The pain, for example, may be stimulation with an intensity that increases in a step-like manner from weak stimulation to strong stimulation, may be stimulation with an intensity that decreases in a step-like manner from strong stimulation to weak stimulation, may be a combination thereof, or may be stimulation with an intensity that fluctuates between weak stimulation and strong stimulation.

The COVAS (computerized visual analog scale) data expresses subjective evaluation of pain by a plurality of subjects when a pain test has been performed to the plurality of subjects. The COVAS data is associated with e ch subjective evaluation to each pain in the pain test. The COVAS data has the length of the amount of time of the pain test.

The plurality of subjects may preferably be healthy people against the pain. This means that a COVAS template expresses the subjective evaluation of pain by healthy people by averaging the COVAS data by a plurality of subjects.

Furthermore, this method is characterized in that the brainwaves data or analysis data thereof acquired by performing the pain test on an object differentiating pain is cut out based on a COVAS template that has been created beforehand. Herein, in the pain test, the pain is imposed on the object in accordance with the same profile as the pain test performed for creating a COVAS template.

Upon cutting out the brainwaves data or analysis data hereof based on a COVAS template that has been created beforehand, it is preferable that timing of initiation of pain stimulation be made consistent between a COVAS template and brainwaves data or analysis data thereof to be cut out. This enables the COVAS template to correspond to the cut out brainwaves data or analysis data thereof as a label. In other words, it becomes possible to differentiate what kind of pain causes the brainwaves data or analysis data thereof via the subjective evaluation of the COVAS template. The brainwaves data or analysis data thereof labeled by the COVAS template can be used for learning for creating a model for differentiating pain.

The timing of initiation of pain stimulation may be able to be made consistent by, for example, matching a trigger showing the timing of initiation of pain stimulation comprised in the brainwaves data or analysis data thereof and a trigger showing the timing of initiation of pain stimulation comprised in the COVAS template.

Furthermore, this method is characterized by learning the cut out brainwaves data or analysis data thereof as data for learning and a value of a COVAS template corresponding to the cut out brainwaves data or analysis date thereof as a label to create a model.

The methodology used for learning may be any methodology. The methodology used for learning may be, for example, LSTM (long short-term memory). For example, learning is performed using the cut out brainwaves data or analysis data thereof for input of LSTM and a value of the COVAS template or the label thereof (supervisory output).

In each of the embodiments described above, each constituent element can be materialized by being configured with a dedicated hardware or by implementing software program that is suited to each constituent element. Each constituent element can be materialized by a program implementation unit such as a CPU or a processor reading out and implementing a software program recorded on a recording medium such as a hard disk or semiconductor memory. In this regard, software materializing the pain estimation apparatus of each of the embodiments described above or the like can be a program such as those described below.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present disclosure as been described while showing preferred embodiments to facilitate understanding. The present disclosure is described hereinafter based on Examples. The above descriptions and the following Examples are not provided to limit the present disclosure, but for the sole purpose of exemplification. Thus, the scope of the present disclosure is not limited to the embodiments or the Examples specifically described herein and is limited only by the scope of claims.

EXAMPLES

Examples are described hereinafter. The objects used in the following Examples were handled, as needed, in compliance with the standards of the Osaka University, and the Declaration of Helsinki and ICH-GCP in relation to clinical studies.

Example 1

Closed Eye Sample Augmentation

In this example, an experiment of closed-eye sample augmentation (Long short-term memory (LSTM) 4 Class) was performed. The method and the like will be described below.

(Method 1)

The four classes, "no pain•having pain•no pain with noise•having pain with noise", were differentiated using LSTM. Noise tests and noise tests during pain stimulation were performed to label the class including noise. Subjects had their eyes closed in some trials (eye-closing task). The conditions of the experimental trial conducted ace described below.

Experimental Trial:
  (1) artifact1: noise test (tightly closing the eyes, stretching the body, reading out loud), eyes opened
  (2) artifact2: noise test (tightly closing the eyes, stretching the body, reading out loud), eyes opened
  (3) artifact_pain1: noise test upon pain stimulation (voluntary reaction with noise inputted), eyes opened
  (4) artifact_pain2: noise test upon pain stimulation (voluntary reaction with noise inputted), eyes opened
  (5) ref: pain stimulation, rest, eyes closed
  (6) main1: pain stimulation, rest, eyes closed
  (7) main2: pain stimulation, rest, eyes closed
  (8) main3: noise test upon pain stimulation, eyes closed
  (9) 2temp: pain stimulation (moderate: 46° C., great: 48° C.), eyes opened
  (10) 2temp_artifact: noise test upon pain stimulation (moderate: 46° C., great: 48° C.) (voluntary reaction with noise inputted), eyes opened (Method 2)

The experiment was conducted using 6 channels of the forehead as electrodes. The following frequency bands were used in respective channels.

$$f1 = 2 - 5 \text{ Hz}$$
$$f2 = 5 - 8 \text{ Hz}$$
$$f3 = 8 - 14 \text{ Hz}$$
$$f4 = 14 - 29 \text{ Hz}$$
$$f5 = 31 - 40 \text{ Hz}$$
$$f6 = 40 - 49 \text{ Hz}$$

At the time of feature extraction, EOG removal and bandpass filter were applied. Cutting out while shifting were performed for the respective classes, "no pain with no noise", "having pain with no noise", "no pain with noise" and "having pain with noise", which increased original samples, respectively. A sample augmentation method was applied to the acquired samples, for each individual, to create a model that fits the individual.

Next, the evaluation standards (differentiation precision, relevance ratio, recall ratio, F1 value) in the 2 classes and 4 classes were compared with each other. This time, the method of differentiation by setting the threshold value was not performed, and the comparison was made using the softmax function for both 2 classes and 4 classes.

Figure 28:
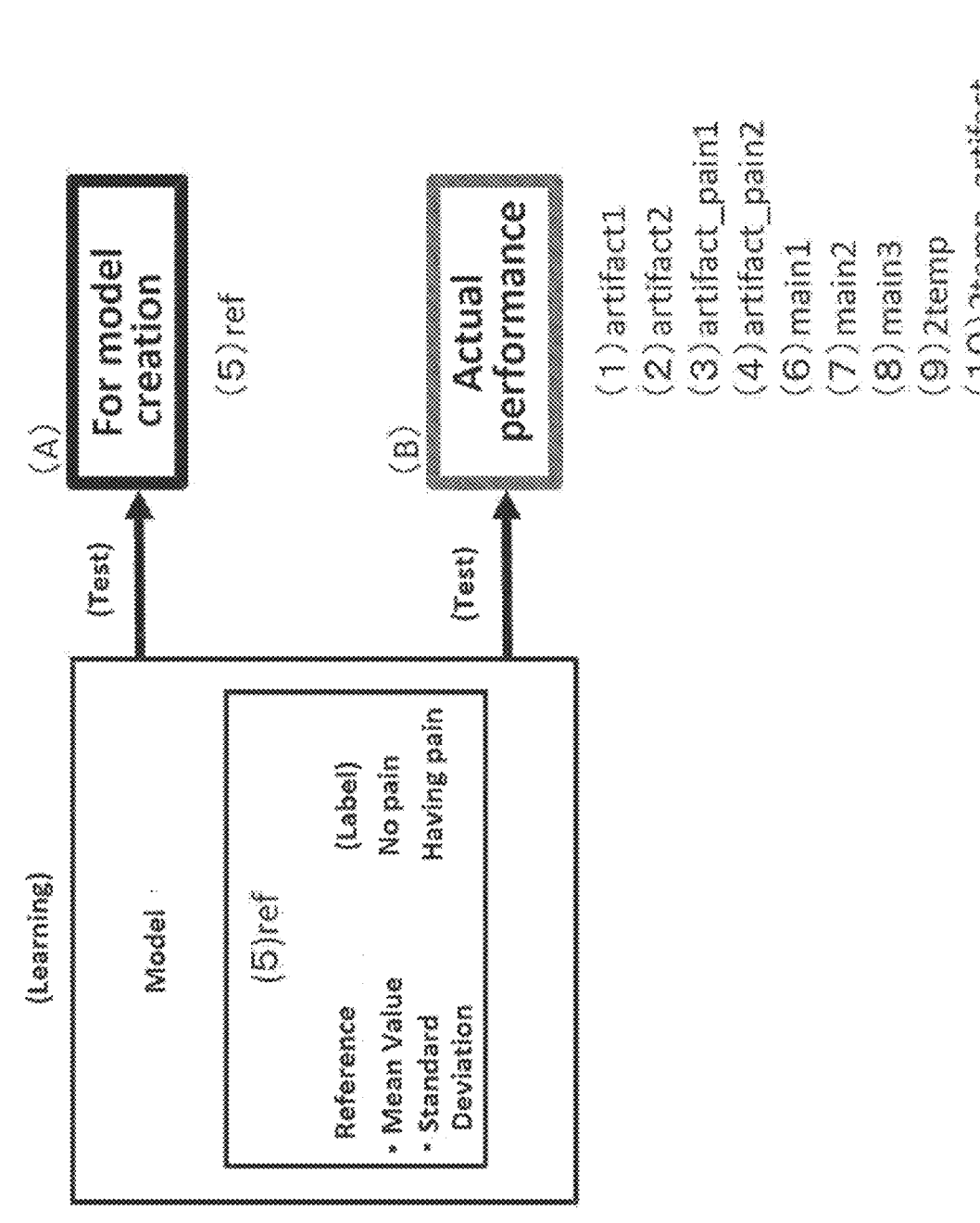
FIG. 28 shows a flow of 2-class LSTM analysis.

FIG. 28 shows the flow of the two-class LSTM, which is a prior art. FIG. 1 shows analysis conditions.

Specifically, the analysis conditions are as follows.

The following network was used layers=6×1 Layer array with the next layer:

| 1 sequence input | 7-dimensional sequence input |
| 2 LSTM | LSTM with 300 hidden units |
| 3 Dropout | 50% dropout |
| 4 Fully Connected | 4 Fully Connected Layer |
| 5 Softmax | Softmax |
| 6 Classification output | crossentropyex |

Hyperparameters are as follows.

Parameter update method: Adam
Learning rate: 0.001
Mini batch size: 128
Number of epochs: 20
L2 regularization ($\lambda$): 0.01
Dropout: 0.5

(Off-Line Chronological Data Analysis)

Off-line chronological data analysis was performed as follows.

(1) Differentiation value (softmax: 4 classes)→(0: no pain with no noise, 1: having pain with no noise, 2: no pain with noise, and 3: having pain with noise) . . . The results of all binding layers were inputted to the softmax function and the class with the highest percentage was determined as the differentiation value.

(2) Differentiation value (softmax: 2 classes)→0: no pain and 1: having pain) . . . The result in the (1) (4 classes) was converted to the 2 classes.

([4 classes]0, 2→[2 classes]0, [4 classes]1, 3→[2 classes] 1)

This time, the differentiation values of these 2 classes and the correct label (where there is thermal stimulation) were compared to perform the evaluation (differentiation precision, relevance ratio, recall ratio, F1 value).

The following 8 trials have the correct label of thermal stimulation:

(3) artifact_pain1, (4) artifact_pain2, (5) ref, (6) main1, (7) main2, (8) main3, (9) 2temp, (10) 2temp_artifact.

(3) Pain estimation value: −log(1-x)→a pain estimation value converted from a pain estimation value (0-1) by −log(1−x) . . . . In setting a threshold close to 1 (e.g., 0.99), this makes it easier to see the fluctuation in the estimated value.

(4) Brainwave: Fp1

(5) Feature: 147×15 features . . . features with 147 features and 15 chronological sequences used as a unit.

(Results)

The results are shown below.

Figure 3:
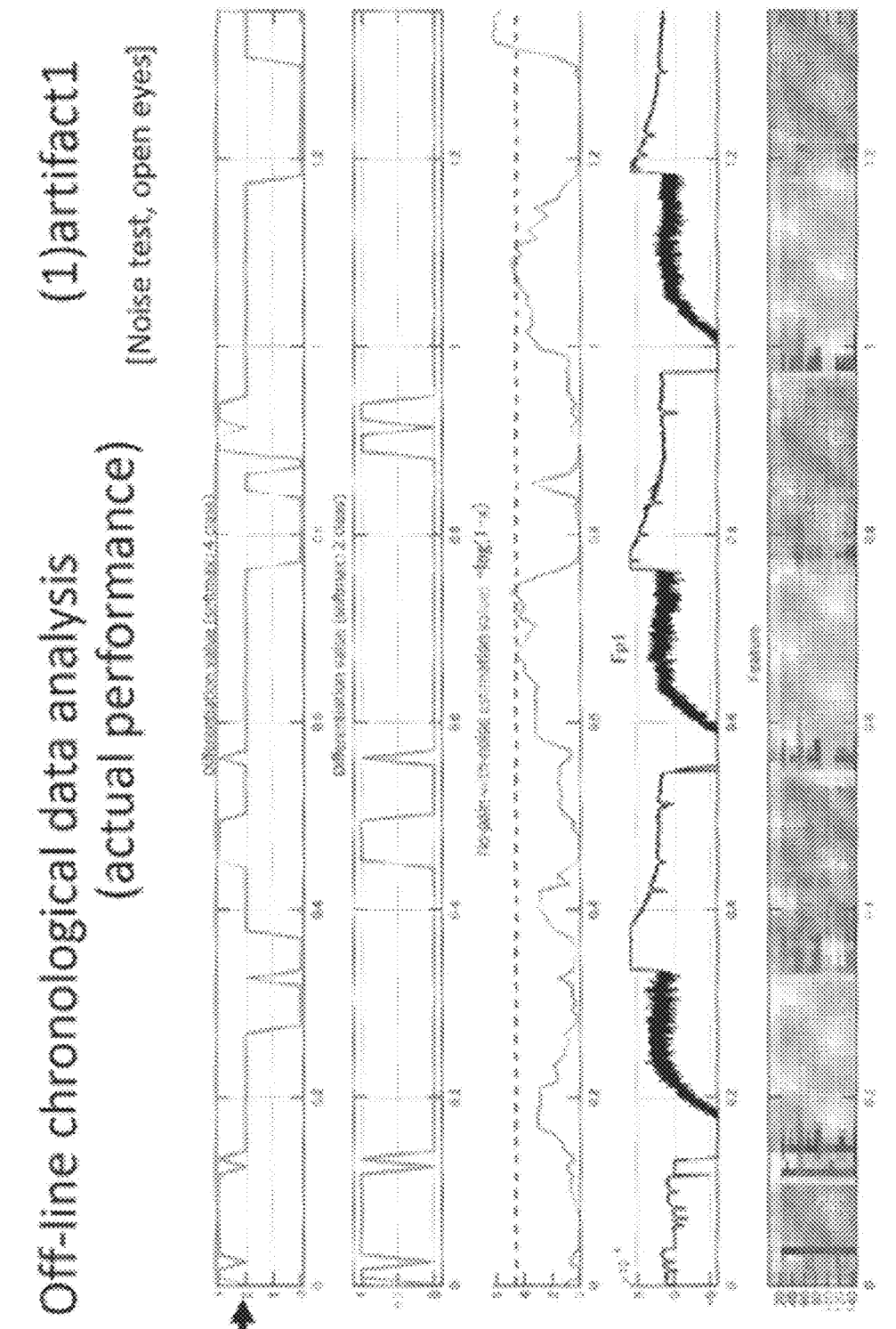
FIG. 3 shows results of performing the off-line chronological data analysis on the raw data shown in FIG. 2. In 4 classes, it should have been determined as (2) no pain with noise; however, mis-differentiation was observed.

FIG. 2 shows raw data under artifact1 (noise test (tightly closing the eyes, stretching the body, reading out loud), eyes opened) conditions. FIG. 3 shows the results of performing the off-line chronological data analysis. In 4 classes, it should have been determined as (2) no pain with noise; however, it can be seen that mis-differentiation was observed.

Figure 4:
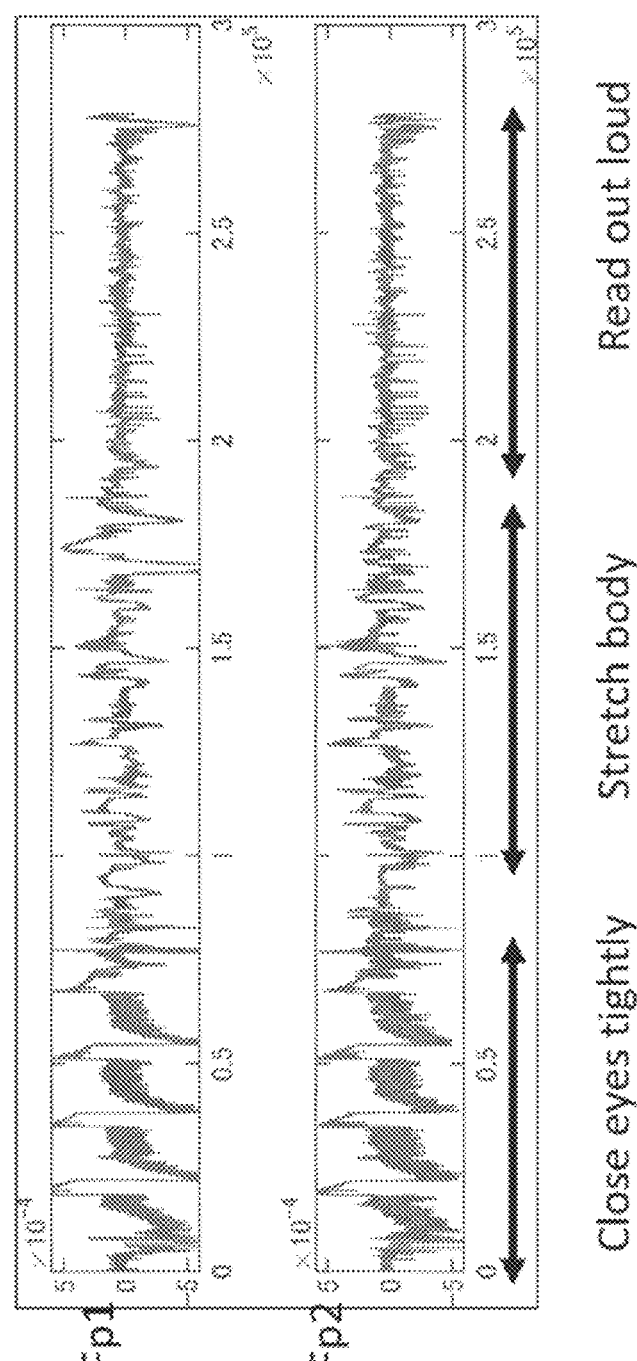
FIG. 4 shows raw data (artifact2) used for 4 class LSTM analysis. The conditions for artifact2 are noise test (tightly closing the eyes, stretching the body, reading out loud), eyes opened.
Figure 5:
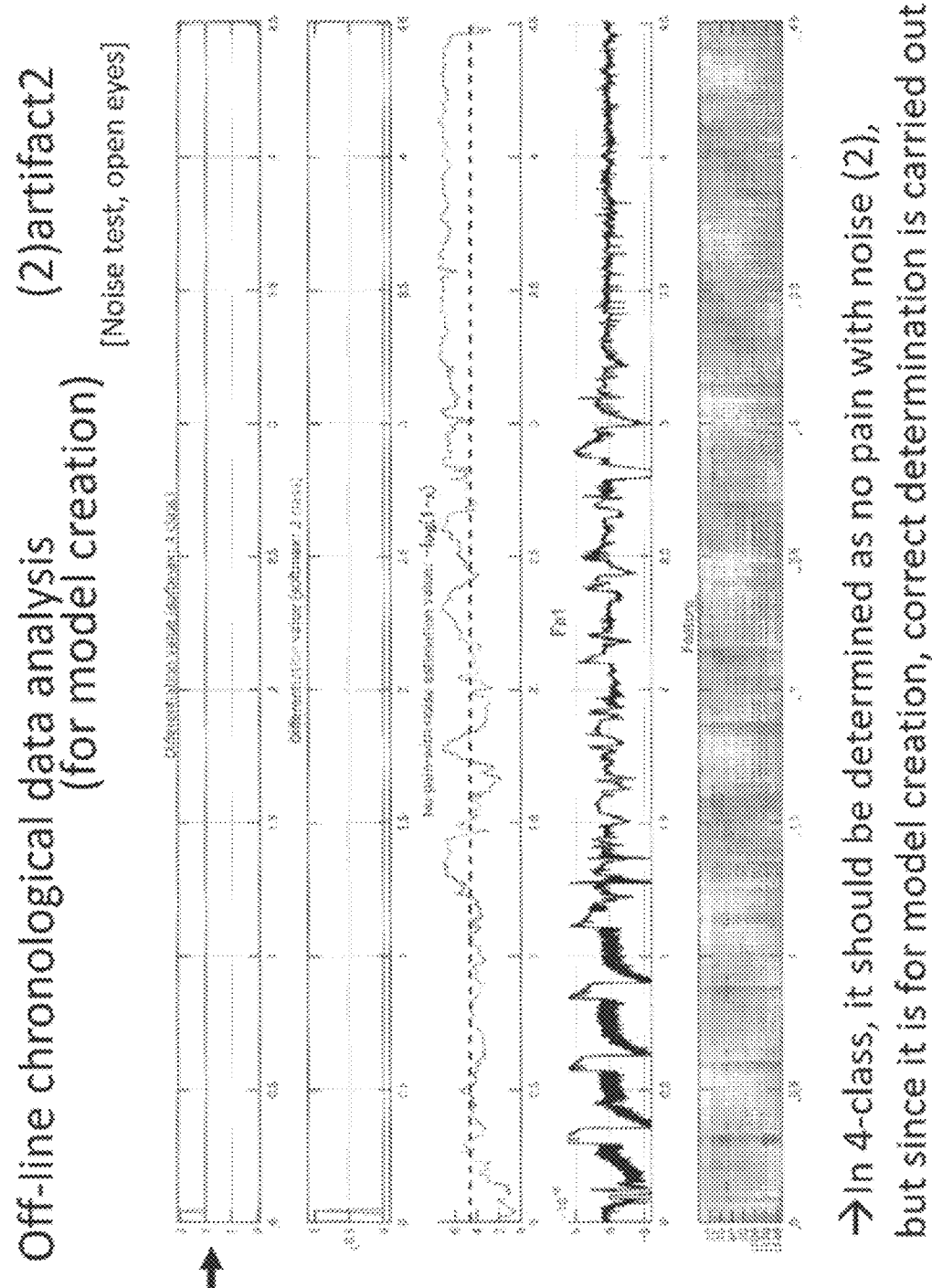
FIG. 5 shows results of performing an off-line chronological data analysis on the raw data show in FIG. 4. In 4 classes, it should have been determined as (2) no pain with noise; however, it can be seen that determination was made correctly since it was for model creation.

FIG. 4 shows raw data under artifact2 (noise test (tightly closing the eyes, stretching the body, reading out loud), eyes opened) conditions. FIG. 5 shows an off-line chronological data analysis for model creation. In 4 classes, it should have been determined as (2) no pain with noise; however, it can be seen that determination was made correctly since it was for model creation.

Figure 6:
FIG. 6 shows raw data (artifact_pain1) used for 4 class LSTM analysis. The conditions for artifact_pain1 are noise test upon pain stimulation (voluntary reaction with noise inputted), eyes opened.
Figure 7:
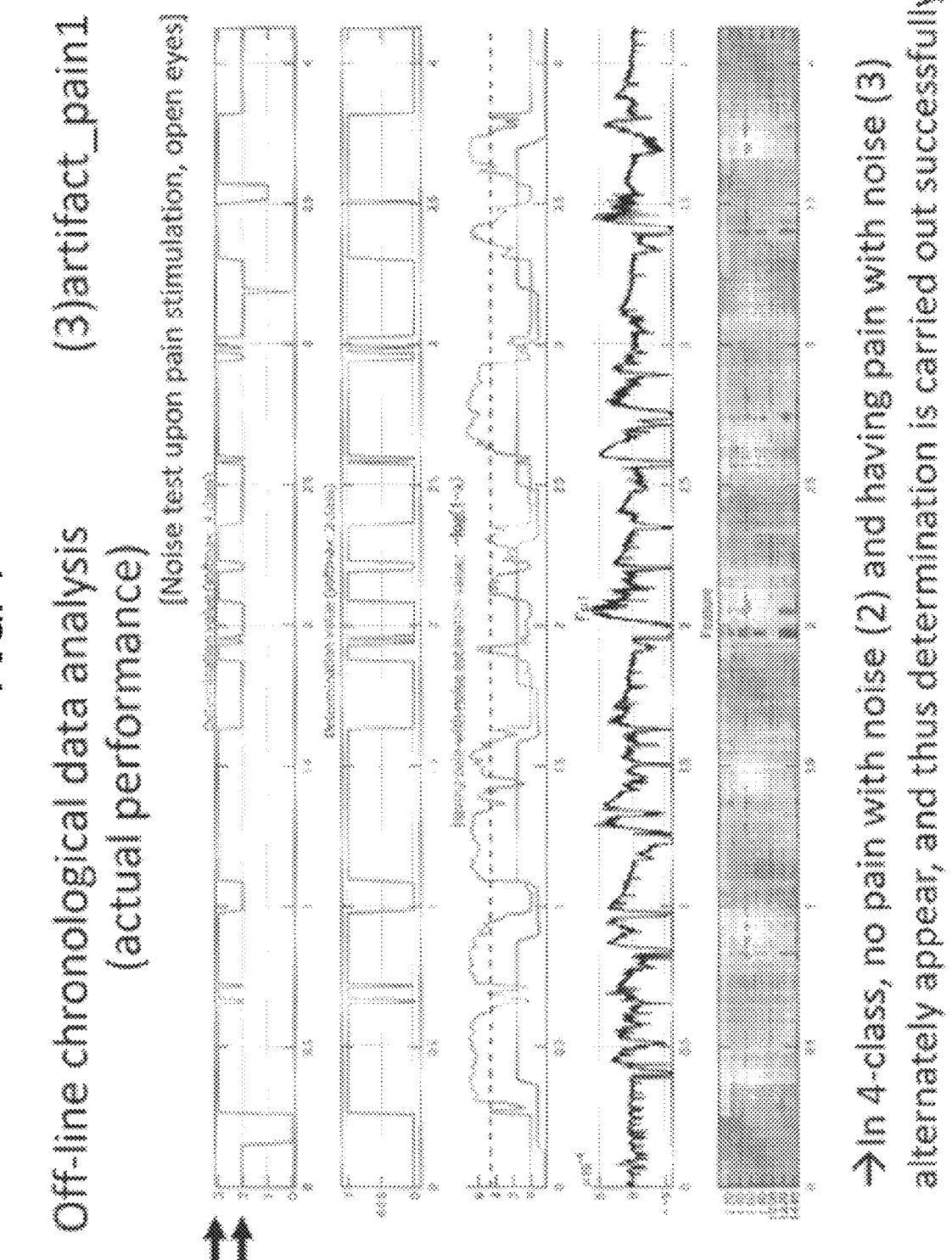
FIG. 7 shows results of performing an off-line chronological data analysis on the raw data shown in FIG. 6. In 4 classes, (2) no pain with noise and (3) having pain with noise appeared alternately; thus, it can be seen that the differentiation was made well.

FIG. 6 shows raw data under artifact_pain1 (noise test upon pain stimulation (voluntary reaction with noise inputted), eyes opened) conditions. FIG. 7 shows an off-line chronological data analysis for model creation. In 4 classes, (2) no pain with noise and (3) having pain with noise appeared alternately; thus, it can be seen that the differentiation was made well.

Figure 8:
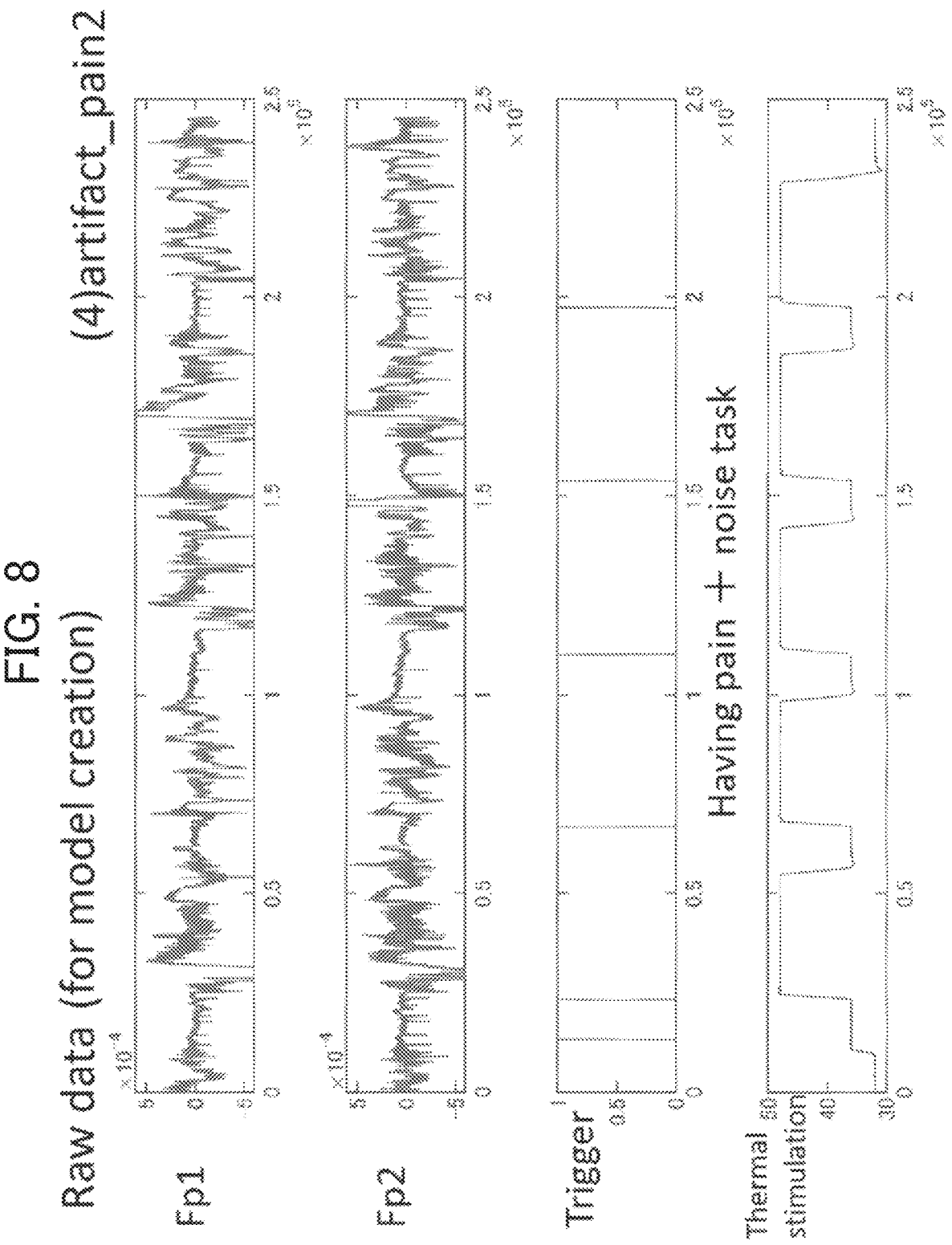
FIG. 8 shows raw data (artifact_pain2) used for 4 class LSTM analysis. The conditions for artifact_pain2 are noise test upon pain stimulation (voluntary reaction with noise inputted), eyes opened.
Figure 9:
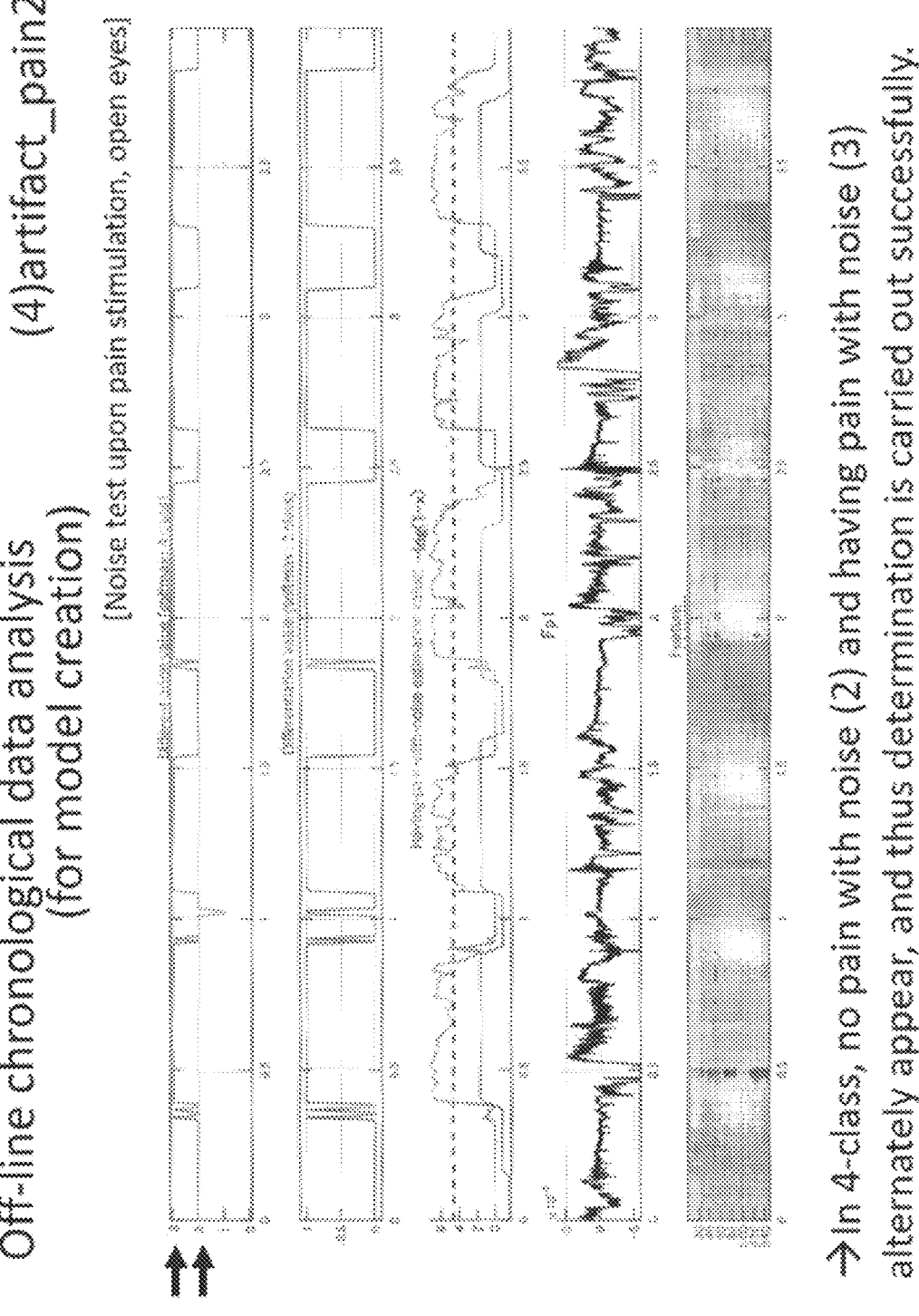
FIG. 9 shows results of performing an off-line chronological data analysis on the raw data show in FIG. 8. In 4 classes, (2) no pain with noise and (3) having pain with noise appeared alternately; thus, it can be seen that the model was created well.

FIG. 8 shows raw data under artifact_pain2 (noise test upon pain stimulation (voluntary reaction with noise inputted), eyes opened) conditions. FIG. 9 shows an off-line chronological data analysis for model creation. In 4 classes, (2) no pain with noise and (3) having pain with noise appeared alternately; thus, it can be seen that the model was created well.

Figure 10:
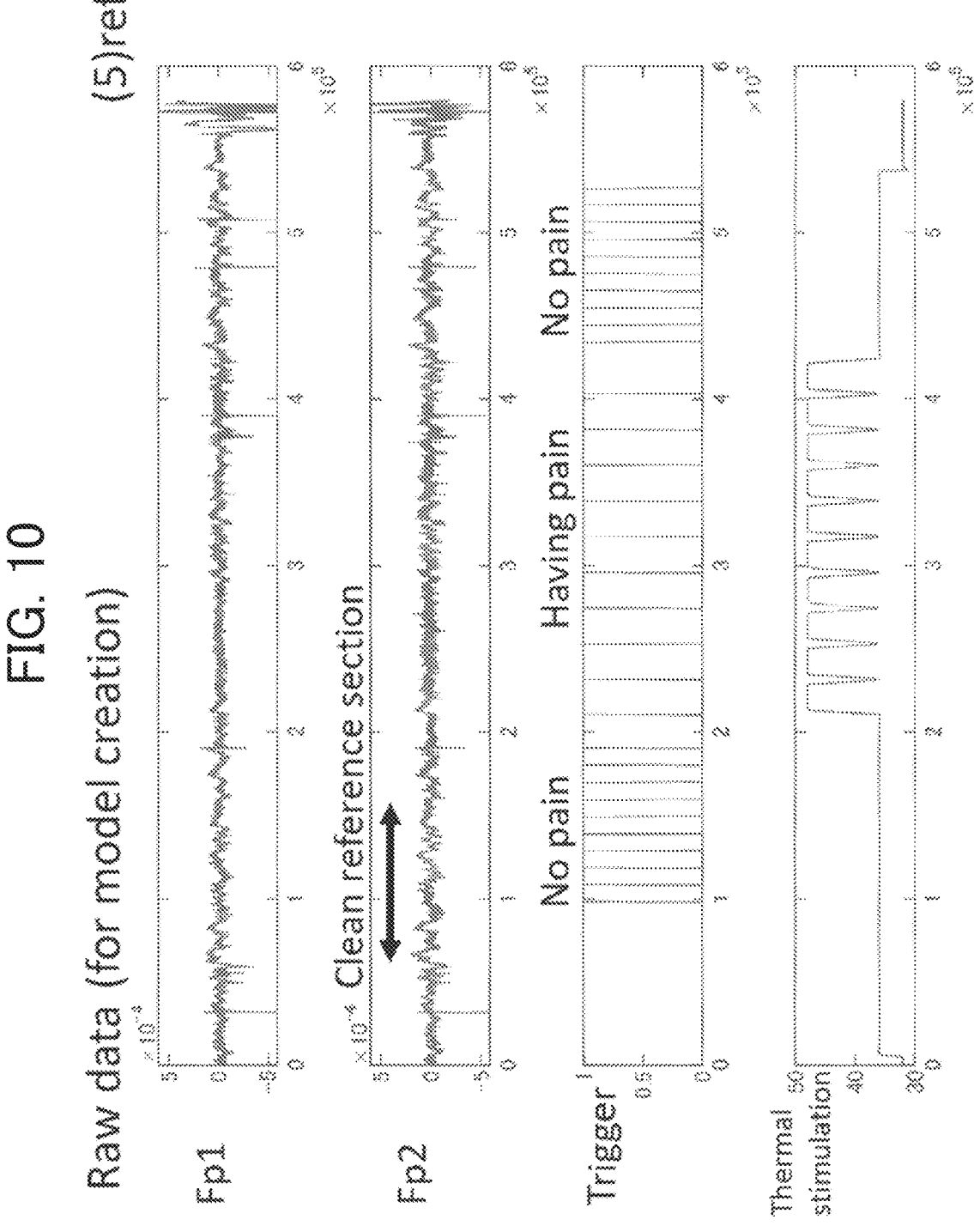
FIG. 10 shows raw data (ref) used for 4 class LSTM analysis. The conditions for ref are pain stimulation, rest, eyes closed.
Figure 11:
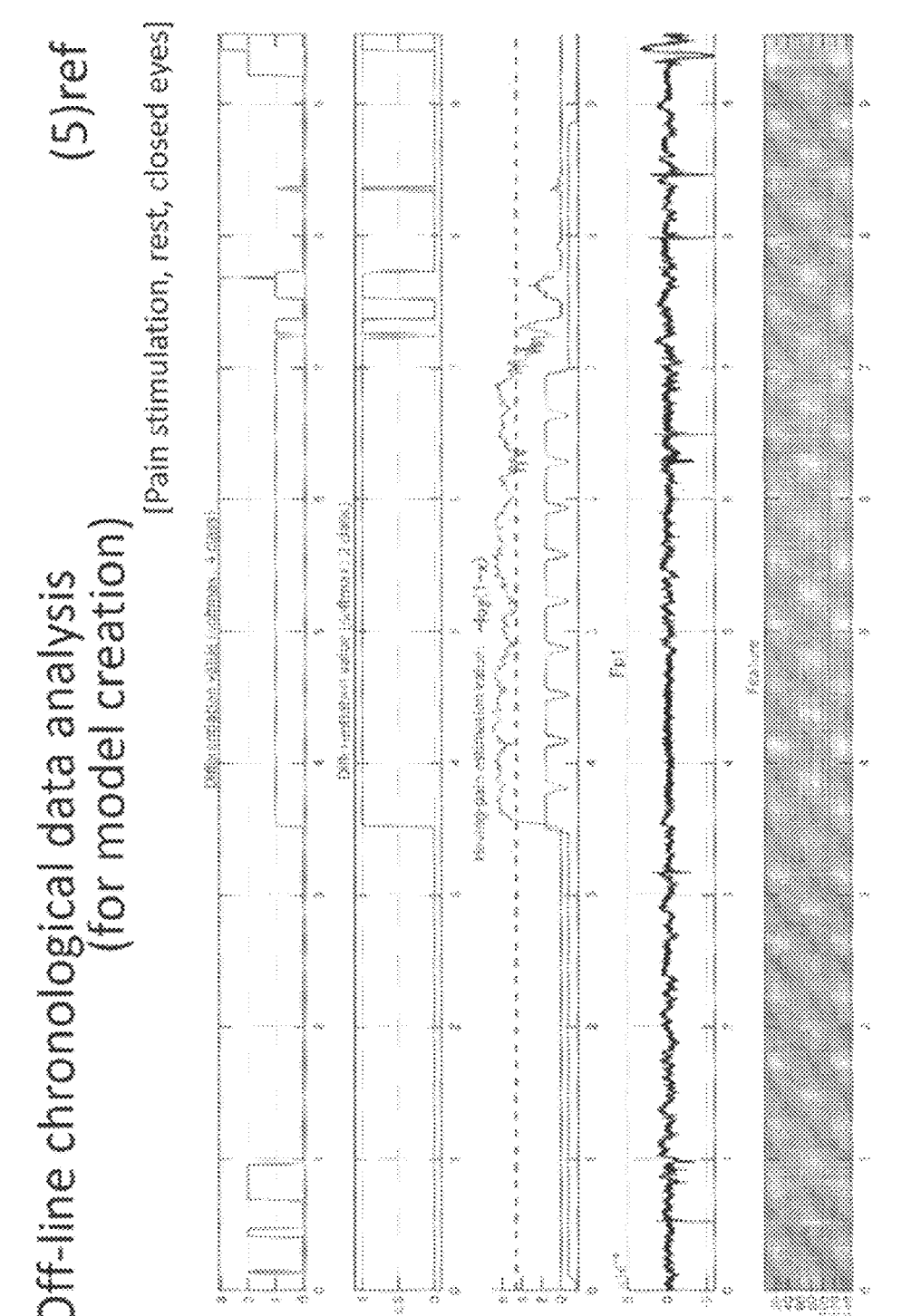
FIG. 11 shows results of performing an off-line chronological data analysis on the raw data shown in FIG. 10. In 4 classes, (1) having pain with no noise appeared when there was a pain stimulation; thus, it can be seen that the model was created well.

FIG. 10 shows raw data under ref (pain stimulation, rest, eyes closed) conditions. FIG. 11 shows an off-line chronological data analysis for model creation. In 4 classes, (1) having pain with no noise appeared when there was a pain stimulation; thus, it can be seen that the model was created well.

Figure 12:
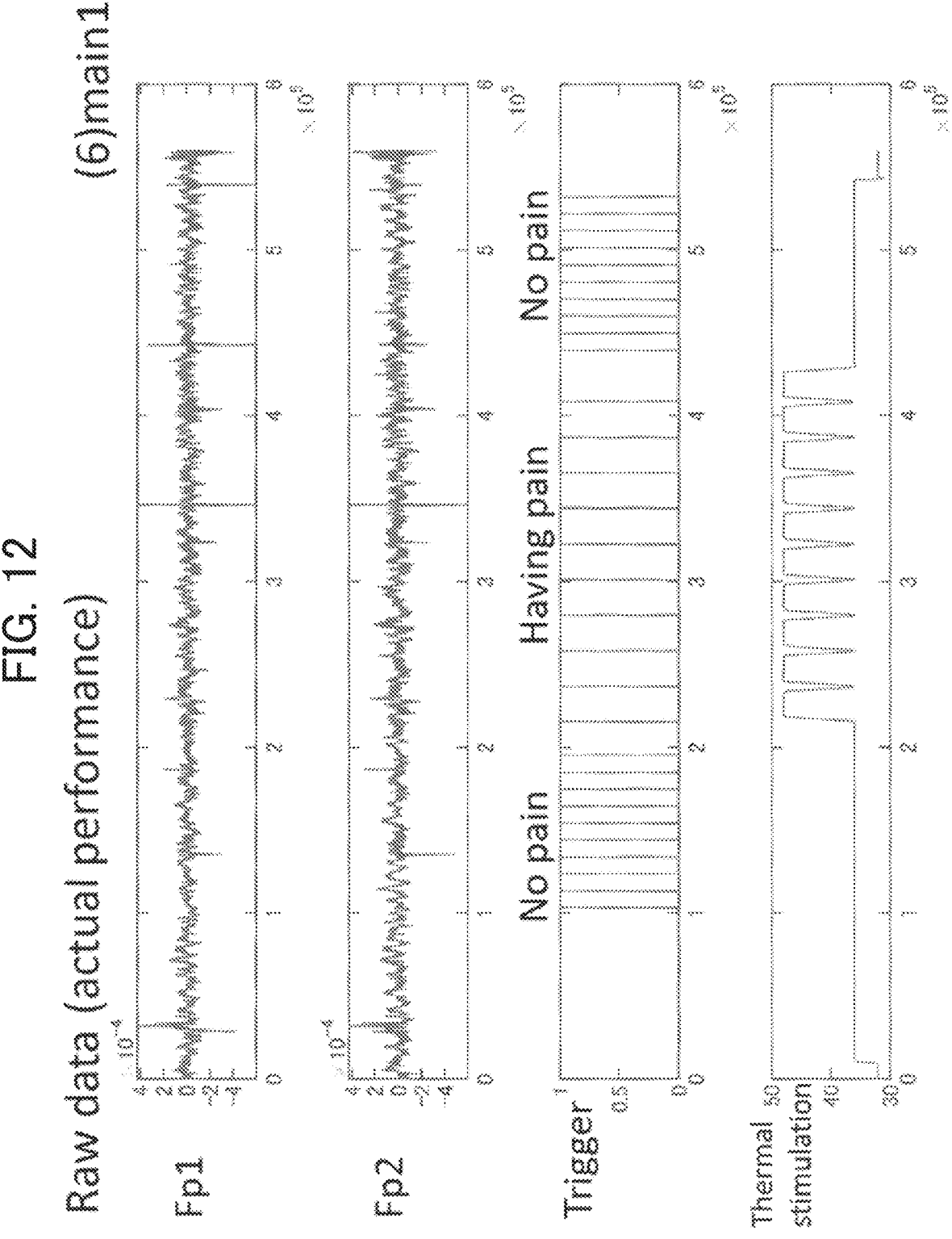
FIG. 12 shows raw data (main1) used for 4 class LSTM analysis. The conditions for main1 are pain stimulation, rest, eyes closed.
Figure 13:
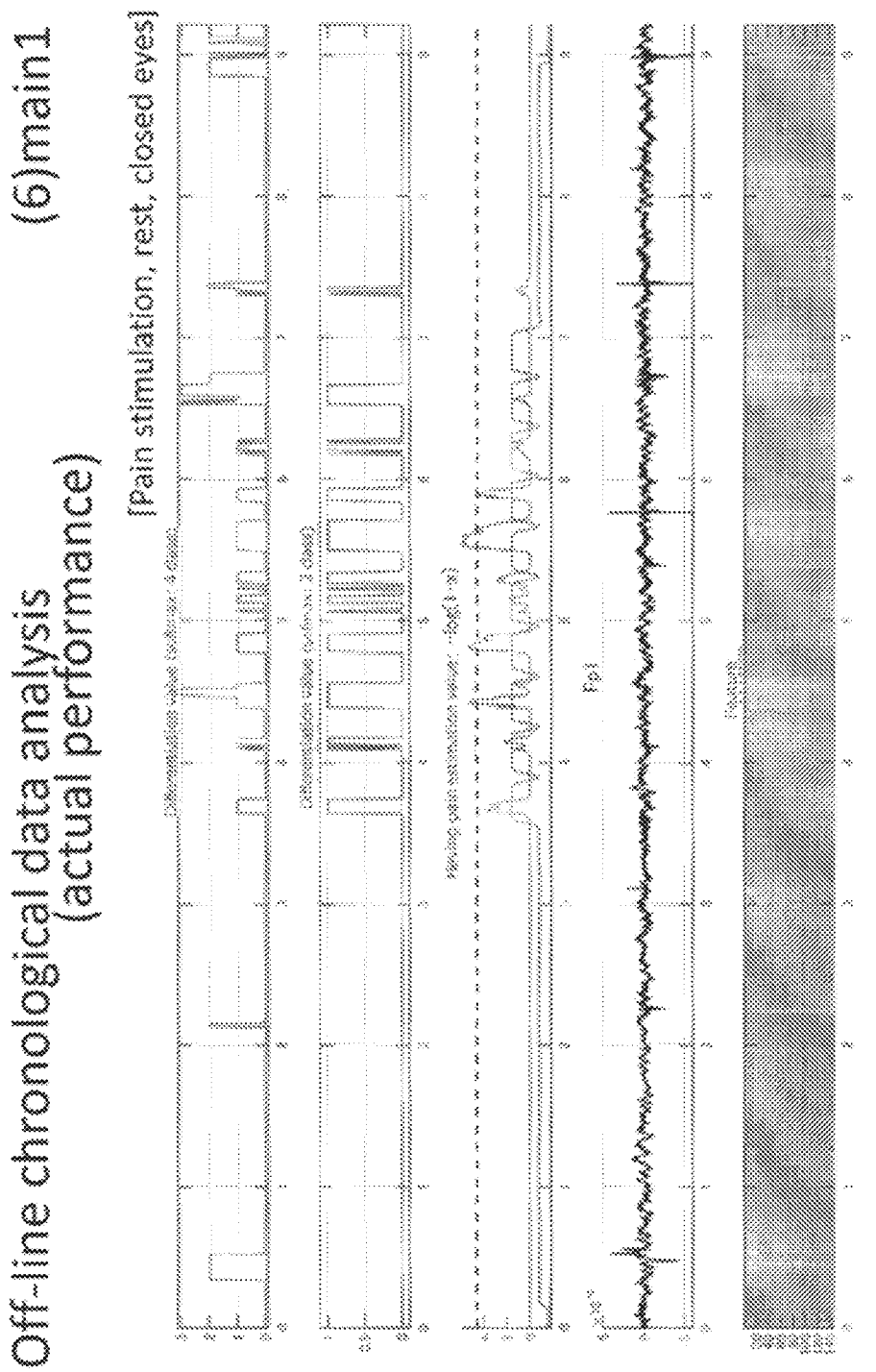
FIG. 13 shows results of performing an off-line chronological data analysis on the raw data shown in FIG. 12. In 4 classes, (1) having pain with no noise appeared when there was a pain stimulation; thus, it can be seen that the differentiation was made well.

FIG. 12 shows raw data under main1 (pain stimulation, rest, eyes closed) conditions. FIG. 13 shows an off-line chronological data analysis for model creation. In 4 classes, (1) having pain with no noise appeared when there was a pain stimulation; thus, it can be seen that the differentiation was made well.

Figure 14:
FIG. 14 shows raw data (main2) used for 4 class LSTM analysis. The conditions for main2 are pain stimulation, rest, eyes closed.
Figure 15:
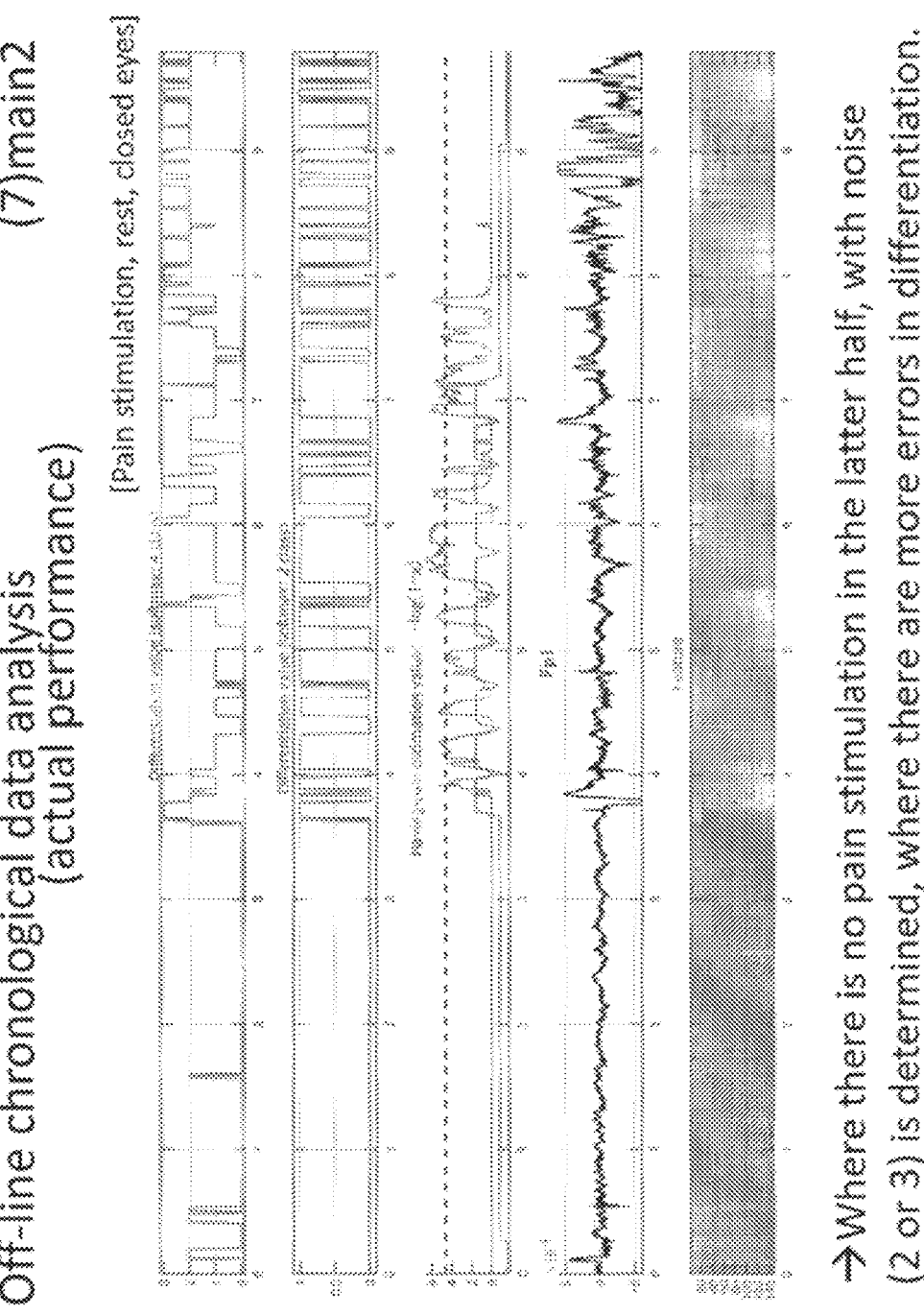
FIG. 15 shows results of performing an off-line chronological data analysis on the raw data show in FIG. 14. Where there was no pain stimulation in the second half, it was determined as with noise (2 or 3), and it can be seen that the number of mis-differentiation increased.

FIG. 14 shows raw data under main2 (pain stimulation, rest, eyes closed) conditions. FIG. 15 shows an off-line chronological data analysis for model creation. Where there was no pain stimulation in the second half, it w s determined as with noise (2 or 3), and it can be seen that the number of mis-differentiation increased. It is conceivable that the cause of the differentiation of the with-noise may have been that the subject was actually moving-his body or that the after-glow after the pain stimulation remained. T at is, it is conceivable that the pain persists and has a lasting effect even after the stimulation is finished.

Figure 16:
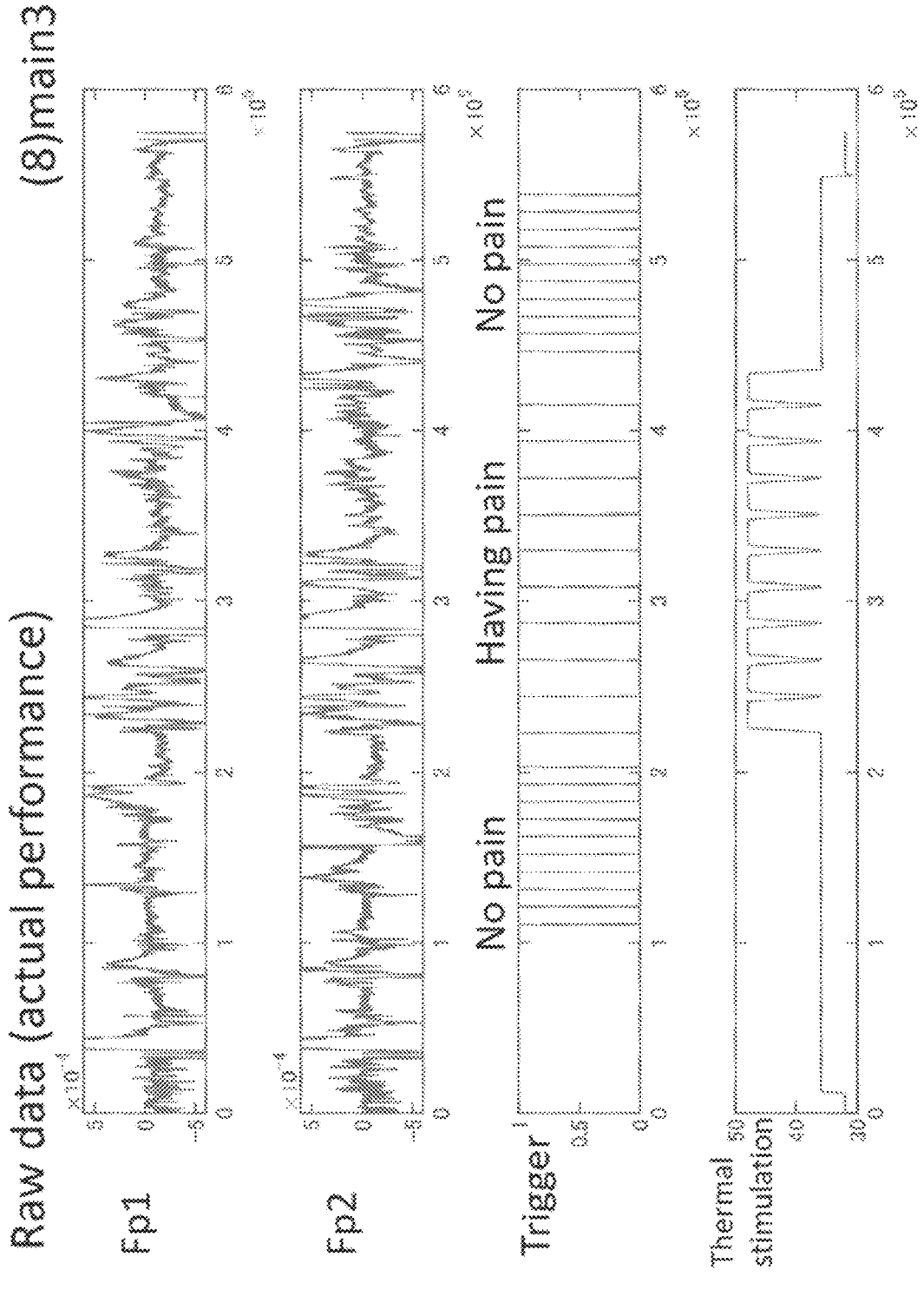
FIG. 16 shows raw data (main3) used for 4 class LSTM analysis. The conditions for main3 are noise test upon pain stimulation, eyes closed.
Figure 17:
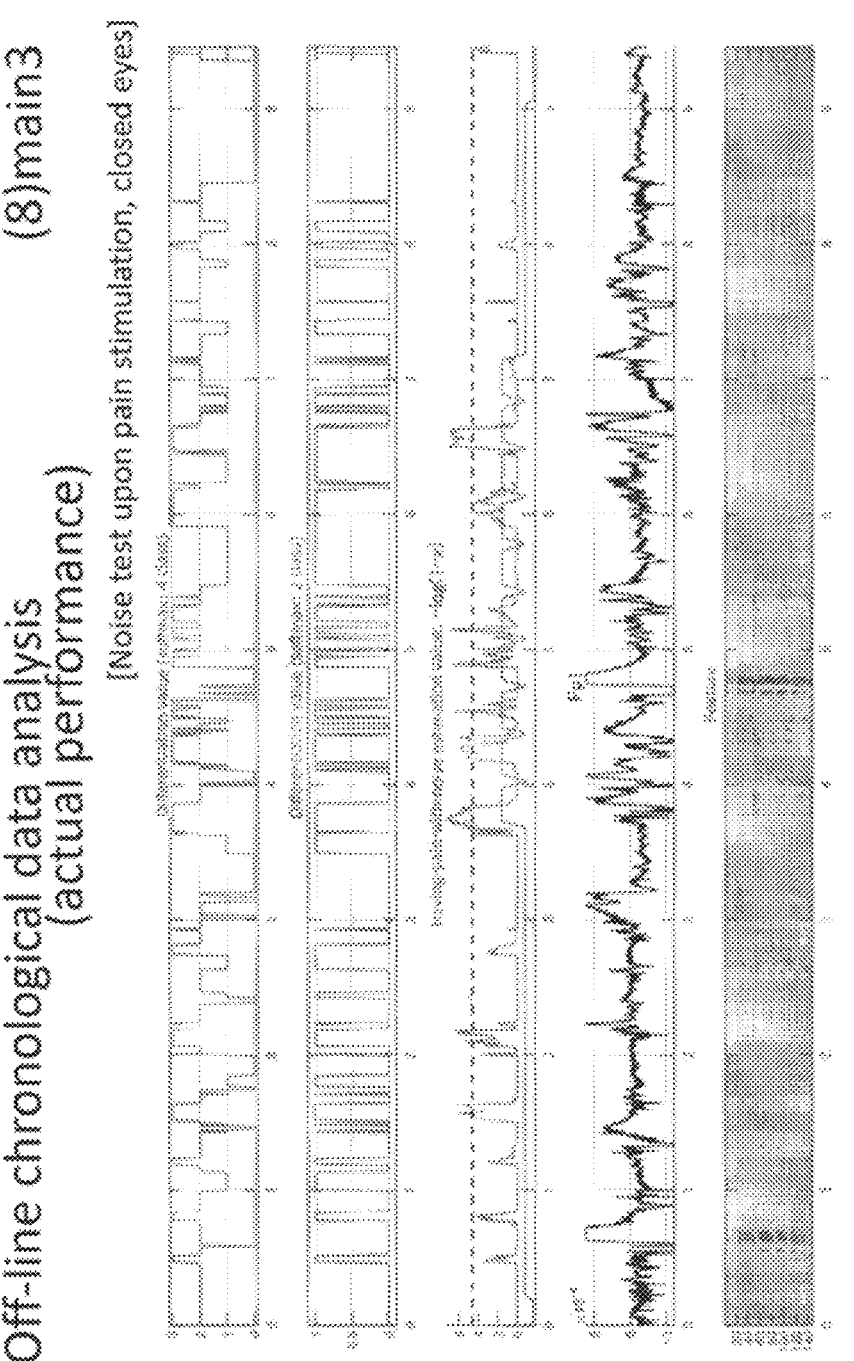
FIG. 17 shows results of performing an off-line chronological data analysis on the raw data shown in FIG. 16. Overall, it was determined as with noise (2 or 3, and it can be seen that the number of mis-differentiation increased in 2 classes.

FIG. 16 shows raw data under main3 (noise test upon pain stimulation, eyes closed) conditions. FIG. 17 shows an off-line chronological data analysis for model creation. Overall, it was determined as with noise (2 or 3), and it can be seen that the number of mis-differentiation increased in 2 classes. It is conceivable that the cause of the differentiation of the with-noise may have been that the subject was actually moving his body. It is conceivable that the cause of the differentiation of the with-noise may have been that the subject was actually moving his body. It is conceivable that the cause of the mis-differentiation of the with-noise even in the first half in the softmax of 2 classes may have been that the model created at this time did not work well.

Figure 18:
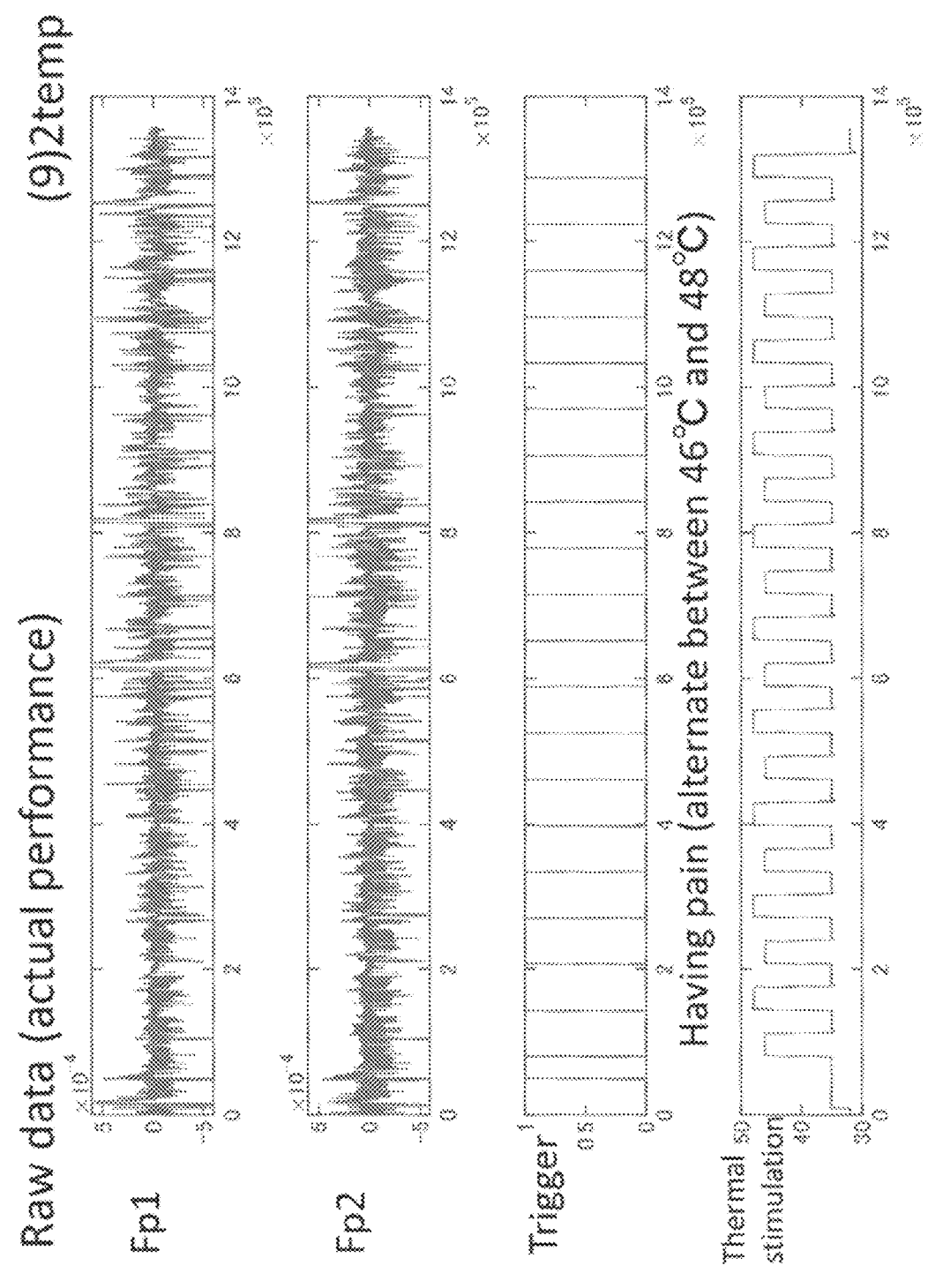
FIG. 18 shows raw data (2temp) used for 4 lass LSTM analysis. The conditions for 2temp are pain stimulation (moderate: 46° C., great: 48° C.), eyes opened.
Figure 19:
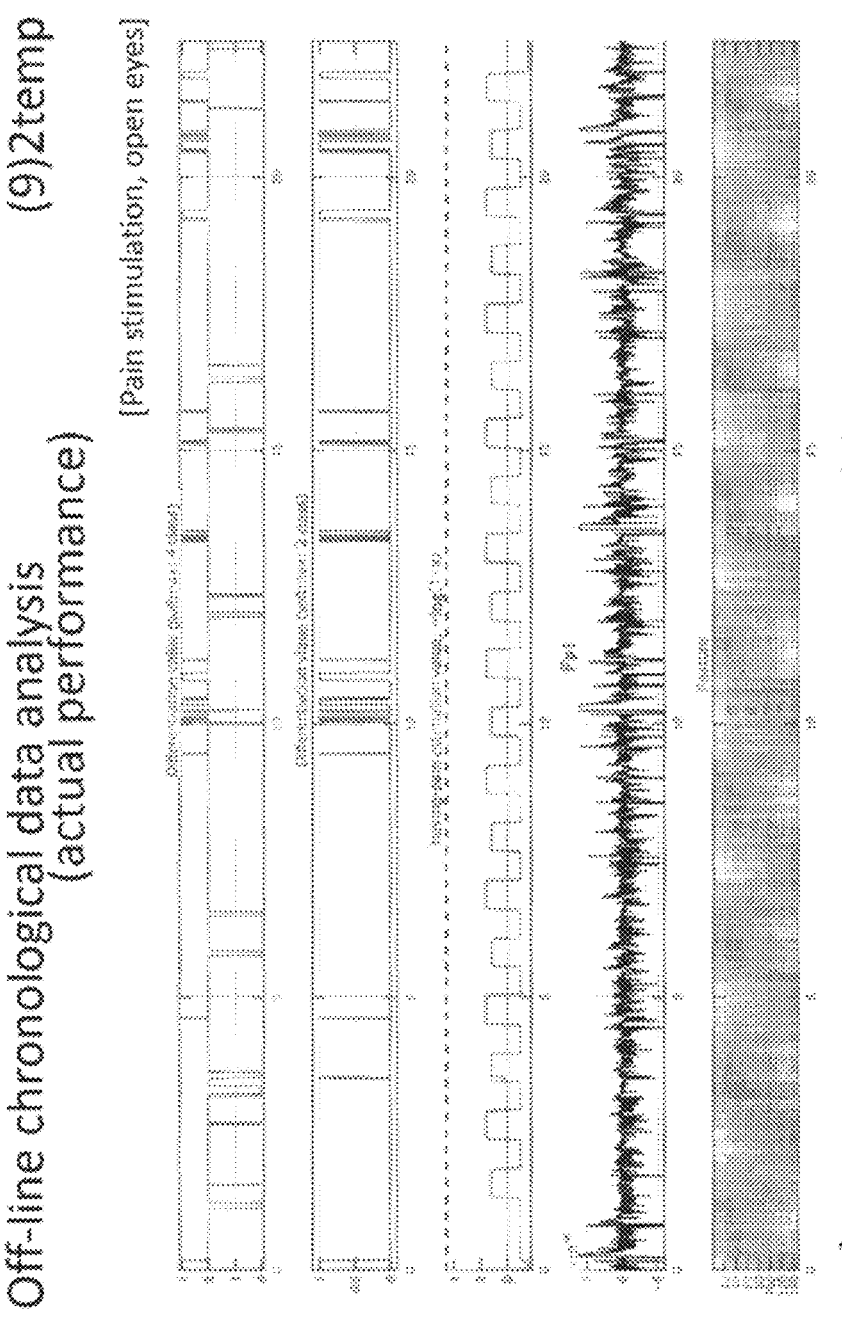
FIG. 19 shows results of performing an off-line chronological data analysis on the raw data show in FIG. 18. Overall, it was determined as with noise (2), and the number of mis-differentiation increased. It is conceivable that this was because no eye-closing task was performed.

FIG. 18 shows raw data under 2temp (pain stimulation (moderate: 46° C., great: 48° C.), eyes opened) conditions. FIG. 19 shows an off-line chronological data analysis for model creation. Overall, it was determined as with noise (2), and the number of mis-differentiation increased. It is conceivable that this was because no eye-closing task was performed.

Figure 20:
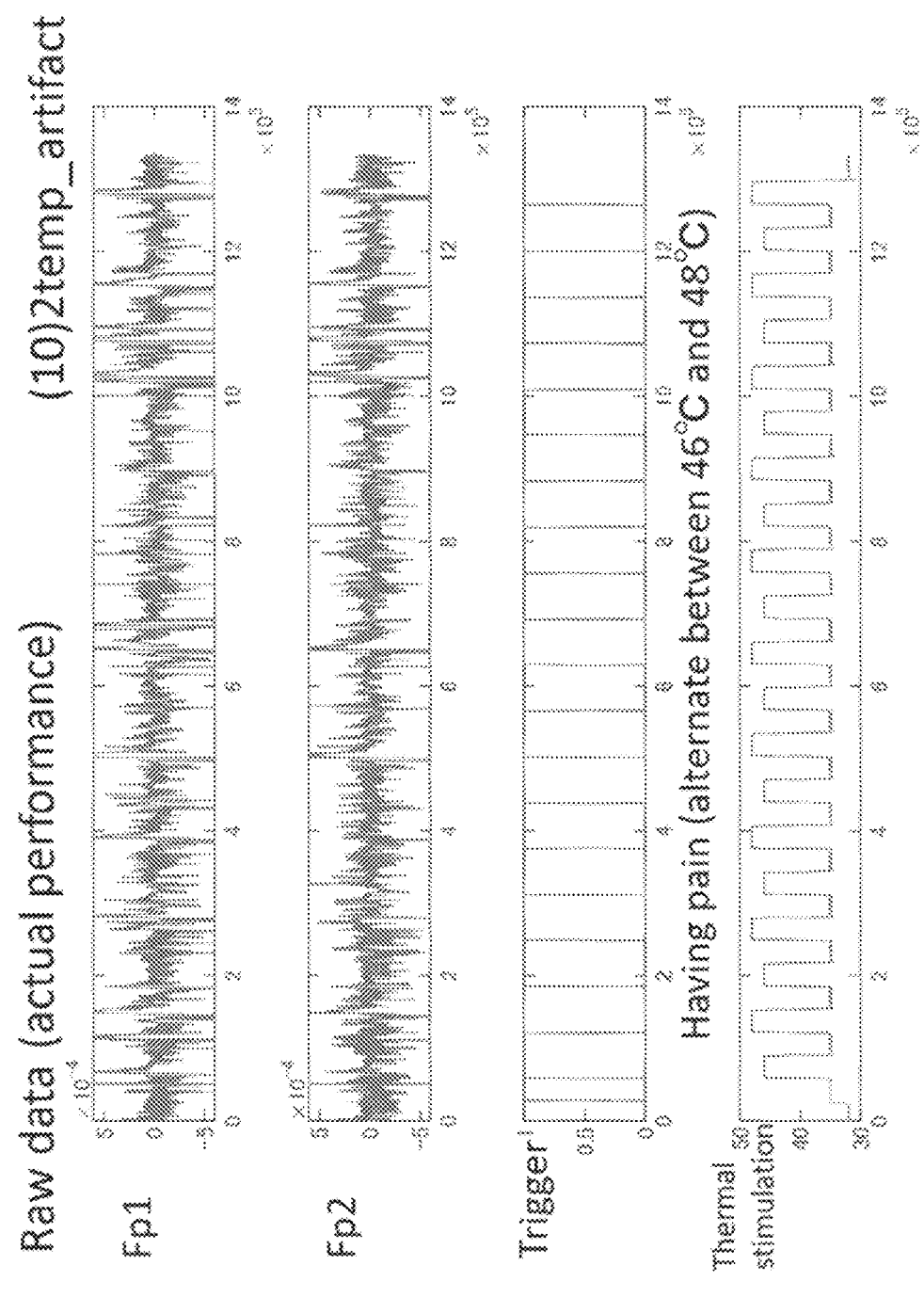
FIG. 20 shows raw data (2temp_artifact) used for 4 class LSTM analysis. The conditions for 2temp_artifact are noise test upon pain stimulation (moderate: 46° C., great: 48° C.) (voluntary reaction with noise inputted), eyes opened.
Figure 23:
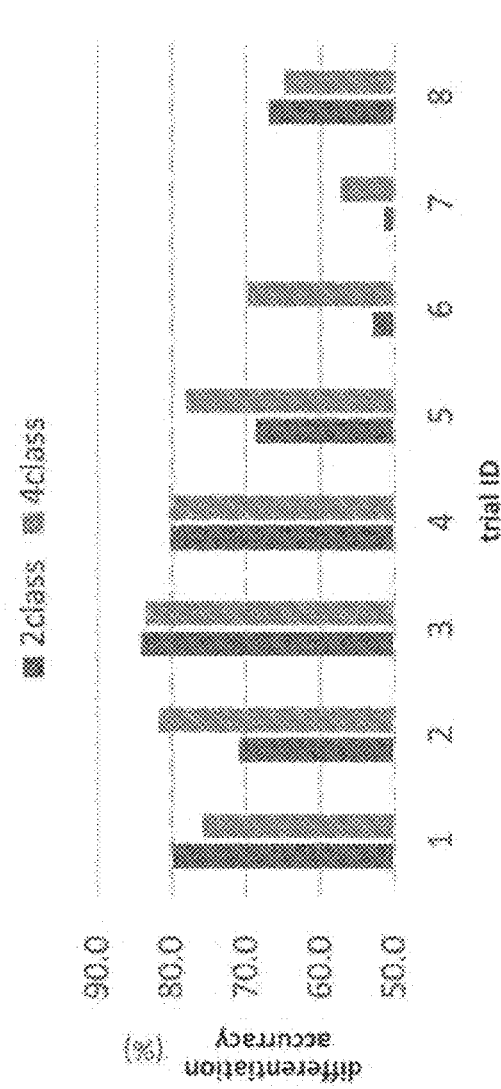
FIG. 23 shows differentiation accuracy in each condition in a comparison of LSTM between 4 classes and 2 classes.
Figure 24:
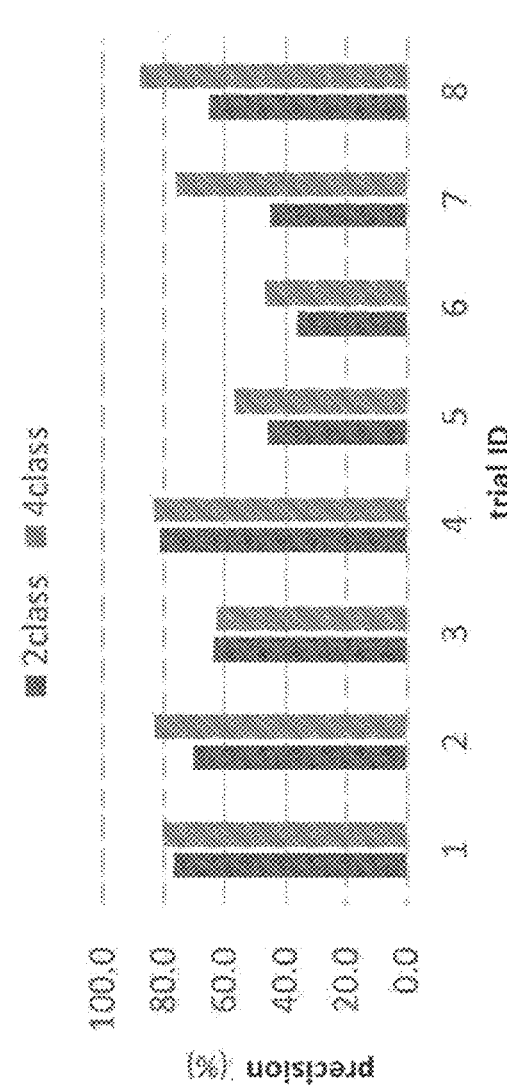
FIG. 24 shows precision in each condition in a comparison of LSTM between 4 classes and 2 classes.
Figure 25:
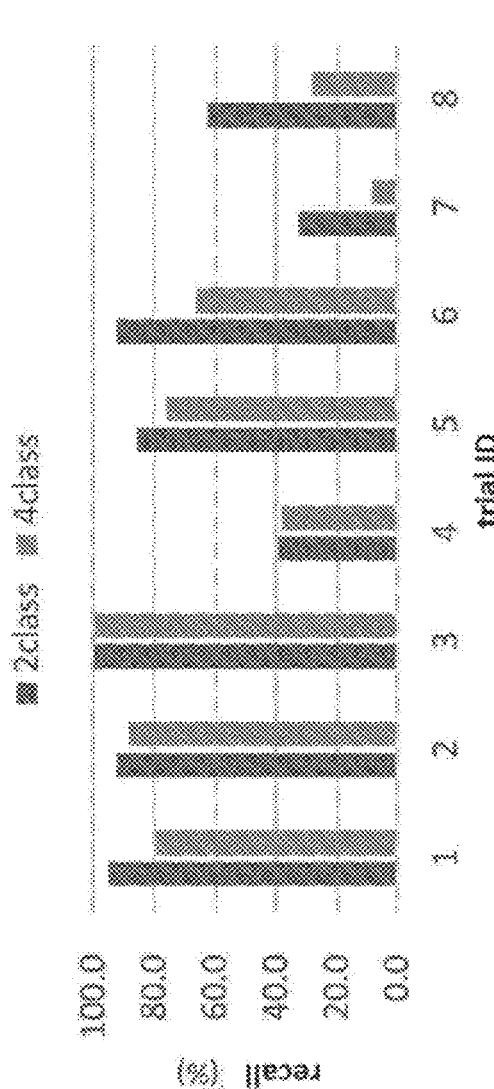
FIG. 25 shows recall in each condition in a comparison of LSTM between 4 classes and 2 classes.
Figure 26:
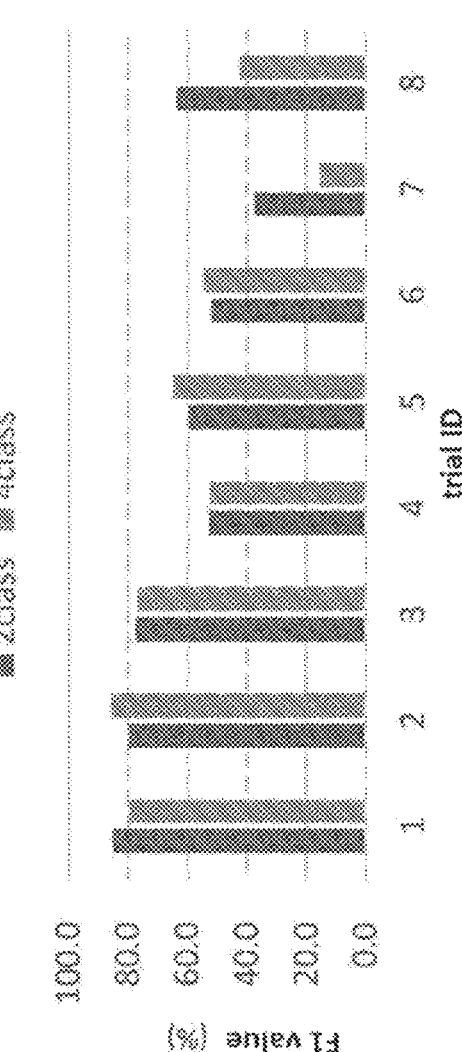
FIG. 26 shows F1 value in each condition in a comparison of LSTM between 4 classes and 2 classes.
Figure 27:
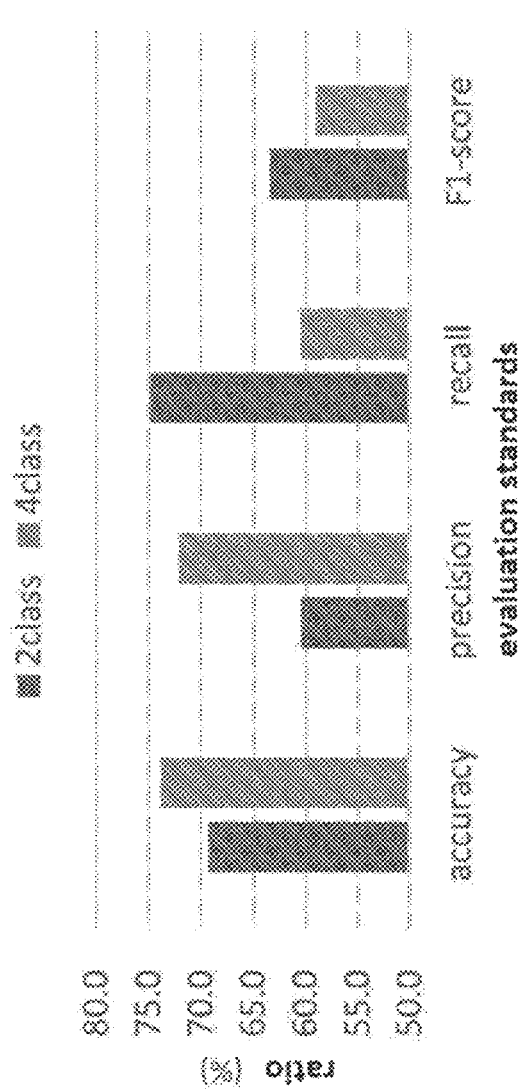
FIG. 27 shows a mean value of evaluation standards in each condition in a comparison of LSTM between 4 classes and 2 classes.

FIG. 20 shows raw data under 2temp artifact (noise test upon pain stimulation (moderate: 46° C., great: 48° C.) (voluntary reaction with noise inputted), eyes opened) conditions. FIG. 21 shows an off-line chronological data analysis for model creation. Although no eye-closing task was performed, a task to respond to pain was performed during pain stimulation. Thus, the differentiation accuracy was improved a little.
(Observation)

From these results, the addition of the no-pain-with-noise class and the having-pain-with-noise class suggested the possibilities for making differentiation even in the presence of noise, in the LSTM of 4 classes.

Example 2

Comparison of 4-Class and 2-Class LSTMs

In this example, a comparison was made between the four-class LSTM and two-class LSTM.
(Method)

In the two-class classification problem, positive and negative, the classification is performed as follows based on the prediction result of the classifier and the rue result. For example, the number of data that was truly positive and the prediction result was also positive was defined as TP (True Positive); the number of data that was truly negative and the prediction result was also negative was defined as TN Substitute Specification-Clean (True Negative); the number of data that was truly negative and the prediction result was positive was defined as FP (False Positive); and the number of data that was truly positive and the prediction result was negative was defined as FN (False Negative).
(Evaluation Standards)

Hereinafter, the four evaluation standards are defined as follows (FIG. 22):

accuracy (accuracy rate, accuracy): percentage of data that were predicted to be positive or negative and that are actually the case $$accuracy=(TP+TN)/(TP+FP+TN+FN)$$

precision (precision): percentage of data t at were predicted to be positive and that are actually positive $$precision=TP/(TP+FP)$$

recall (recall, sensitiveness, sensitivity): percentage of those that are actually positive and that were predicted to be positive $$recall=TP/(TP+FN)$$

F1 value (F1 scale, F1-score, F1-measure): harmonic mean of accuracy and recall $$F1\text{-}score=2*recall*precision/(recall+precision)$$

(Results)

FIGS. 23 to 27 show differentiation accuracy.
(Observation)

The addition of the no-pain-with-noise class and the having-pain-with-noise class suggested the possibilities for making differentiation even in the presence of noise, in the LSTM of 4 classes.

It is conceivable that the reason why the differentiation accuracy was low in (9) 2temp and (10) 2temp_artifact was because no eye-closing task was performed.

For the subjects this time, in terms of the mean value of the evaluation standards, the differentiation accuracy and precision were better in the 4 classes than in the 2 classes. On the contrary, the recall and F1 values were better in the 2 classes. When evaluation is made with differentiation accuracy, 4 classes are considered to be superior.

Example 3

2-Class LSTM Analysis

In this example, a 2-class LSTM analysis was performed. FIG. 28 shows a flow of the 2-class LSTM analysis.
(Results)

The results are shown below.

Figure 29:
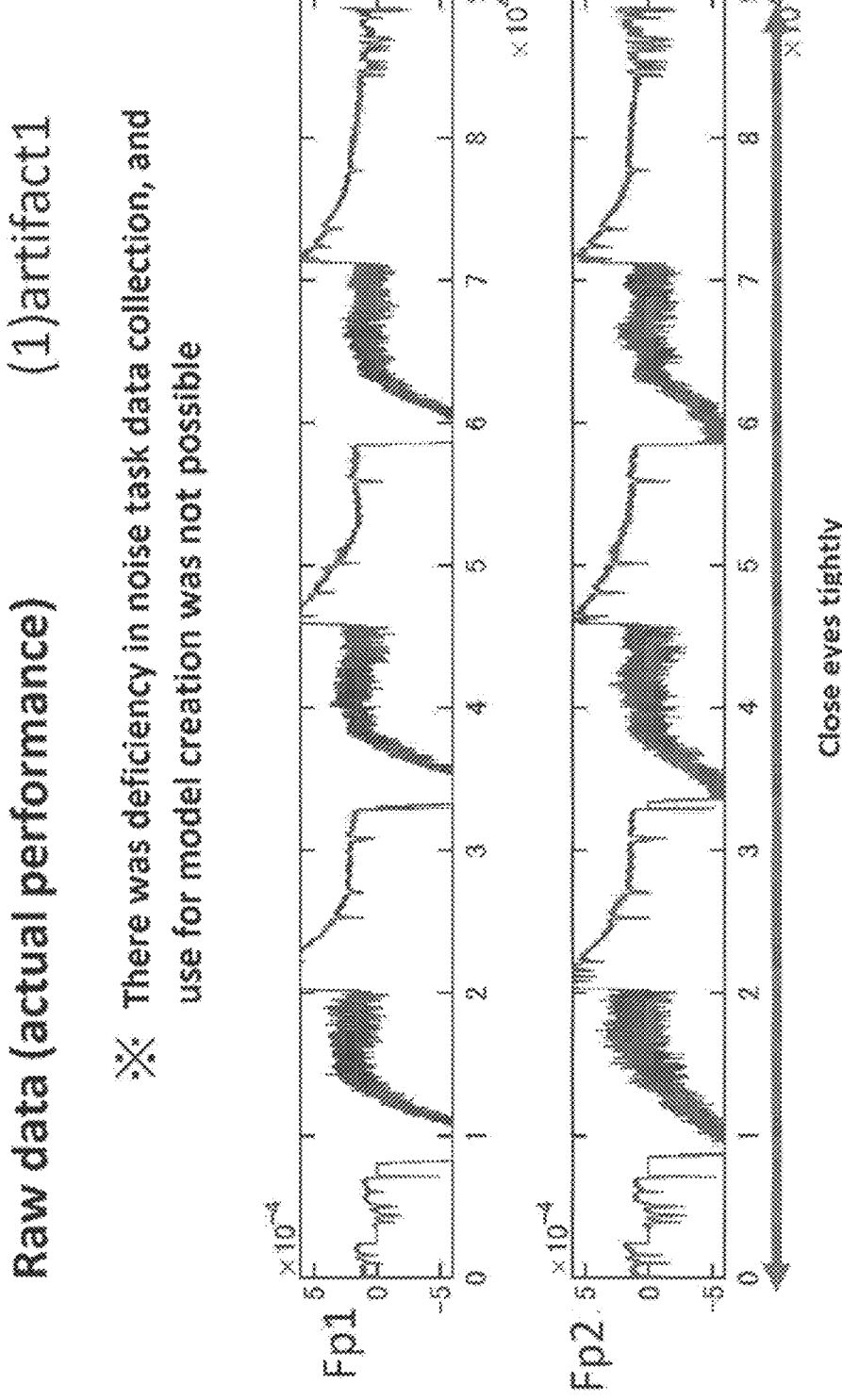
FIG. 29 shows raw data (artifact1) used for 2 class LSTM analysis. The conditions for artifact1 are noise test (tightly closing the eyes, stretching the body, reading out loud), eyes opened. Due to a defect in the data collection of the noise task, model creation based on this data is not performed.
Figure 30:
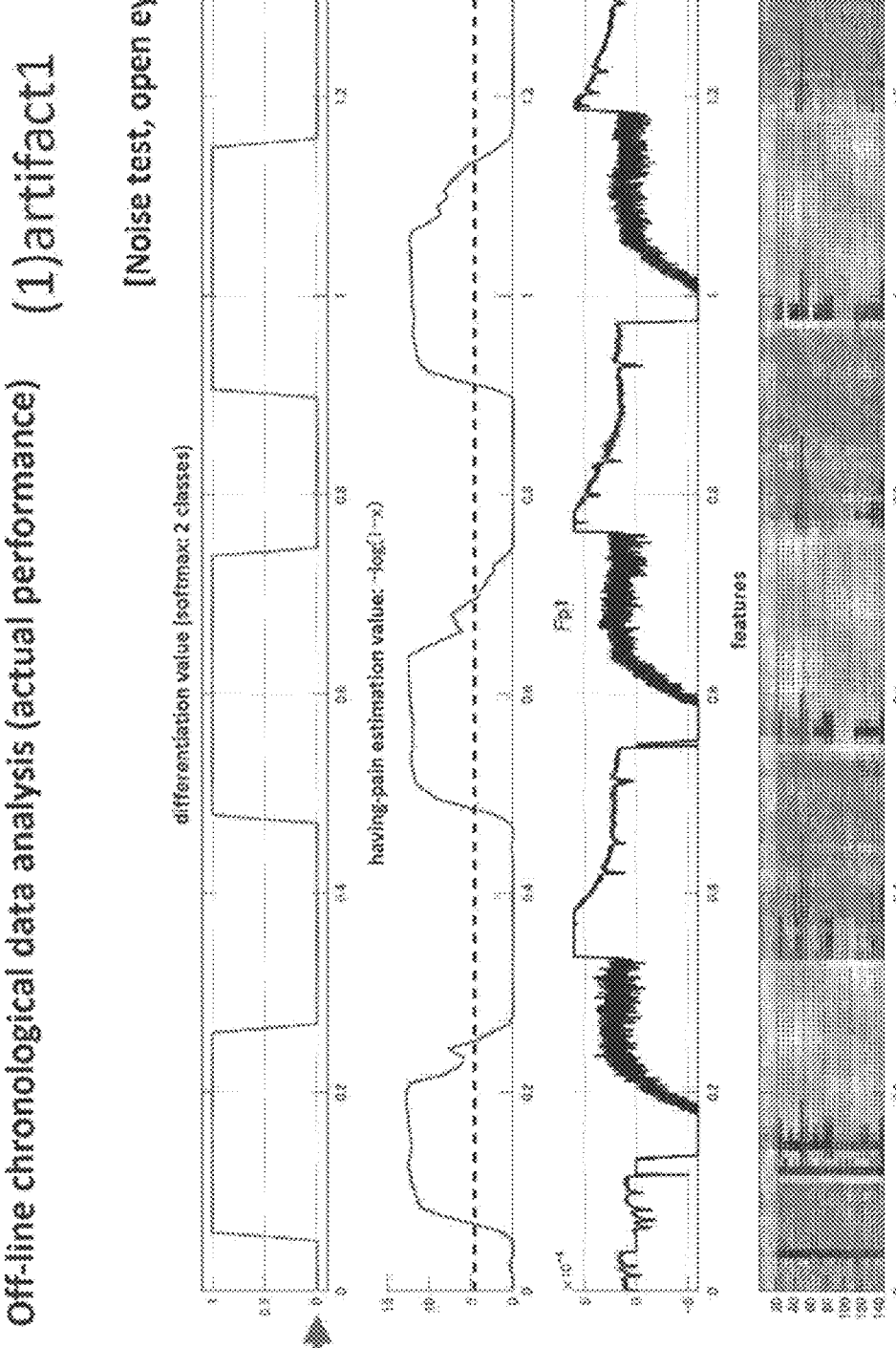
FIG. 30 shows results of performing an off-Line chronological data analysis on the raw data shown in FIG. 29. In 2 classes, it should have been determined as (0) no pain; Substitute Specification-Clean however, mis-differentiation was made.

FIG. 29 shows raw data under artifact1 (noise test (tightly closing the eyes, stretching the body, reading out loud), eyes opened) conditions. FIG. 30 shows the results of performing the off-line chronological data analysis. In 2 classes, it should have been determined as (0) no pain; however, mis-differentiation was made.

Figure 31:
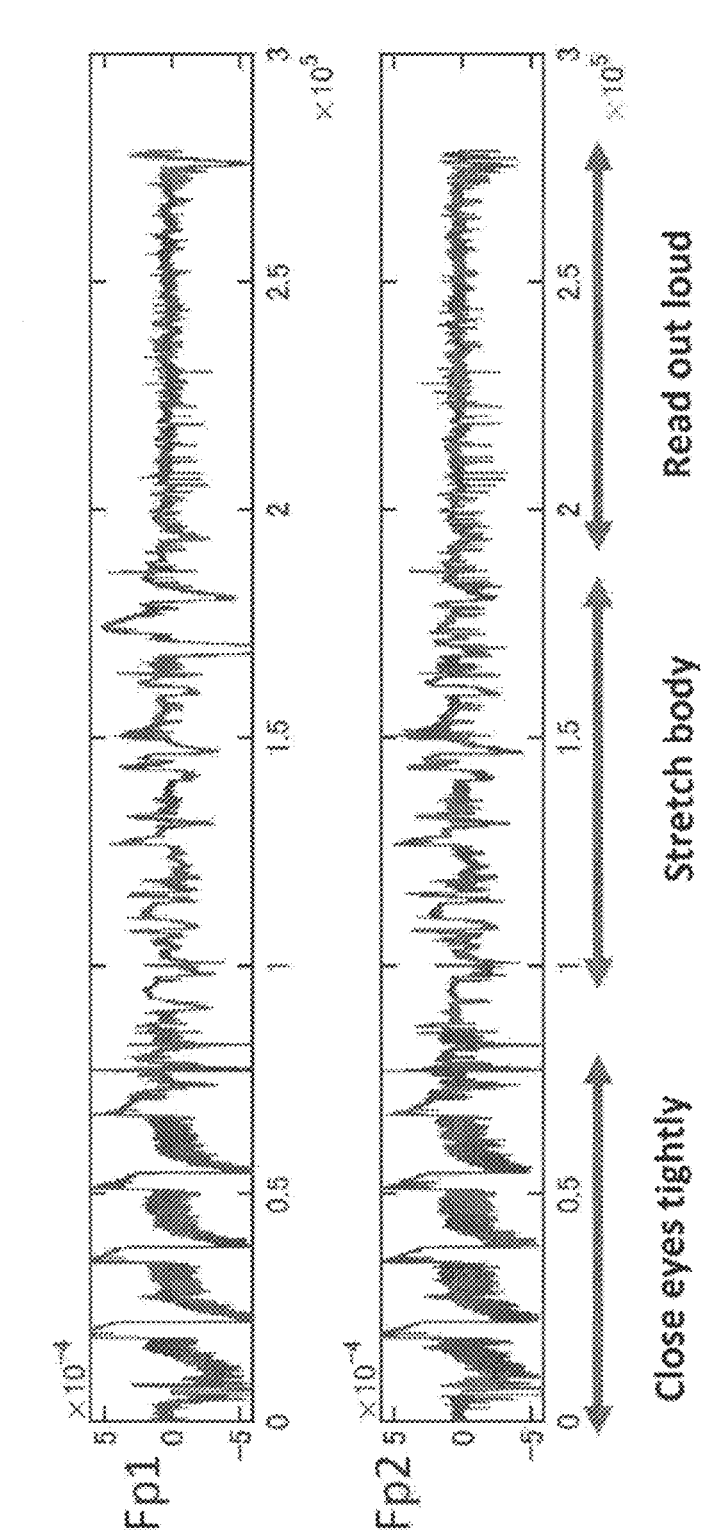
FIG. 31 shows raw data (artifact2) used for 2 class LSTM analysis. The conditions for artifact2 are noise test (tightly closing the eyes, stretching the body, reading out loud), eyes opened.

FIG. 31 shows raw data under artifact2 (noise test (tightly closing the eyes, stretching the body, reading out loud), eyes opened) conditions. FIG. 32 shows an off-line chronological data analysis for model creation. It should have been determined as (0) no pain since the classes were 2 classes; however, mis-differentiation, having pain, was made.

Figure 33:
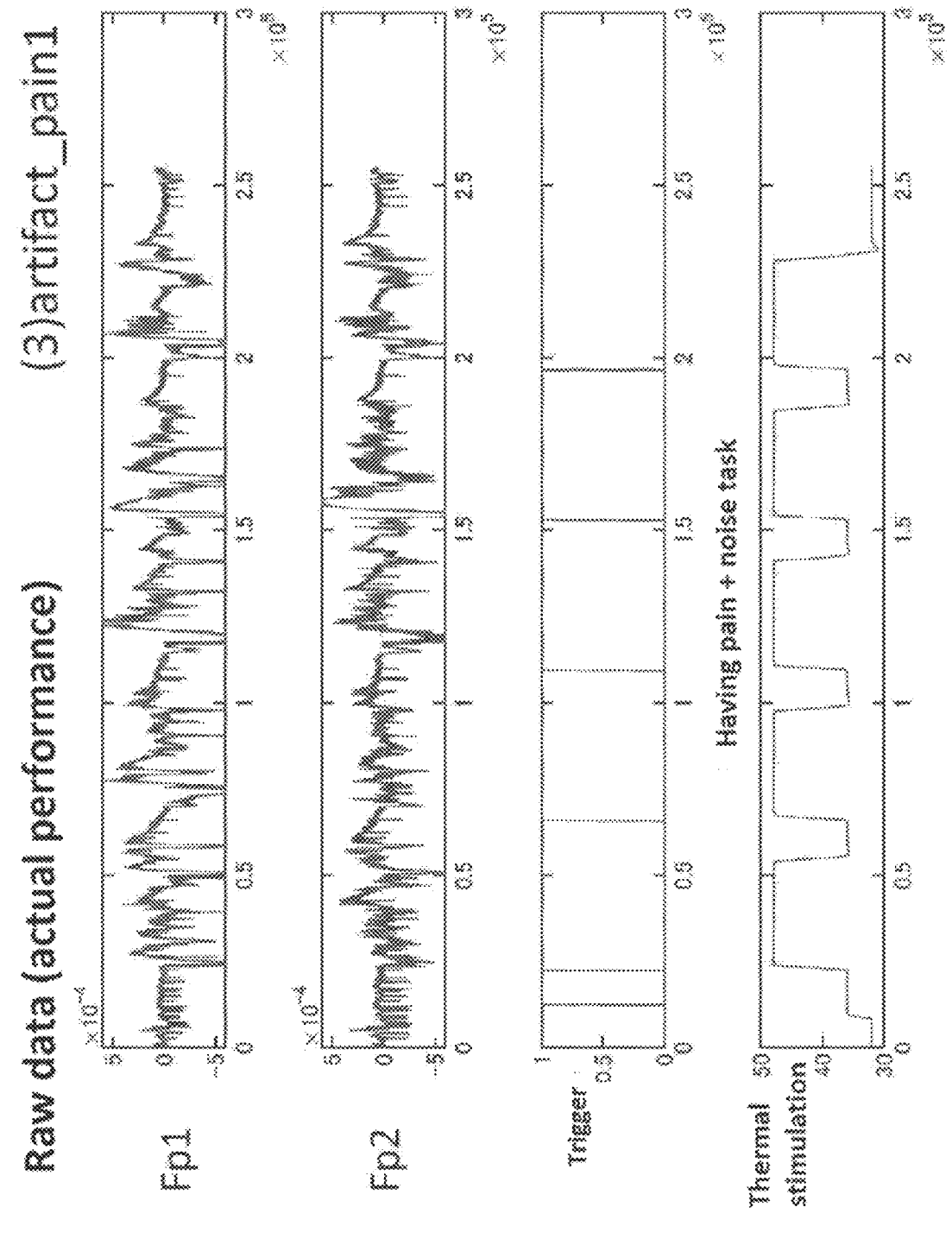
FIG. 33 shows raw data (artifact_pain1) used for 2 class LSTM analysis. The conditions for artifact_pain1 are noise test upon pain stimulation (voluntary reaction with noise inputted), eyes opened.
Figure 34:
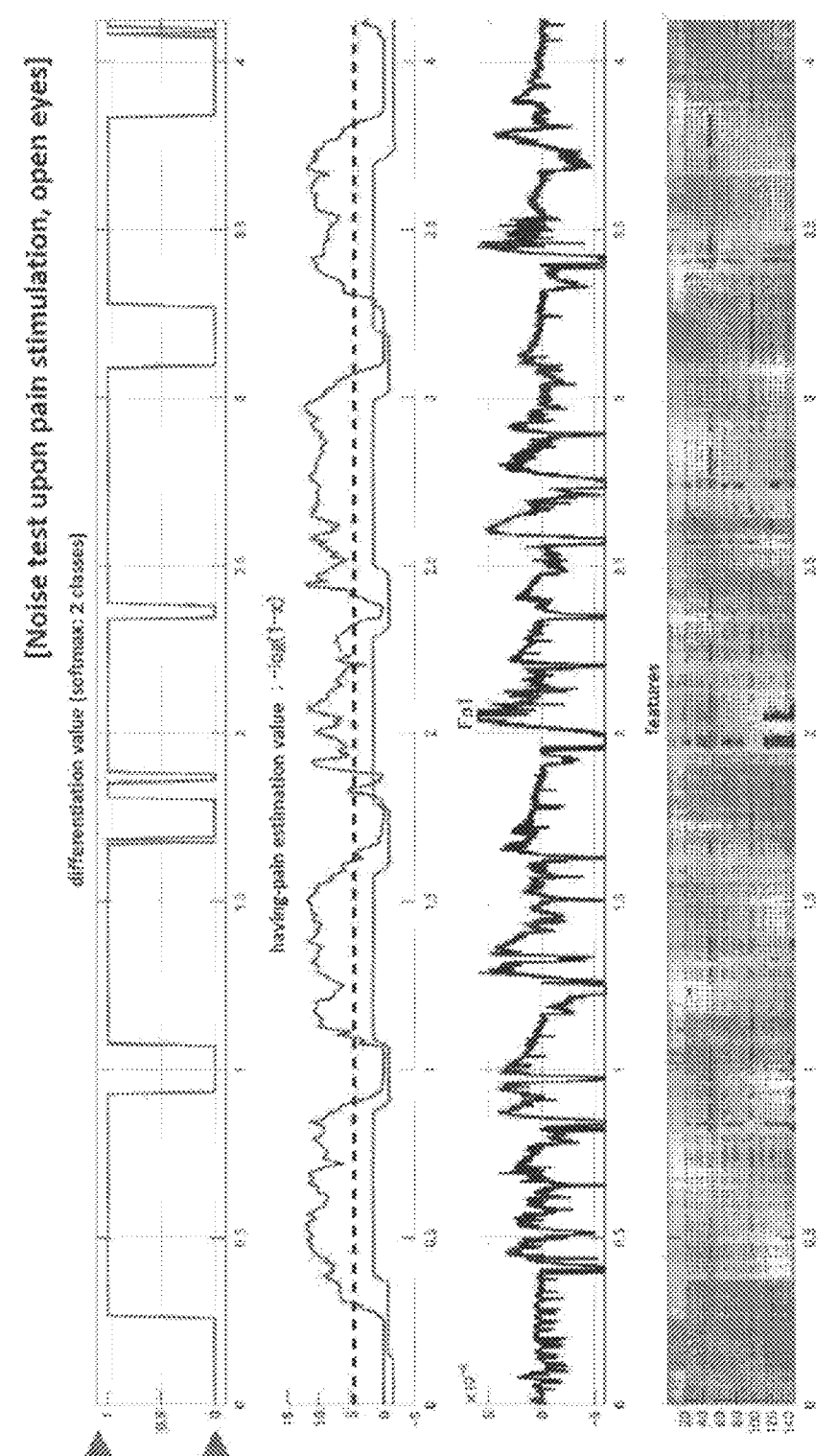
FIG. 34 shows results of performing an off-line chronological data analysis on the raw data shown in FIG. 33. In 2 classes, (0) no pain and (1) having pain appeared alternately; thus, the differentiation was made ell.

FIG. 33 shows raw data under artifact_pain1 (noise test upon pain stimulation (voluntary reaction with noise inputted), eyes opened) conditions. FIG. 34 shows an off-line chronological data analysis for model creation. In 2 classes, Substitute Specification-Clean (0) no pain and (1) having pain appeared alternately; thus, the differentiation was made well.

Figure 35:
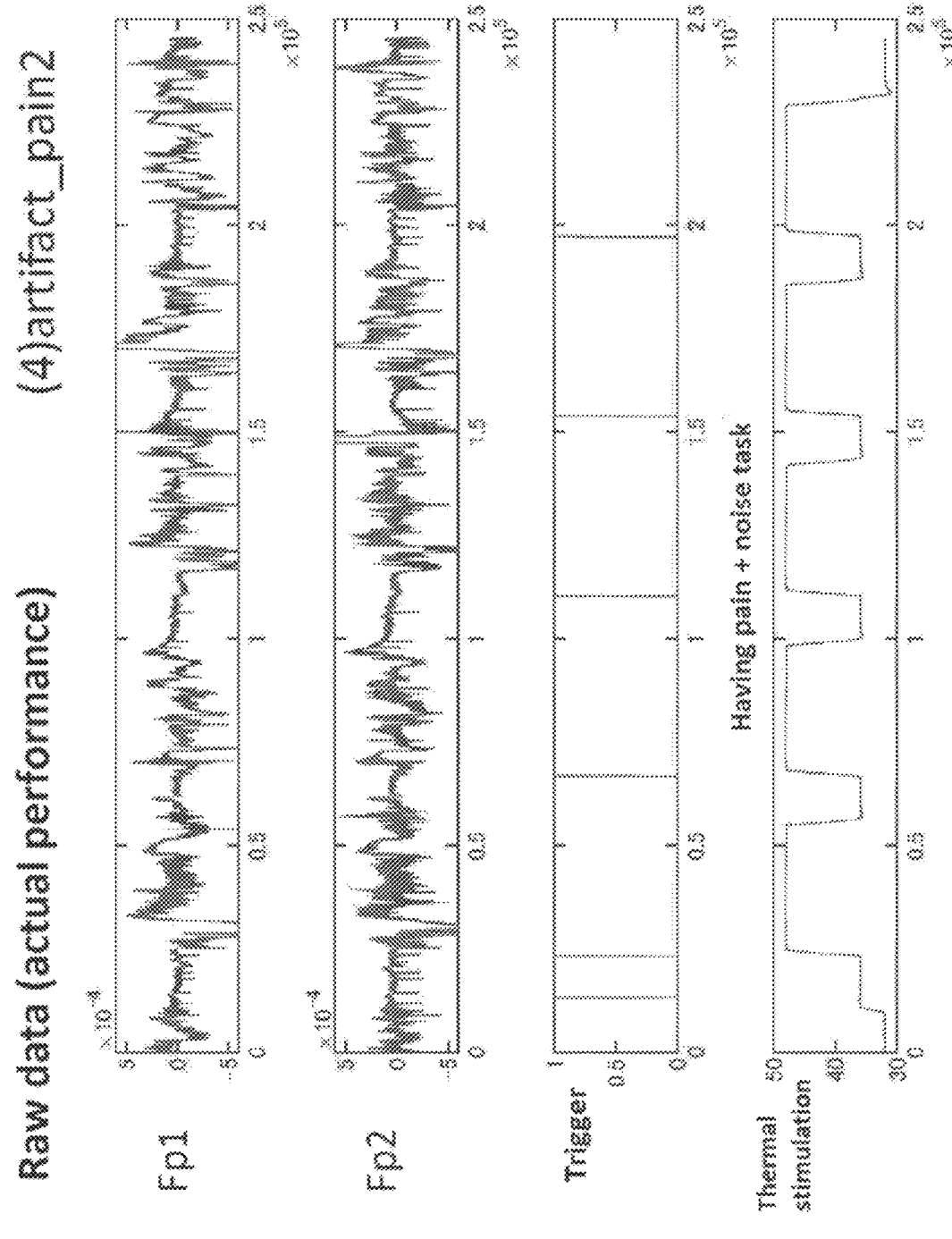
FIG. 35 shows raw data (artifact_pain2) used for 2 class LSTM analysis. The conditions for artifact_pain2 are noise test upon pain stimulation (voluntary reaction with noise inputted), eyes opened.
Figure 36:
FIG. 36 shows results of performing an off-line chronological data analysis on the raw data shown in FIG. 35. In 2 classes, (0) no pain and (1) with noise appeared alternately; thus, the differentiation was made well.

FIG. 35 shows raw data under artifact_pain2 (noise test upon pain stimulation (voluntary reaction with noise inputted), eyes opened) conditions. FIG. 36 shows an off-line chronological data analysis for model creation. In 2 classes, (0) no pain and (1) with noise appeared alternately; thus, the differentiation was made well.

Figure 37:
FIG. 37 shows raw data (ref) used for 2 class LSTM analysis. The conditions for ref are pain stimulation, rest, eyes closed.
Figure 38:
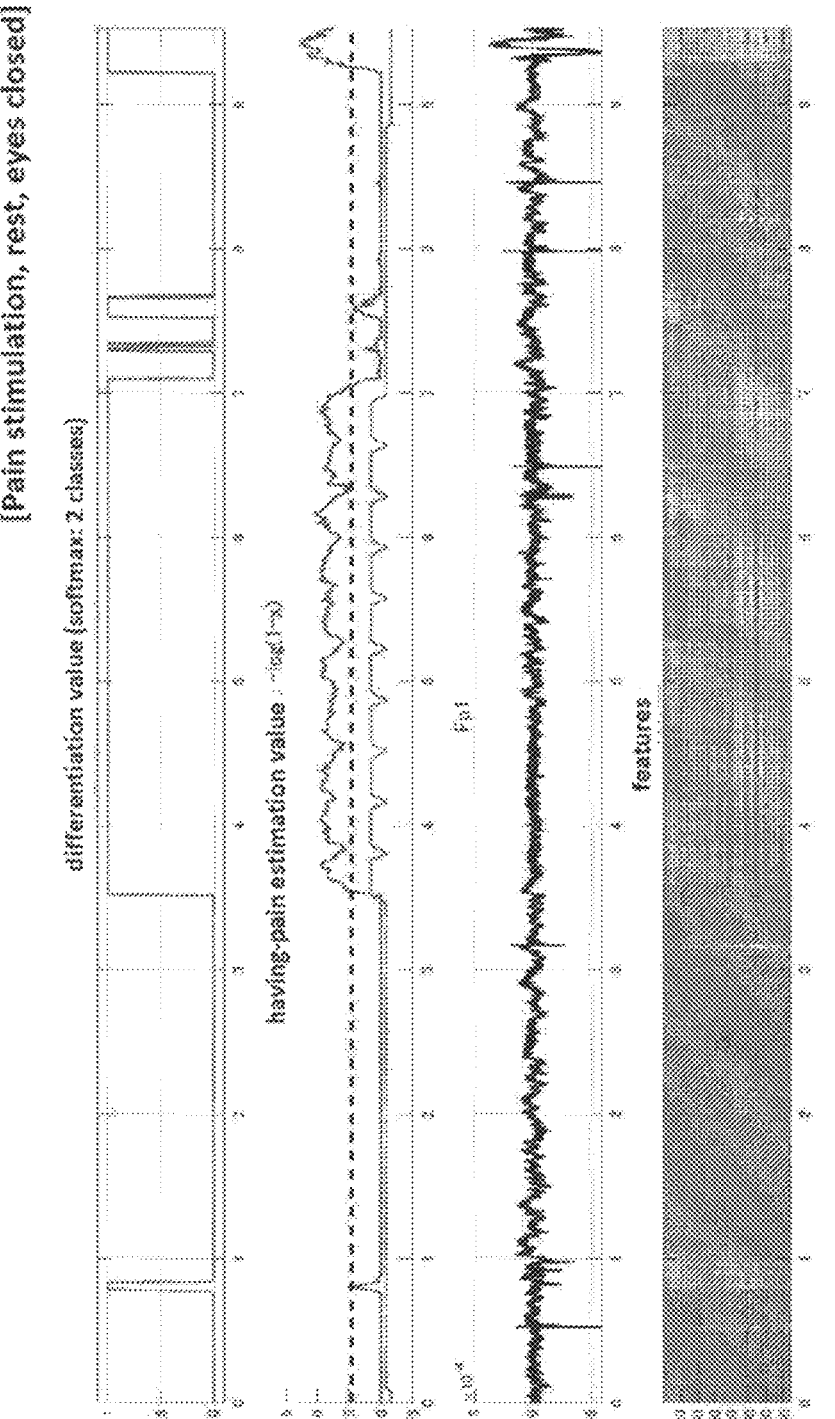
FIG. 38 shows results of performing an off-line chronological data analysis on the raw data show in FIG. 37. In 2 classes, (1) having pain appeared when there was a pain stimulation; thus, the model was created well.

FIG. 37 shows raw data under ref (pain stimulation, rest, eyes closed) conditions. FIG. 38 shows an off-lire chronological data analysis for model creation. En 2 classes, (1) having pain appeared when there was a pain stimulation; thus, the model was created well.

Figure 39:
FIG. 39 shows raw data (main1) used for 2 class LSTM analysis. The conditions for main1 are pain stimulation, rest, eyes closed.
Figure 40:
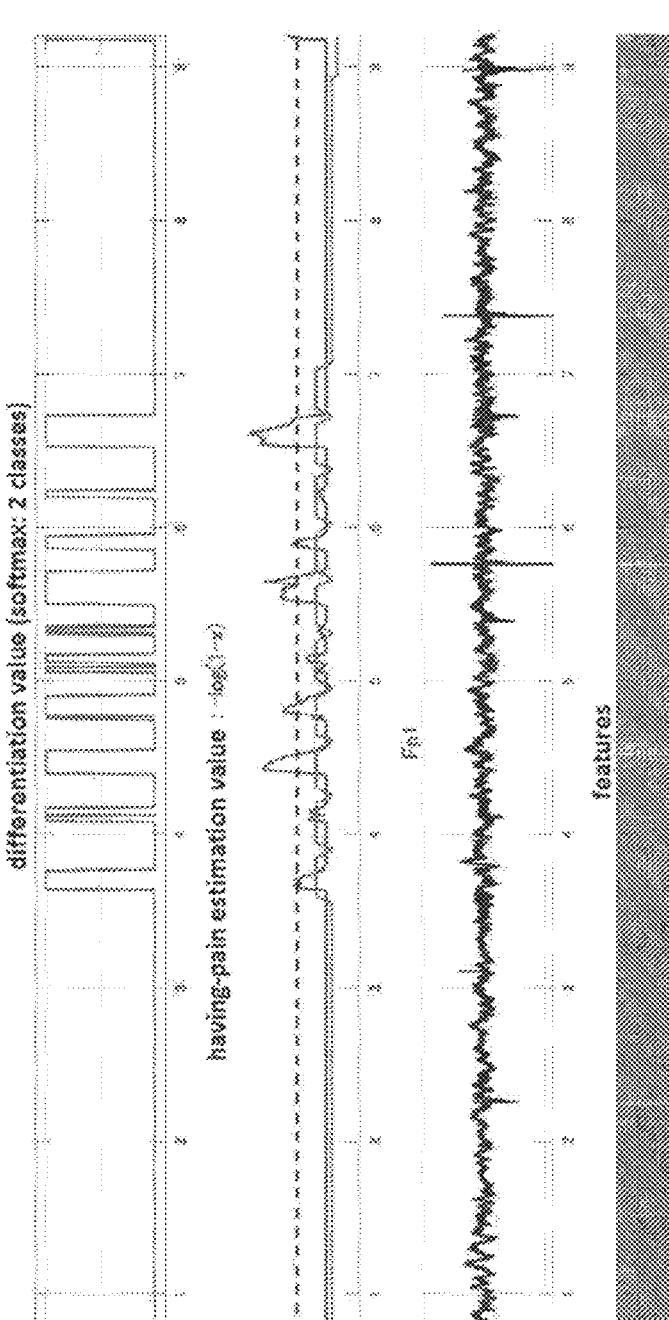
FIG. 40 shows results of performing an off-Line chronological data analysis on the raw data shown in FIG. 39. In 2 classes, (1) having pain appeared when there was a pain stimulation; thus, the differentiation was made well.

FIG. 39 shows raw data under main1 (pain stimulation, rest, eyes closed) conditions. FIG. 40 shows an off-line chronological data analysis for model creation. In 2 classes, (1) having pain appeared when there was a pain stimulation; thus, the differentiation was made well.

Figure 41:
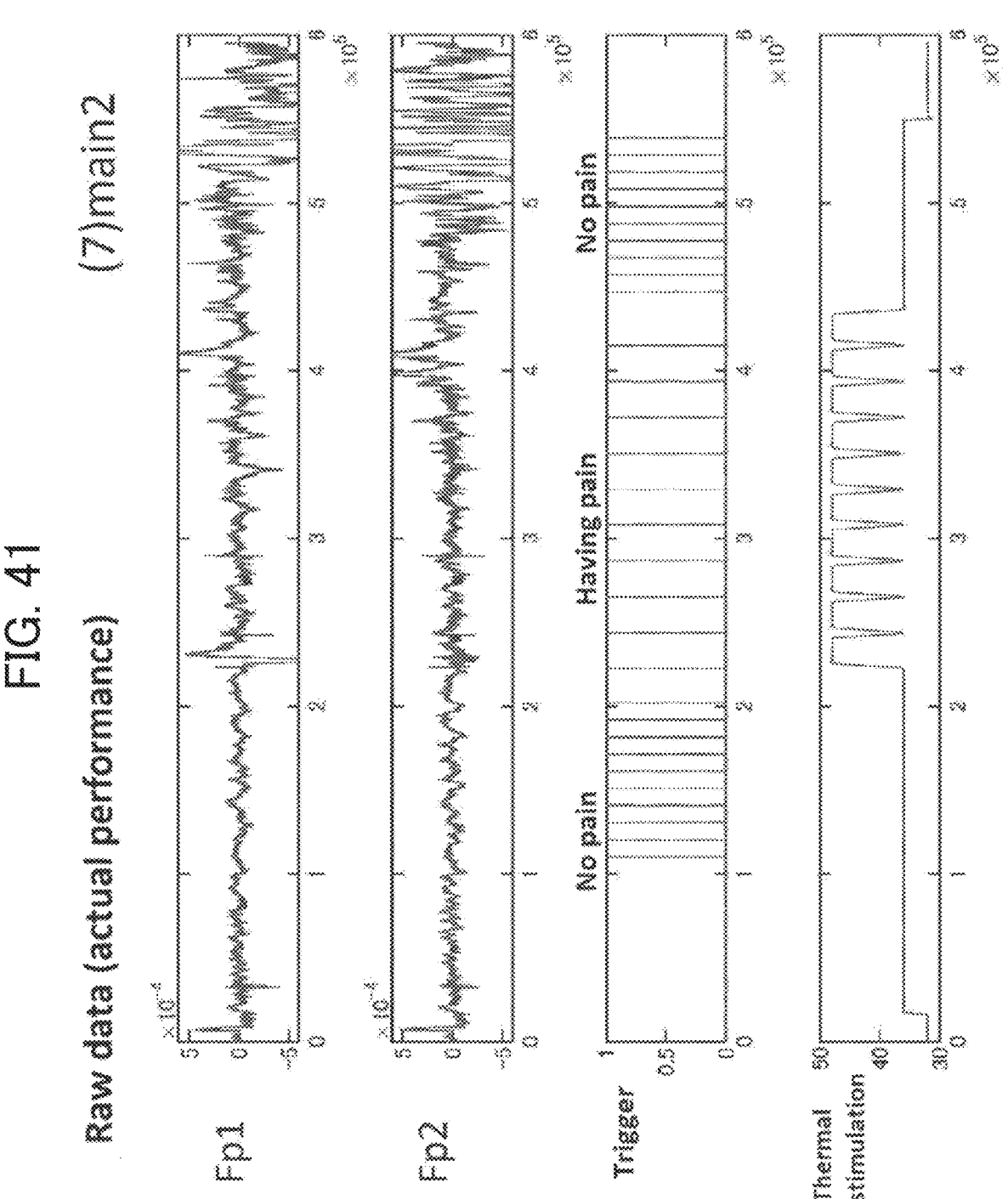
FIG. 41 shows raw data (main2) used for 2 class LSTM analysis. The conditions for main2 are pain stimulation, rest, eyes closed.
Figure 42:
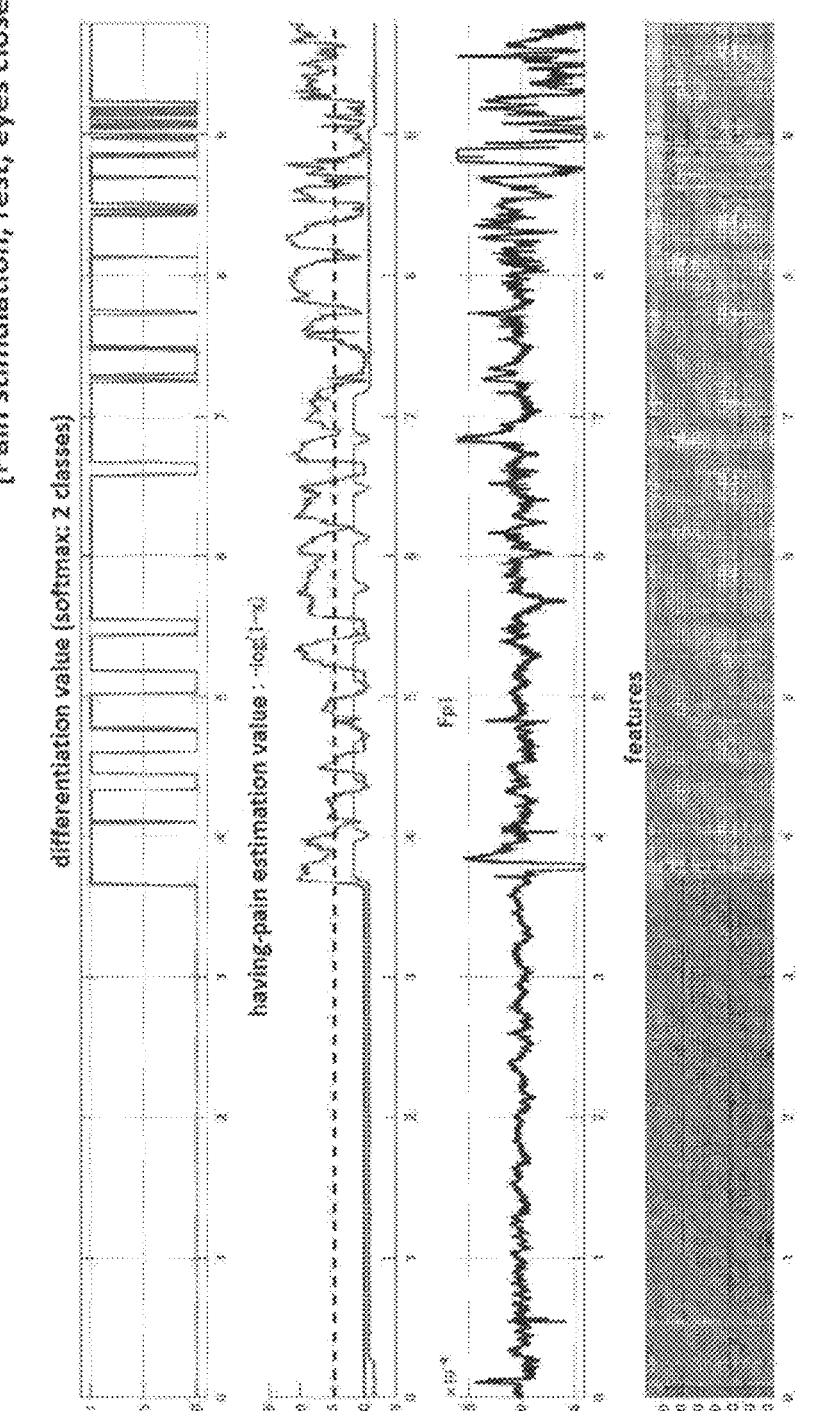
FIG. 42 shows results of performing an off-line chronological data analysis on the raw data shown in FIG. 41. Where there was no pain stimulation in the second half, it was determined as with noise (1), and the number of is-differentiation increased.

FIG. 41 shows raw data under main2 (pain stimulation, rest, eyes closed) conditions. FIG. 42 shows an off-line chronological data analysis for model creation. Where there was no pain stimulation in the second half, it was determined as with noise (1), and the number of mis-differentiation increased.

Figure 43:
FIG. 43 shows raw data (main3) used for 2 class LSTM analysis. The conditions for main3 are noise test upon pain stimulation, eyes closed.

FIG. 43 shows raw data under main3 (noise test upon pain stimulation, eyes closed) conditions. FIG. 44 shows an off-line chronological data analysis for model creation. Overall, it was determined as having pain (1), and the number of mis-differentiation increased in 2 classes.

Figure 45:
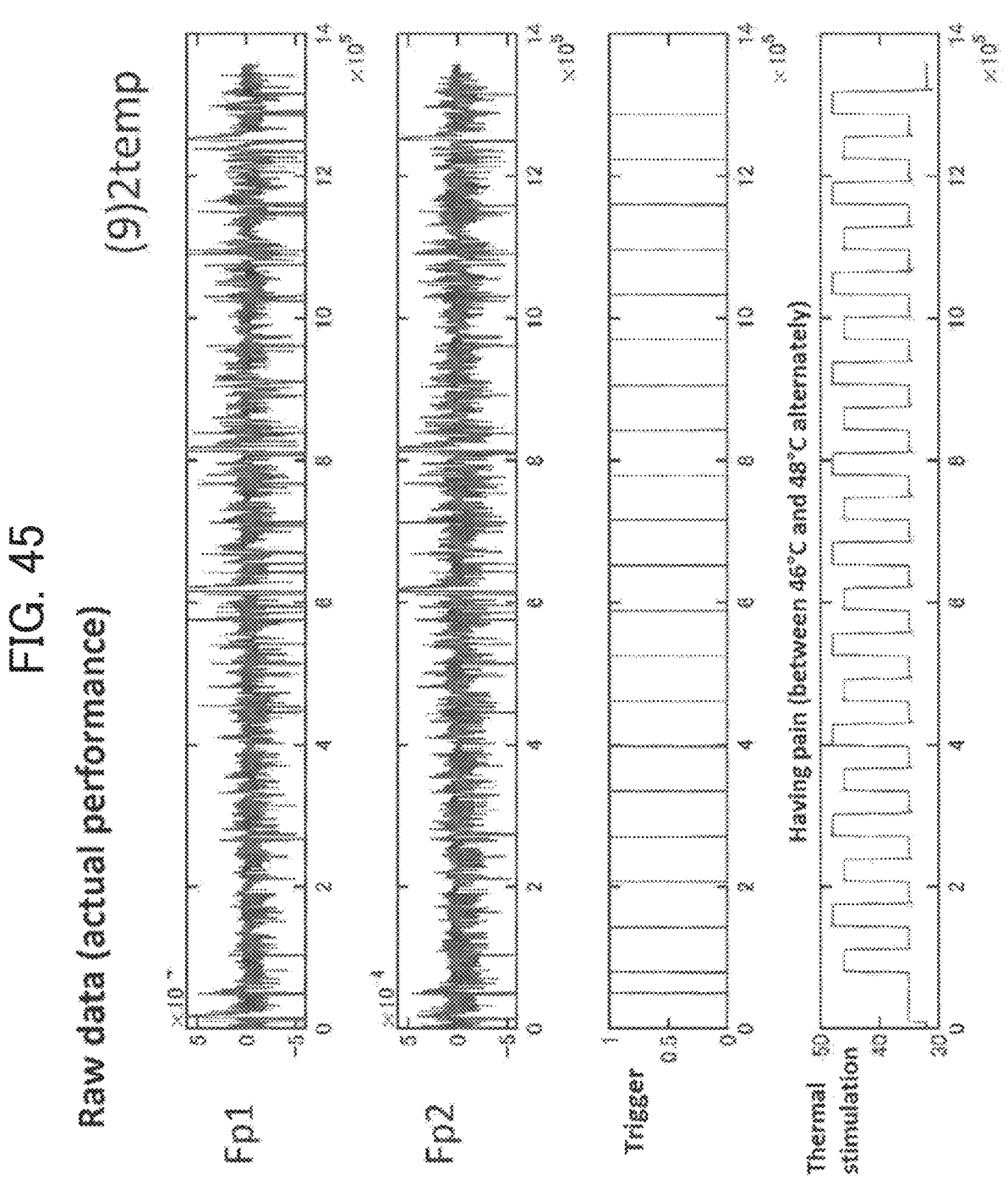
FIG. 45 shows raw data (2temp) used for 2 class LSTM analysis. The conditions for 2temp are pain stimulation (moderate: 46° C., great: 48° C.), eyes opened.
Figure 46:
FIG. 46 shows results of performing an off-line chronological data analysis on the raw data shown in FIG. 45. Overall, the number of mis-differentiation increased. It is conceivable that this was because no eye-closing task was performed.

FIG. 45 shows raw data under 2temp (pain stimulation (moderate: 46° C., great: 48° C.), eyes opened) conditions. FIG. 46 shows an off-line chronological data analysis for model creation. Overall, the number of mis-differentiation increased. It is conceivable that this was because no eye-closing task was performed.

Figure 47:
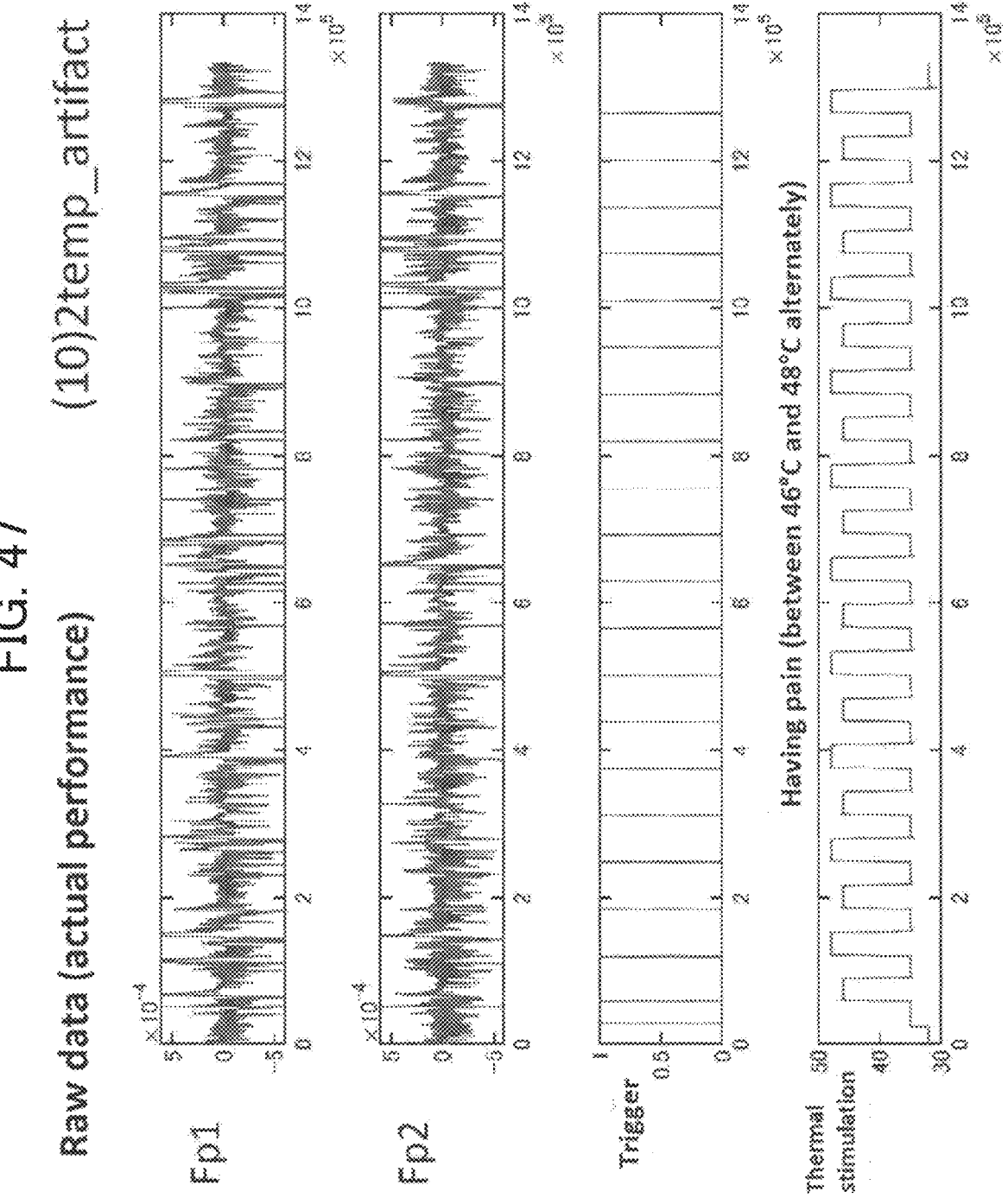
FIG. 47 shows raw data (2temp) used for 2 class LSTM analysis. The conditions for 2temp artifact are noise test upon pain stimulation (moderate: 46° C., great: 48° C.) (voluntary reaction with noise inputted), eyes opened.
Figure 48:
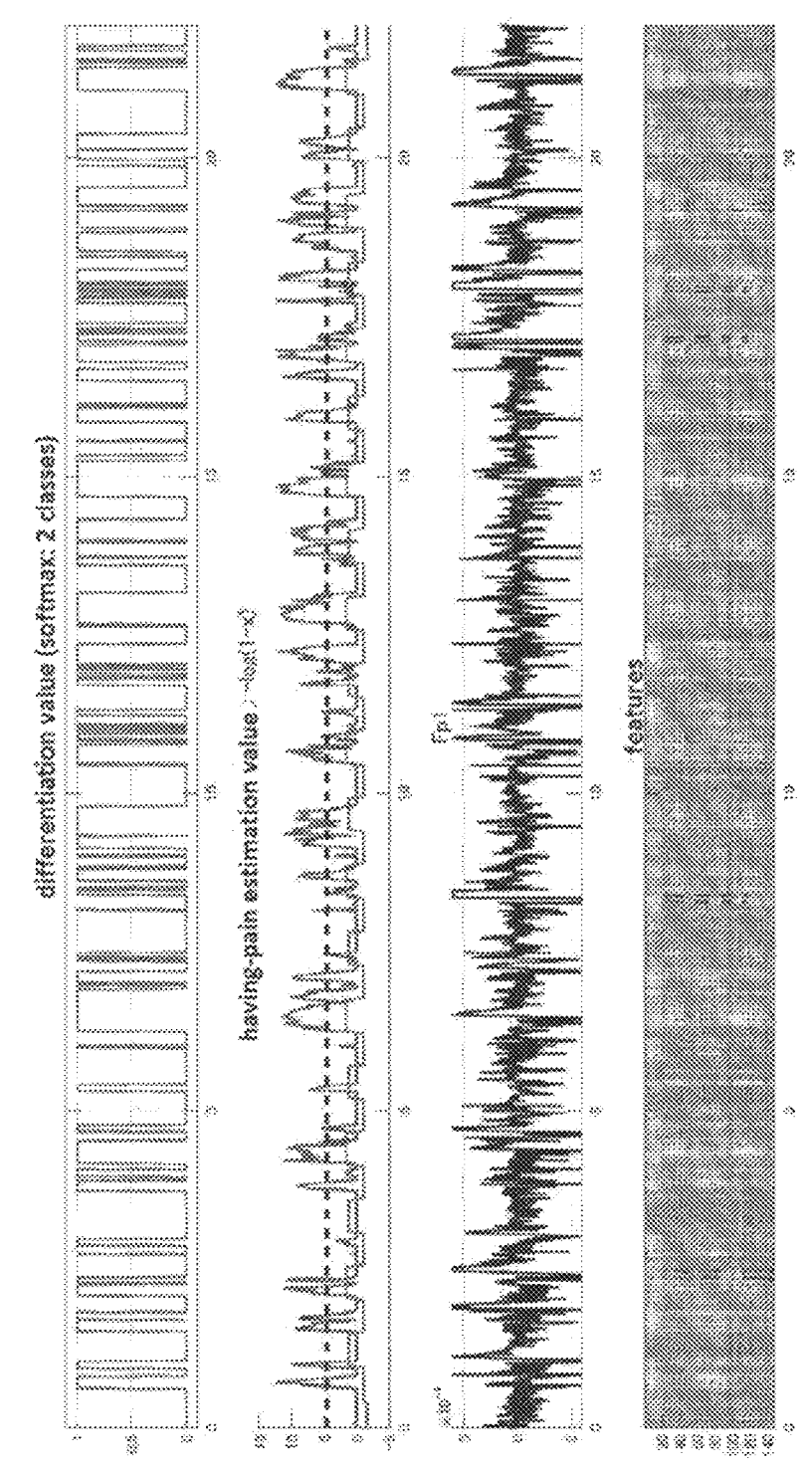
FIG. 48 shows results of performing an off-line chronological data analysis on the raw data shown in FIG. 47. Overall, the number of mis-differentiation increased. It is conceivable that this was because no eye-closing task was performed.

FIG. 47 shows raw data under 2temp_artifact (noise test upon pain stimulation (moderate: 46° C., great: 18° C.) (voluntary reaction with noise inputted), eyes opened) conditions. FIG. 48 shows an off-line chronological data analysis for model creation. Overall, the number of mis-differentiation increased. It is conceivable that this was because no eye-closing task was performed.
(Observation)

It was suggested that the differentiation accuracy of the 2 classes may decrease when the fitting is made to an individual with the use of the reference stimulation because there are fewer types of labels than in the 4 classes. Based on this fact, it was suggested, on the contrary, that the differentiation accuracy may be increased by specifically defining as many labels as possible when the reference stimulation is used.

Example 4

Pain Differentiation Using a Model Created by Pre-Examination
The experimental paradigm is as follows.
Subject (patient): F030 Age: 61 years old Gender: Female
Disease Name: varicose veins of both lower extremities
Operative Method: both lower extremity vein laser ablation
Date and Time: Nov. 17, 2018, 13:55-19:52 (5 hrs. 57 min.)

Data were collected in two parts, with pre-examination for modeling and actual performance during surgery for testing. The data for testing did not include a pain label, but the procedure during surgery was recorded and the NRS was asked to replace it.

Figure 50:
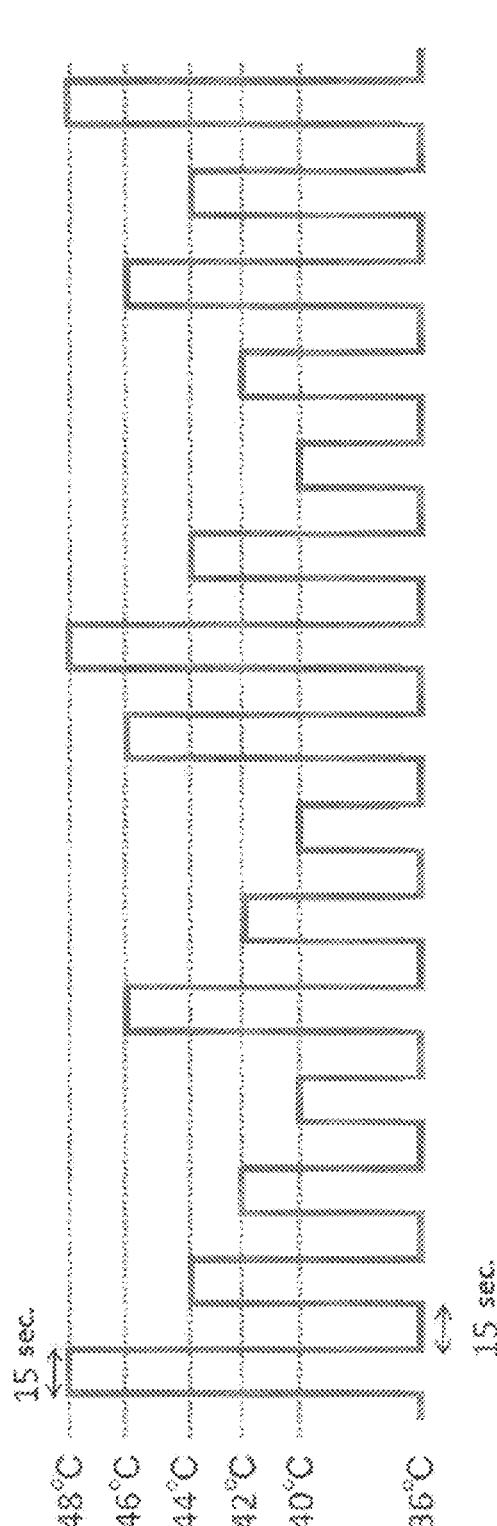
FIG. 50 shows a Pathway program with the presentation of thermal stimulation. Thermal stimulation was presented three times each in five stages from 40° C. to 48° C.

The subject was randomly presented with thermal stimulation three times each in five stages from 40° C. to 48° C. Of these, 40, 42 and 44° C. were designated as "no pain" and 48° C. as "having pain", and 2 classes were examined (FIG. 50).

Figure 51:
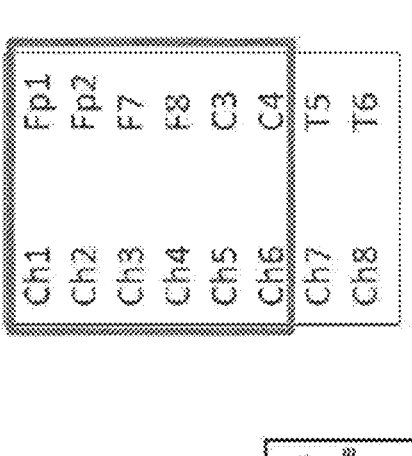
FIG. 51 shows mounting locations of brainwave electrodes. Frequency power was extracted as a feature from the absolute amplitude and 6 frequency bands (2-5 Hz, 5-8 Hz, 8-14 Hz, 14-29 Hz, 31-40 Hz, 40-49 Hz); and as pretreatment, EOG removal and bandpass filter were applied.
Figure 52:
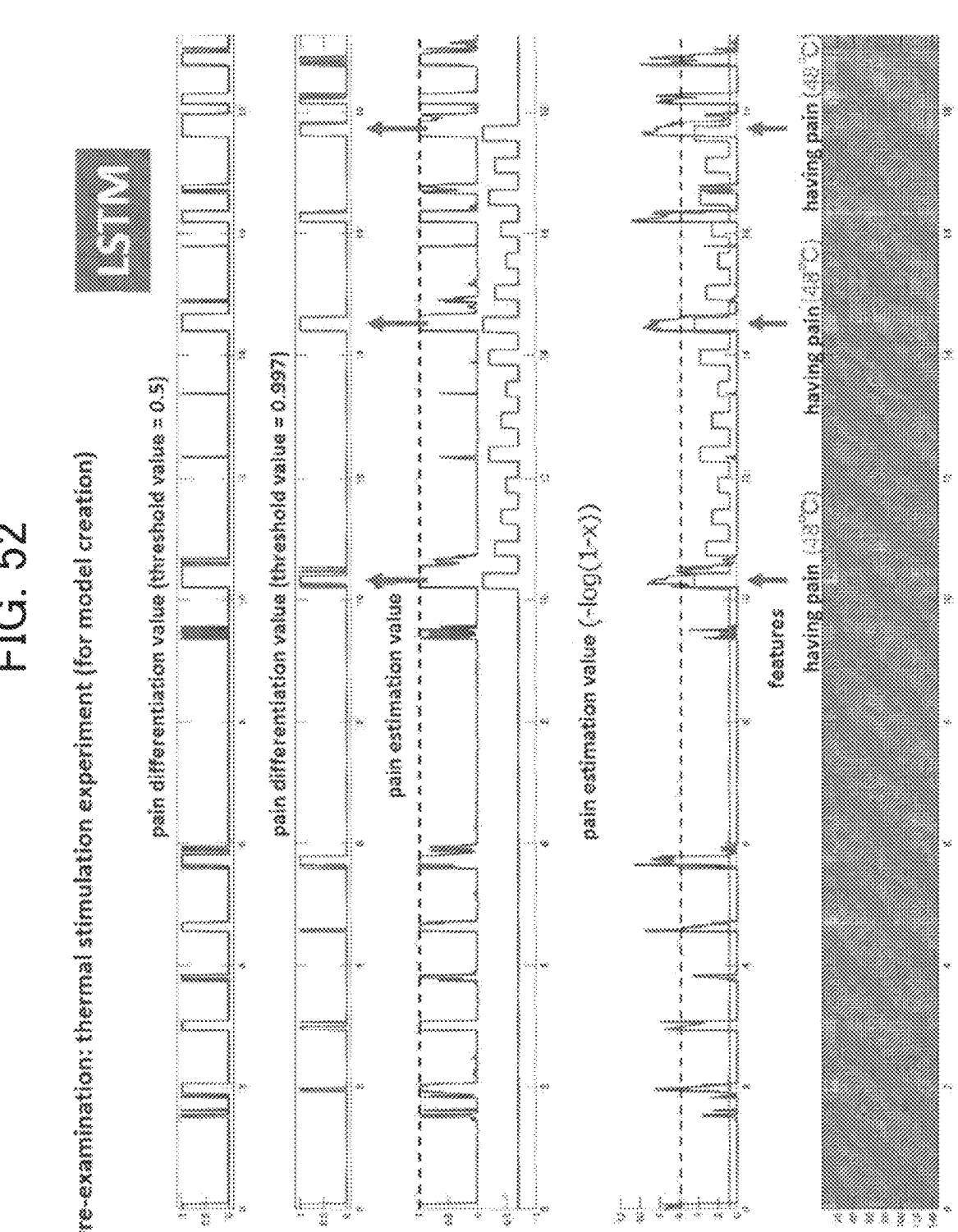
FIG. 52 shows results of thermal stimulation experiment for creating a model.
Figure 53:
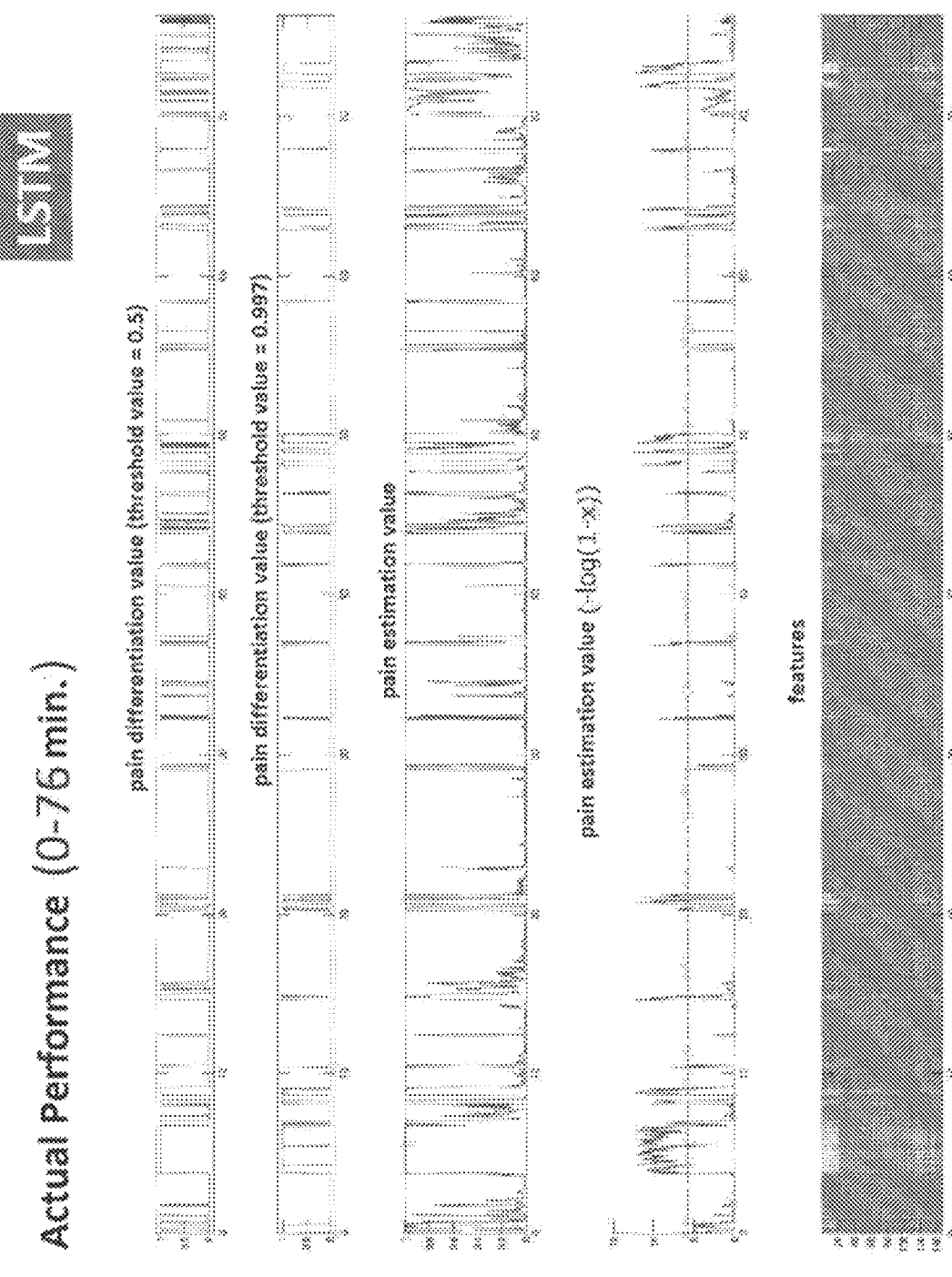
FIG. 53 shows pain differentiation values, pain estimation values and features at an actual performance (zero to 76 minutes).
Figure 54:
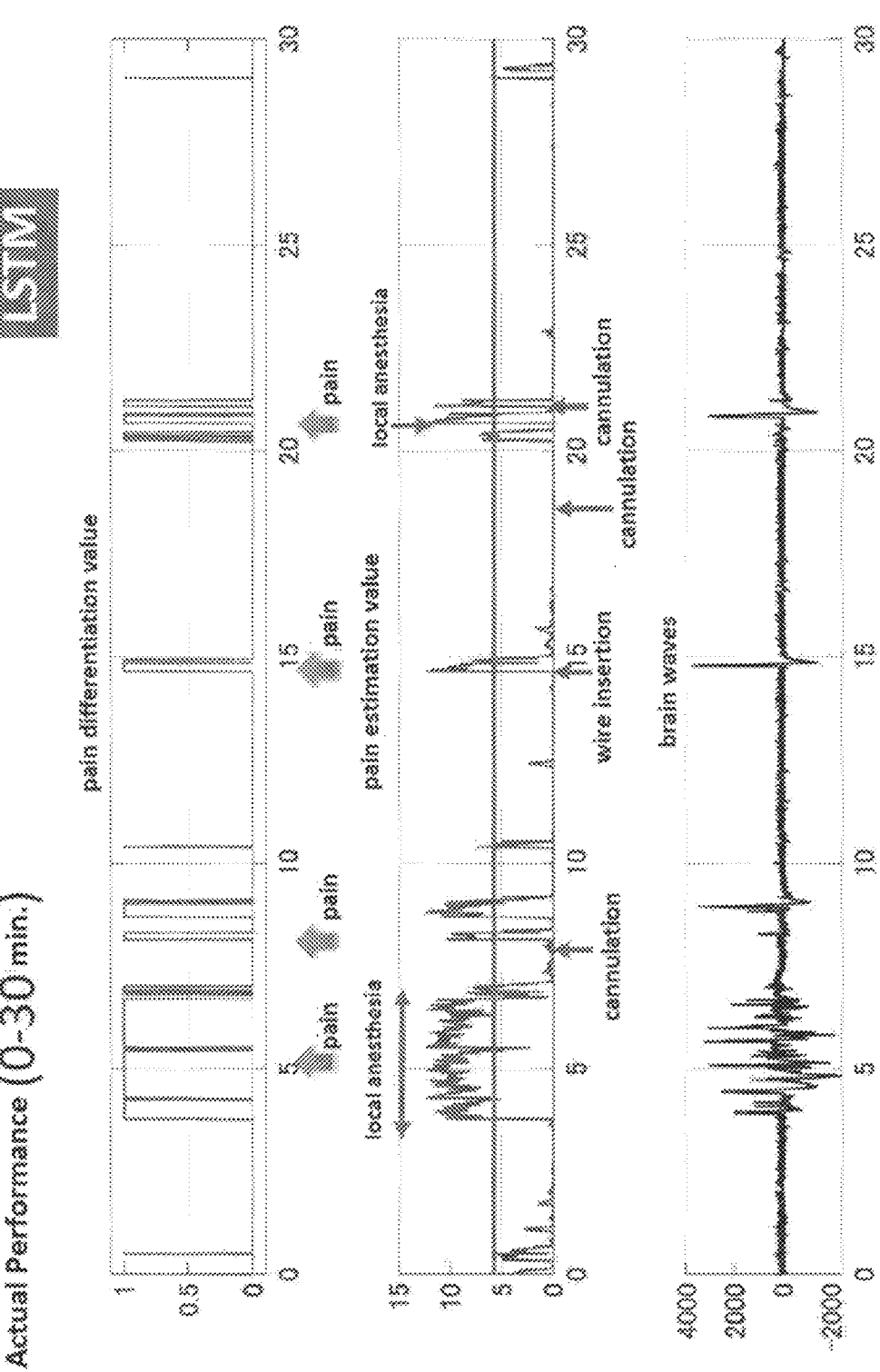
FIG. 54 shows pain differentiation values, pain estimation values and brainwaves at an actual performance (zero to 30 minutes).
Figure 55:
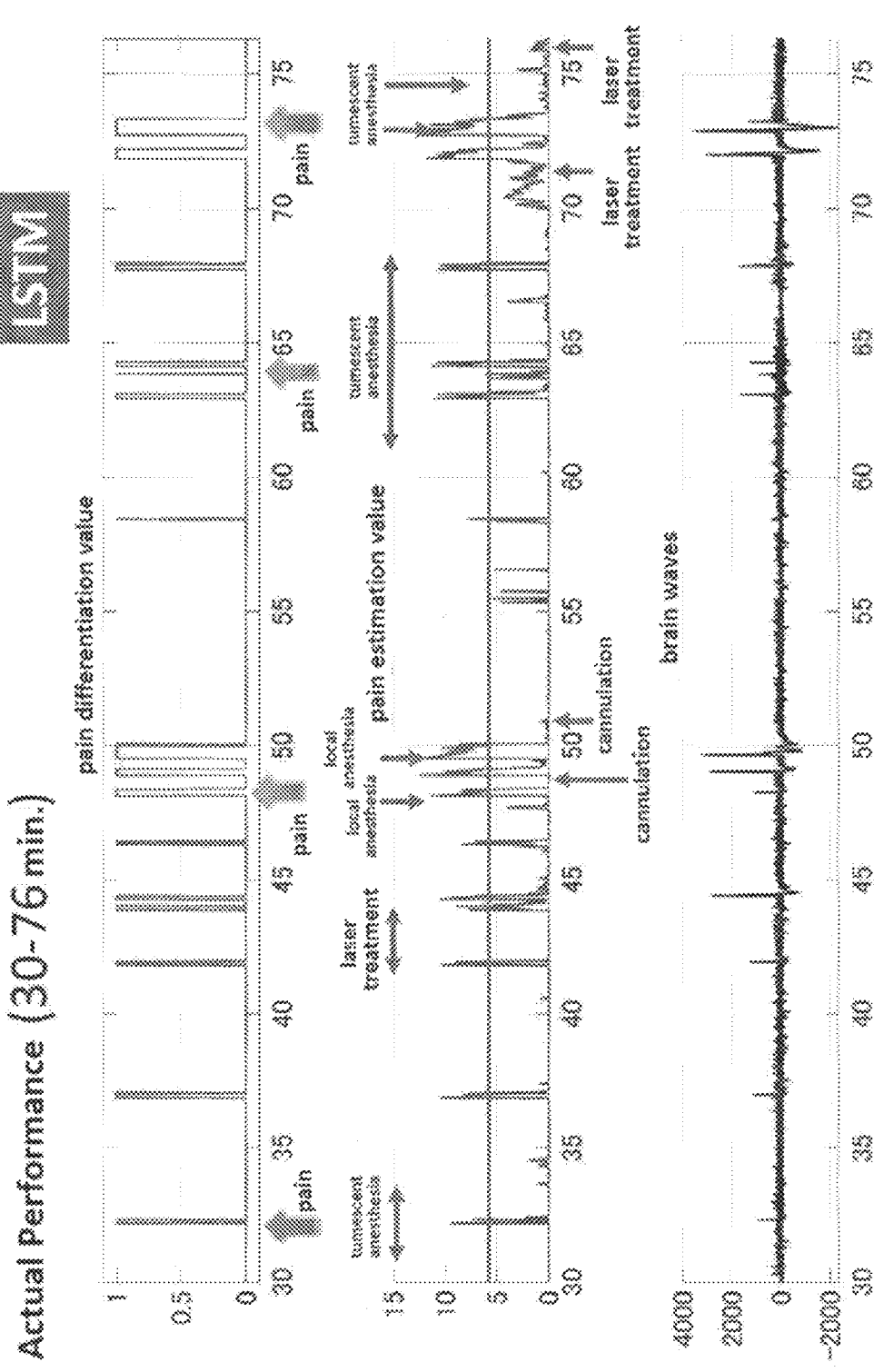
FIG. 55 shows pain differentiation values, pain estimation values and brainwaves at an actual performance (30 to 76 minutes).
Figure 56:
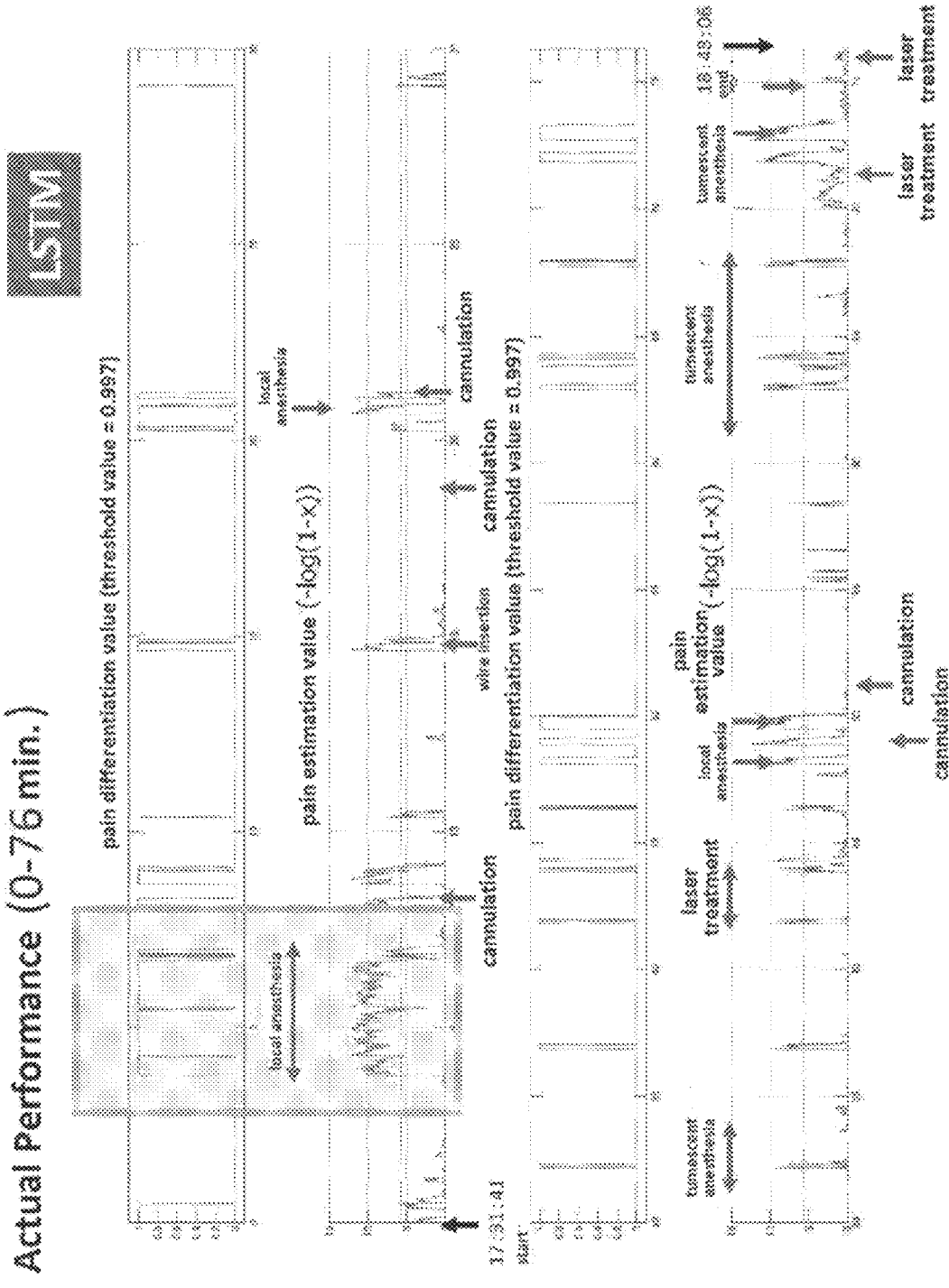
FIG. 56 shows pain differentiation values and pain estimation values at an actual performance (zero to 76 minutes).

For the brainwaves, 6 channels of the forehead were used, and frequency power was extracted as a feature from the absolute amplitude and 6 frequency bands (2-5 Hz 5-8 Hz, 8-14 Hz, 14-29 Hz, 31-40 Hz, 40-49 Hz) (FIG. 51). As retreatment, EOG removal and bandpass filter were applied.

The learning model was created by performing sample augmentation and using LSTM (Long short-term memory) for each of the two classes. Using 147×15 features, sample augmentation was performed after feature extraction and before model creation.

Two classes ("0: no pain, 1: having pain") ere differentiated against the off-line chronological data, threshold values were set individually, and the results were output as pain differentiation values.

FIGS. 52 to 56 show results of the pre-examination and the actual performance.
(Results)

When the chronological data during surgery when the patient's subjective evaluation of pain (VAS) was high (especially during local anesthesia) was evaluated using LSTM, a high degree of agreement was successfully obtained.

Example 5

Figure 57:
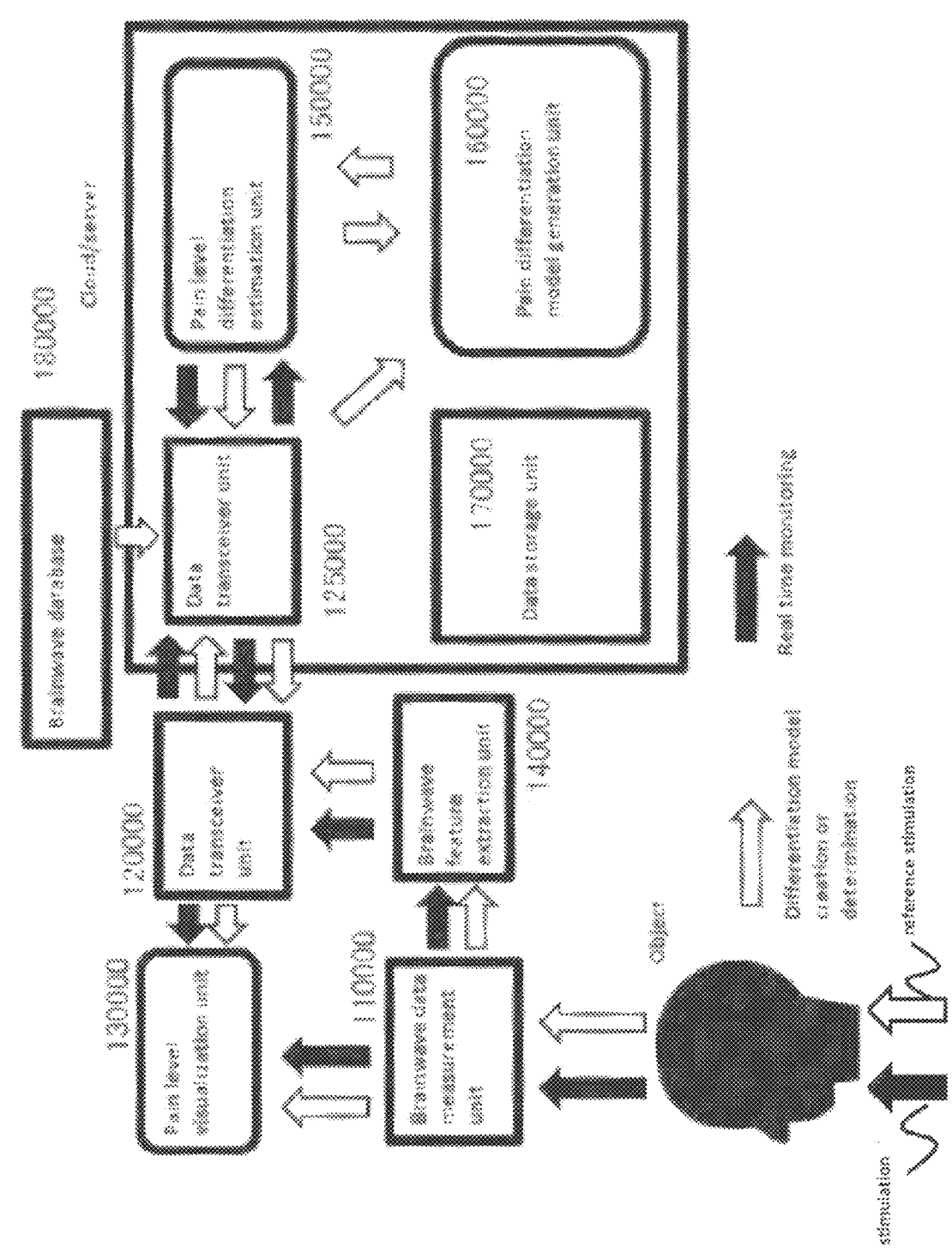
FIG. 57 shows an example of the configuration of a medical system with the reference stimulation applied therein.

Virtual Example, Medical Device to which Reference Stimulation is Applied, Medical System FIG. 57 shows an example of the configuration of a medical system with the reference stimulation applied therein, in an exemplary example. The medical system shown in FIG. 57 includes a device portion (left side) and a clou/server portion (right side). The device portion has a function to acquire brainwaves, extract features, transmit/receive data, and make them visible. For this function, the device portion comprises a brainwaves data measurement unit 110000, a data transceiver unit 120000, a pain level visualization unit 130000, and a brainwave feature extraction unit 140000. The cloud/server portion has a function to perform analysis, generation of a determination/differentiation model, and the cloud/server portion comprises a data transceiver unit 125000, a pain level differentiation estimation unit 150000, a pain differentiation model generation unit 160000, and a data storage unit 170000. The device portion and cloud/server portion may be connected to each other via the data transceiver units 120000 and 125000. The cloud/server portion may be connected with a brainwave database 180000. In this model, the extraction of the brainwave feature (analysis data) is performed in the device portion.

As shown in FIG. 57, the medical system in the present example can be used when a differentiation model is created or determined (white arrow) and when actual pain is monitored (black arrow). In creating/determining a model, reference stimulation is applied to an object. The brainwaves data measurement unit 110000 measures brainwaves of an object when the object receives a reference stimulation. The reference stimulation is applied to the object, for example, in a state in which the object is at rest (without noise) and in a state in which the object is performing a noise-generating behavior (with noise). The measured data is transmitted to the brainwave feature extraction unit 140000 to extract a plurality of features. The extracted features are transmitted to the cloud/server portion via the data transceiver unit 120000. When the cloud/server portion receives the features via the data transceiver unit 125000, the features are transmitted to the pain differentiation model generation unit 160000. The pain differentiation model generation unit 160000 generates a differentiation model based on the features. The differentiation model is such a model that allows differentiating of the presence or absence of pain. For example, when biological reaction data is input to the differentiation model, it can output whether the data is a biological reaction data with pain or a biological reaction data without pain.

Here, the generation of the differentiation model may be, for example, generation of a differentiation model by newly building a differentiation model or generation of a differentiation model by updating an existing differentiation model. Alternatively, the generation of the differentiation model may include selecting one differentiation model that best suits the brainwave features due to the reference stimulation, from among existing differentiation models.

The differentiation model is transmitted to the pain level differentiation estimation unit 150000, and the pain level differentiation estimation unit 150000 can differentiate whether the input data is a biological reaction data with pain or a biological reaction data without pain, using the differentiation model. Differentiation results by the pain level differentiation estimation unit 150000 are transmitted to the device portion via the data transceiver unit 125000. When the device portion receives differentiation results via the data transceiver unit 120000, the differentiation results are transmitted to the pain level visualization nit 130000, where the differentiation results are displayed to confirm the validity of the pain level differentiation results.

In the present example, it is also possible to generate a pain differentiation model from the features of brainwaves data stored on the brainwave database 180000, without using the reference stimulation.

Once the differentiation model is determined, real-time monitoring of actual pain levels takes place through the flow of black arrows. Specifically, once pain monitoring starts, stimulation is applied to an object, and the brainwaves data measurement unit 110000 measures the brainwaves data from the object. The measured brainwaves data is transmitted to the brainwave feature extraction unit 140000, where plurality of brainwave features are extracted. The extracted features are transmitted to the cloud/server portion via the data transceiver unit 120000. When the cloud/server portion receives the features via the data transceiver unit 125000, the features are transmitted to the pain level differentiation estimation unit 150000, where the pain level differentiation estimation unit 150000 can differentiate whether the features are those of a biological reaction data with pain or those of a biological reaction data without pain, using the differentiation model. Differentiation results by the pain level differentiation estimation unit 150000 are transmitted to the device portion via the data transceiver unit 125000. When the device portion receives the differentiation results via the data transceiver unit 120000, the differentiation results are displayed at the pain level visualization unit 130000. The processes can be combined. If differentiation results are not appropriate upon real-time monitoring, results of the pain level differentiation estimation unit 150000 are fed back to the pain differentiation model generation unit 160000. After the model is corrected, the corrected model is retransmitted to the pain level differentiation estimation unit 150000. The recorded data or created features, or the differentiation model is stored in the data storage unit 170000 when appropriate.

Figure 58:
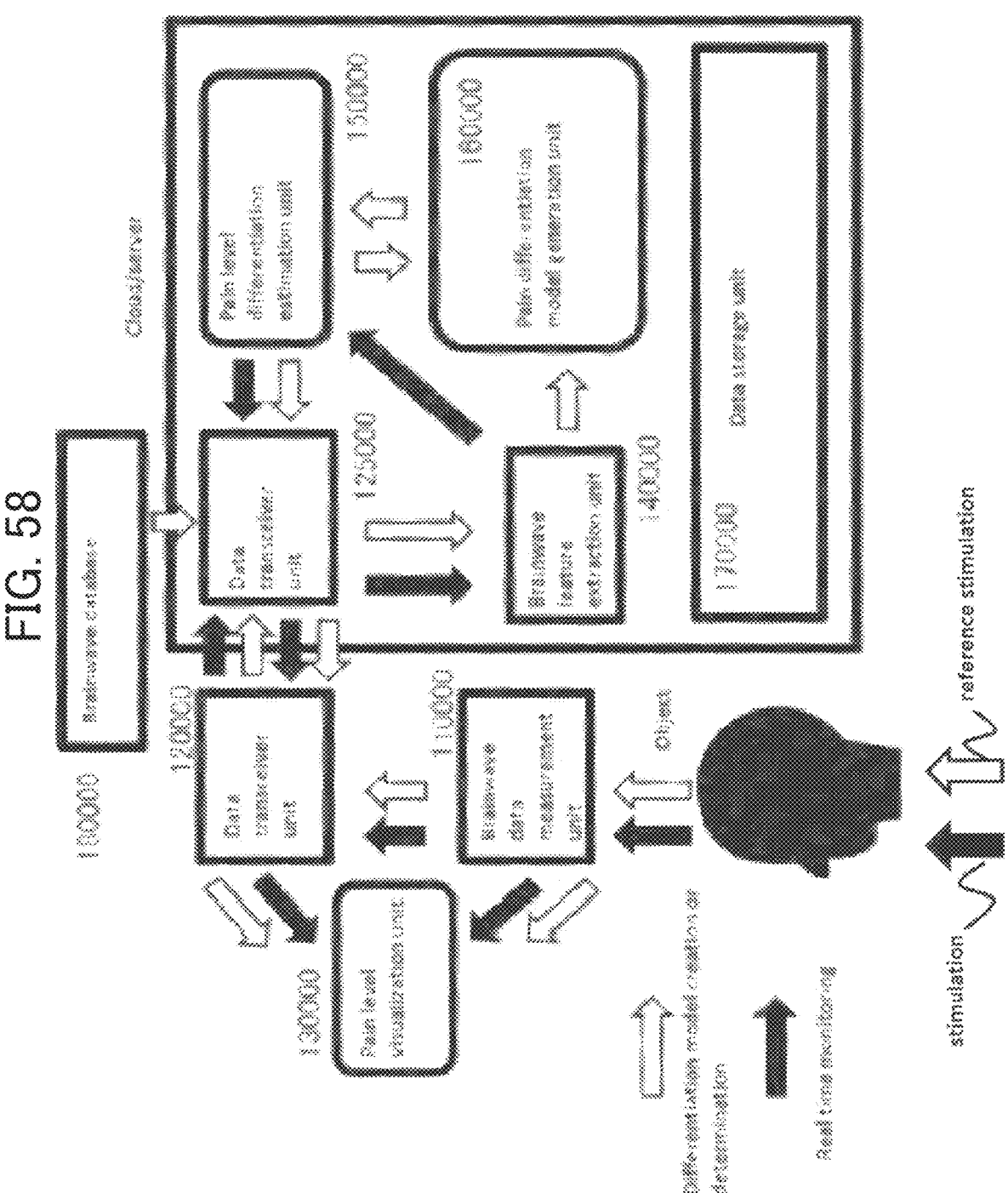
FIG. 58 shows an example of the configuration of a medical system with the reference stimulation applied therein.

FIG. 58 shows an example of the configuration of a medical system with the reference stimulation applied therein, in another exemplary example. The medical system shown in FIG. 58 includes a device portion (left side) and a cloud/server portion (right side). The medical system shown in FIG. 58 differs from the medical system shown in FIG. 57 in that the device portion does not have a function to extract features, but instead the cloud/server portion has the function to extract features. Because of this, in the medical system shown in FIG. 58, the cloud/server portion comprises a brainwave feature extraction unit 140000.

As shown in FIG. 58, the medical system according to the present example can be used when a differentiation model is created or determined (white arrow) and when actual pain is monitored (black arrow). When a model is created or determined, a reference stimulation is applied to an object. The brainwaves data measurement unit 110000 measures brainwaves of the object when the object is receiving the reference stimulation. The reference stimulation is applied to the object, for example, in a state in which the object is at rest (without noise) and in a state in which the object is performing a noise-generating behavior (with noise). The measured data is transmitted to the cloud/server portion via the data transceiver unit 120000. When the cloud/server portion receives the data via the data transceiver unit 125000, the data is transmitted to the brainwave feature extraction unit 140000, where a plurality of features are extracted. The extracted features are transmitted to the pain differentiation model generation unit 160000. The pain differentiation model generation unit 160000 gen rates a differentiation model based on the features. The differentiation model is such a model that allows differentiating of the presence or absence of pain. For example, when biological reaction data is input to the differentiation model, it can output whether the data is a biological reaction data with pain or a biological reaction data without pain.

Here, the generation of the differentiation model may be, for example, generation of a differentiation model by newly building a differentiation model or generation to a differentiation model by updating an existing differentiation model. Alternatively, the generation of the differentiation model may include selecting one differentiation model that best suits the brainwave features due to the reference stimulation, from among existing differentiation models.

The differentiation model is transmitted to the pain level differentiation estimation unit 150000, and the pain level differentiation estimation unit 150000 can differentiate whether the input data is a biological reaction data with pain or a biological reaction data without pain, using the differentiation model. Differentiation results by the pain level differentiation estimation unit 150000 are transmitted to the device portion via the data transceiver unit 125000. When the device portion receives differentiation results via the data transceiver unit 120000, the differentiation results are transmitted to the pain level visualization unit 130000, where the differentiation results are displayed Lo confirm the validity of the pain level differentiation results.

In the present example, it is also possible to generate a pain differentiation model from the features of brainwaves data stored on the brainwave database 180000, without using the reference stimulation.

Once the differentiation model is determined, real-time monitoring of actual pain levels takes place through the flow of black arrows. Specifically, once pain monitoring starts, stimulation is applied to an object, and the brainwaves data measurement unit 110000 measures the brainwaves data from the object. The measured brainwaves data is transmitted to the cloud/server portion via the data transceiver unit 120000. When the cloud/server portion receives the data via the data transceiver unit 125000, the data is transmitted to the brainwave feature extraction unit 140000, where a plurality of features are extracted. The extracted features are transmitted to the pain level differentiation estimation unit 150000, where the pain level differentiation estimation unit 150000 can differentiate whether the features are those of a biological reaction data with pain or those of a biological reaction data without pain, using the differentiation model. Differentiation results by the pain level differentiation estimation unit 150000 are transmitted to the device portion via the data transceiver unit 125000. When the device portion receives the differentiation results via the data transceiver unit 120000, the differentiation results are displayed at the pain level visualization unit 130000. The processes can be combined. If differentiation results are not appropriate upon real-time monitoring, results of the pain level differentiation estimation unit 150000 are fed back to the pain differentiation model generation unit 160000. After the model is modified, the modified model is retransmitted to the pain level differentiation estimation unit 150000. The recorded data or created features, or the differentiation model is stored in the data storage unit 170000 when appropriate.

Figure 59:
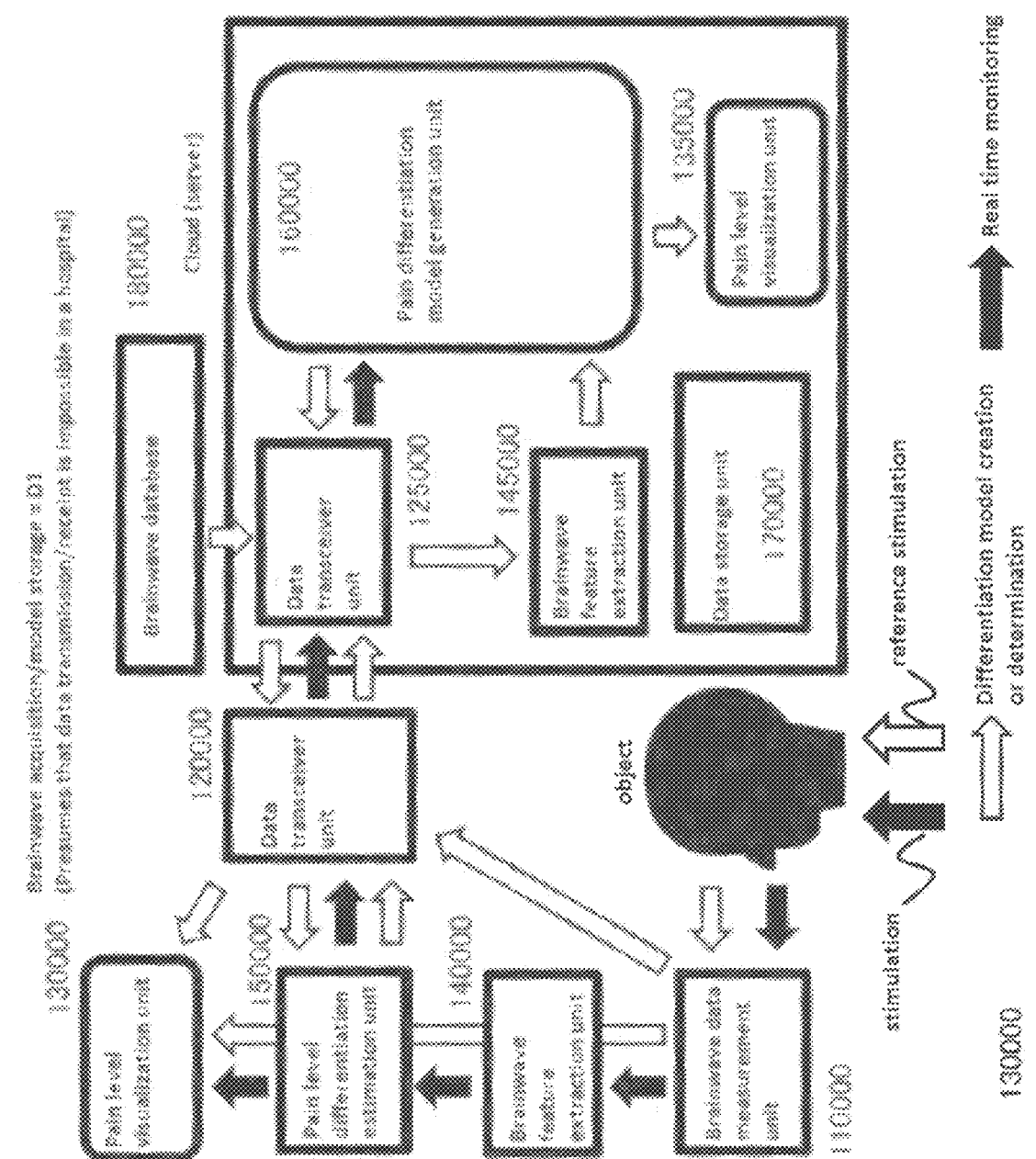
FIG. 59 shows an example of the configuration of a medical system with the reference stimulation applied therein.

FIG. 59 shows an example of the configuration of a medical system with the reference stimulation applied therein, in another exemplary example. The medical system shown in FIG. 59 includes a device portion (left side.) and a cloud/server portion (right side). The medical system shown is FIG. 59, in the device portion (left side), has a function to acquire brainwaves, transmit/receive data, enable on-site differentiation by storing a differentiation model, and make them visible. Such an embodiment presumes the embodying thereof at a facility or location where it is difficult to transmit/receive radio waves such as a hospital. Generation of a differentiation model is performed in the cloud/server portion, while actual application of the measured data to the model is performed in the device portion. The brainwave feature (analysis data) may be extracted either in the device portion or in the cloud/server portion.

In the example shown in FIG. 59, it has been explained that the differentiation model is generated in the cloud/server portion, but the present disclosure is not limited to this. It is also possible to generate the differentiation model in the device portion. That is, it is a stand-alone type.

Example 4

Augmentation of Pain Analysis Result=Closed Eye Sample Augmentation

In the present example, a closed eye sample was used to perform pain analysis. In doing so, sample augmentation was performed.
(Methods and Materials)
(Closed Eye Sample)

A closed eye sample refers to reaction data against stimulation of when the eyes of a subject are cl sed. In this example, and in the eye-closing task of having the subject close the eyes, acquired were some reaction data, or brainwaves data herein, to several gradual thermal stimulations from "no pain (36° C.)" to "having pain (48° C.)". "No pain (36° C.)" shows the state of when there is 36° C. of thermal stimulation, and "having pain (48° C.)" shows a state of when there is 48° C. of thermal stimulation.

The experimentation trial was as described below.
  (1) pre: gradual thermal stimulation (36° C. to 48° C.) reference stimulation imposed on a subject beforehand
  (2) main: after surgery (long-time (6 hours) measurement at bed side)
(Covas Template)

The above (1) of the experimentation trial was performed on a plurality of healthy people (N=150) beforehand to acquire the COVAS data of N=150. A COVAS template was prepared beforehand by calculating the mean value of the COVAS data thereof. The COVAS template corresponds the gradual thermal stimulation of (1) of the experimentation trial to the subjective evaluation of the pain of the healthy people.

Figure 62A:
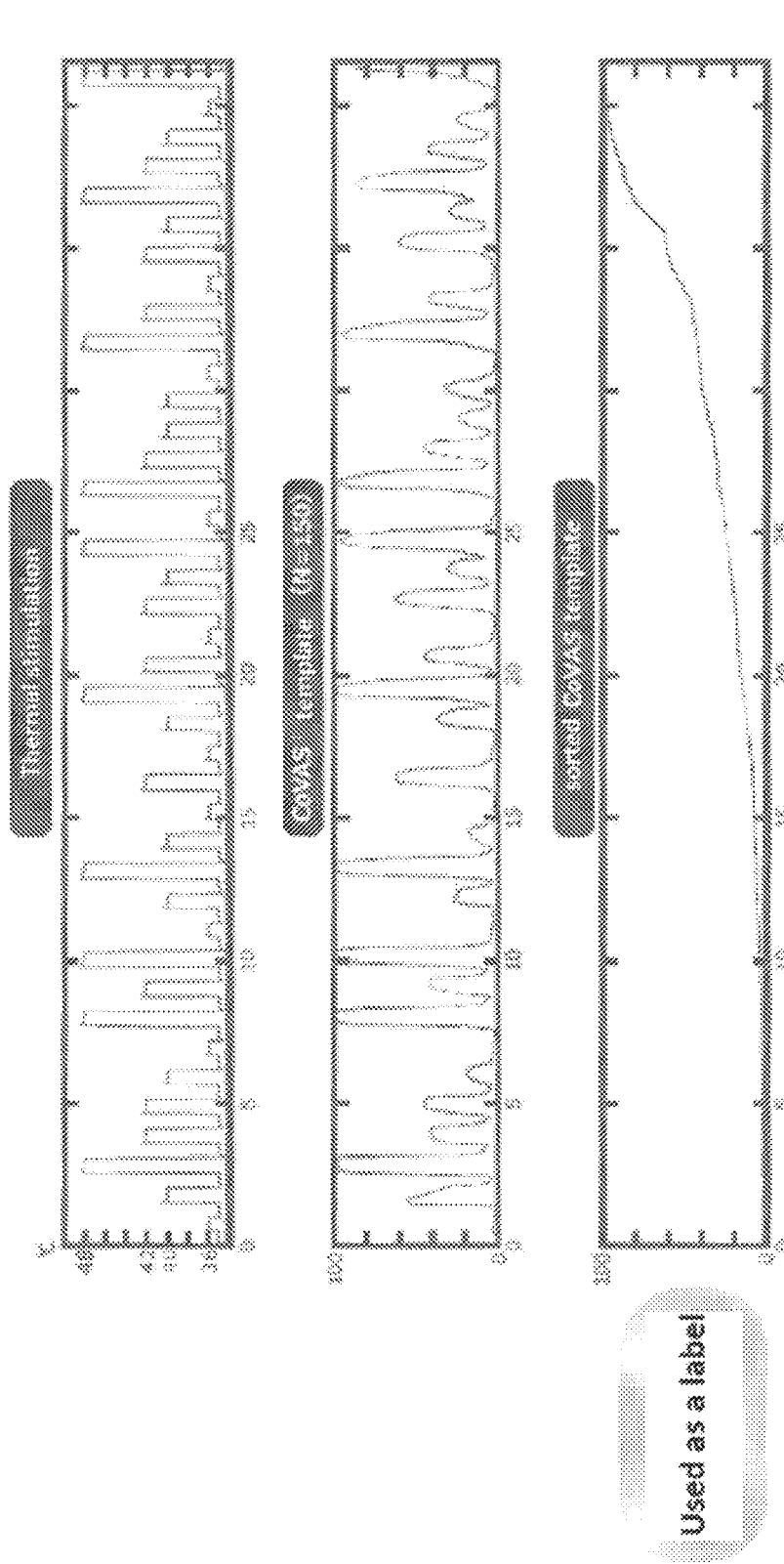
FIG. 62A shows an example of the gradual thermal stimulation of the (1) of the experimentation trial, an example of COVAS template corresponding thereto, and an example of a sorted COVAS template in which COVA templates are sorted in ascending order from the minimum value of zero to the maximum value of 100.

FIG. 62A shows an example of the gradual thermal stimulation of the (1) of the experimentation trial, an example of COVAS template corresponding thereto, and an example of a sorted COVAS template in which COVAS templates are sorted in ascending order from the minimum value of zero to the maximum value of 100.
(Preprocessing)

The sampling rate was set to 500 Hz.

The brainwave was measured by using a total of 18 ch, which are 6 ch of the forehead (monopolar electrode arrangement) added with the 6 ch of the bipolar electrode arrangement and the 6 ch of CAR (Common Average Reference) electrode arrangement.

Brainwaves data of 18 channels was cut out in the length of the COVAS template created beforehand with a trigger showing the initiation timing of thermal stimulation (pain stimulation) as the initiation point. This causes the COVAS template to match with the length of the brainwaves data of 18 channels. The COVAS template can be corresponded as a label to the brainwaves data used for learning by matching the COVAS template with the length of the brainwaves data f 18 channels. In other words, the subjective evaluation of pain would be corresponded to the brainwaves data used for learning.

The data was collected while being divided into data for model creation and data for test (actual performance) in clinical experimentation. The (1) of the experimentation trial was for model creation and the (2) of the experimentation trial was for test. The time window of 16 seconds was cut out while shifting one second at a time with respect to the entire length of the brainwaves data. The time window is shifted in the direction of the time axis to cut out a plurality of times to generate a plurality of original samples.

As a pre-processing, a dedicated noise processing method was applied to the plurality of original samples. Brainwaves data of each channel was cut out so as to secure 9 sequences while shifting an 8-second window 1 second at a time with respect to a 16-second brainwaves data of the original sample that underwent pre-processing. 4 types of features, absolute amplitude, entropy, frequency power from 8 frequency bands (2-5 Hz, 5-8 Hz, 8-14 Hz, 14-28 Hz, 28-58 Hz, 62-11 Hz, 122-178 Hz and 182-238 Hz) and coherence, were extracted from the brainwaves data of each channel. The four types of features (amplitude, frequency power, coherence and entropy) were bound and a total of 324 features were extracted. As a result, 324×9 features, with 324 feature and 9 chronological sequences determined as a unit, were acquired.

With respect to the extracted feature, a sample augmentation method was applied to each individual to increase the number of samples. The increased samples were used to create a model to be fitted to the individual using LSTM (Long short-term memory).

(Definition of Standardization Parameter for Searching a Model)

COVAS templates created beforehand were sorted in ascending order from the minimum value of zero to the maximum value of 100. From the sorted COVAS templates, 19 ranges were cut out from the minimum value, zero, to the maximum value 1000 in the unit of 10 while shifting 5 at a time. These 19 ranges were 19 types of standardization parameters, where the mean value and standard deviation of each of these 19 types of standardization parameters were calculated. For use in the off-line chronological data analysis thereafter, 19 mean values and 19 standard deviations were each preserved.

(Standardization of Feature Sata by 10 Standardization Parameters)

From the sorted COVAS templates, 10 ranges ere cut out from the minimum value of zero to the maximum value of 100 in the in the unit of 10 while shifting 10 at a time. Since these 10 ranges were 10 types of standardization parameters where the COVAS template was made to correspond to the 10 brainwaves data, features made to correspond to the 10 types of standardization parameters are extracted. The extracted features were standardized (turned into z value) using a corresponding standardization parameter.

With respect to 10 standardized features, the following steps were repeatedly performed to create 10 models (LSTM regression).

1) Regression: (Sample augmentation) Upon learning, when labels are equally present, it is understood that it is easier to acquire generalization capability, and thus, upon sample augmentation, a parameter regulating the number of augmentation samples for each label is defined so that the proportion of the values of the labels of the (sorted) COVAS templates corresponding to each feature would be equal.

2) Regression: (Sample augmentation) 5 samples are used as a unit and the samples generated by a random number from the multivariate normal distribution based on the mean value and covariance matrix thereof are increased by the parameters defined for each label in 1). The samples are increased by the number of repetition.

3) Regression: (Model creation: (learning)) The augmented sample is defined as a learning sample to be learned together with a corresponding label to create a model by LSTM regression.

Figure 62B:
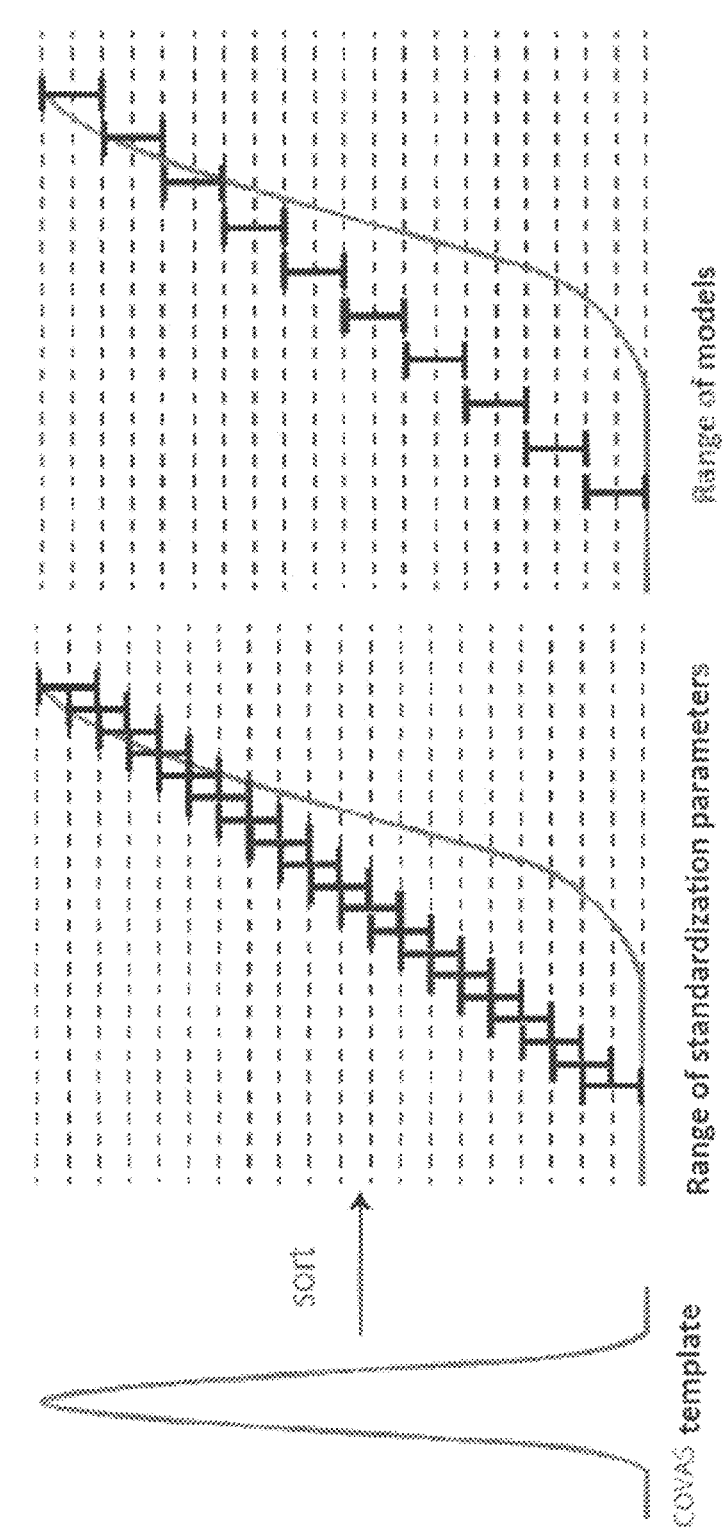
FIG. 62B shows the range of 19 types of standardization parameters cut out from the sorted COVAS templates and 10 models corresponding to 10 types of standardization parameters.

FIG. 62B shows the range of 19 types of standardization parameters cut out from the sorted COVAS templates and 10 models corresponding to 10 types of standardization parameters.

(Off-Line Chronological Data Analysis)

In order to search for the best combination from the combinations of 19 standardization parameters and 10 models, the 19 standardization parameters and 10 models were used to calculate the result of 190 regressions. In the off-line chronological data analysis, features were first extracted with respect to the entirety of the time direction of test data. The data after feature extraction was retained in an unstandardized state (unstandardized feature). With respect to the unstandardized feature, each of the 19 standardized parameters was used to perform standardization (turning into z value) to calculate the standardization feature. In other words, regarding the i-th standardization parameter among the 19 standardization parameters ($0 < i \leq 19$), when mean $\mu i$ and standard deviation $\sigma i$ are set and unstandardized feature is set as x and the standardized feature regarding the standardization parameter i is set as x'i, calculation is performed by:

$$x'i = (x - \mu i)/\sigma i$$

The pain score was predicted by administering a standardization feature to a model.

In this example, regarding 4 types of models among the 10 types of models, only the diagonal component of 10×19 matrix was used to perform ensemble learning of the pain score (prediction value of regression) and calculate the correlation function and RMSE (Root Mean Square Error), thereby displaying the result of regression.

(Results)

Figure 62C:
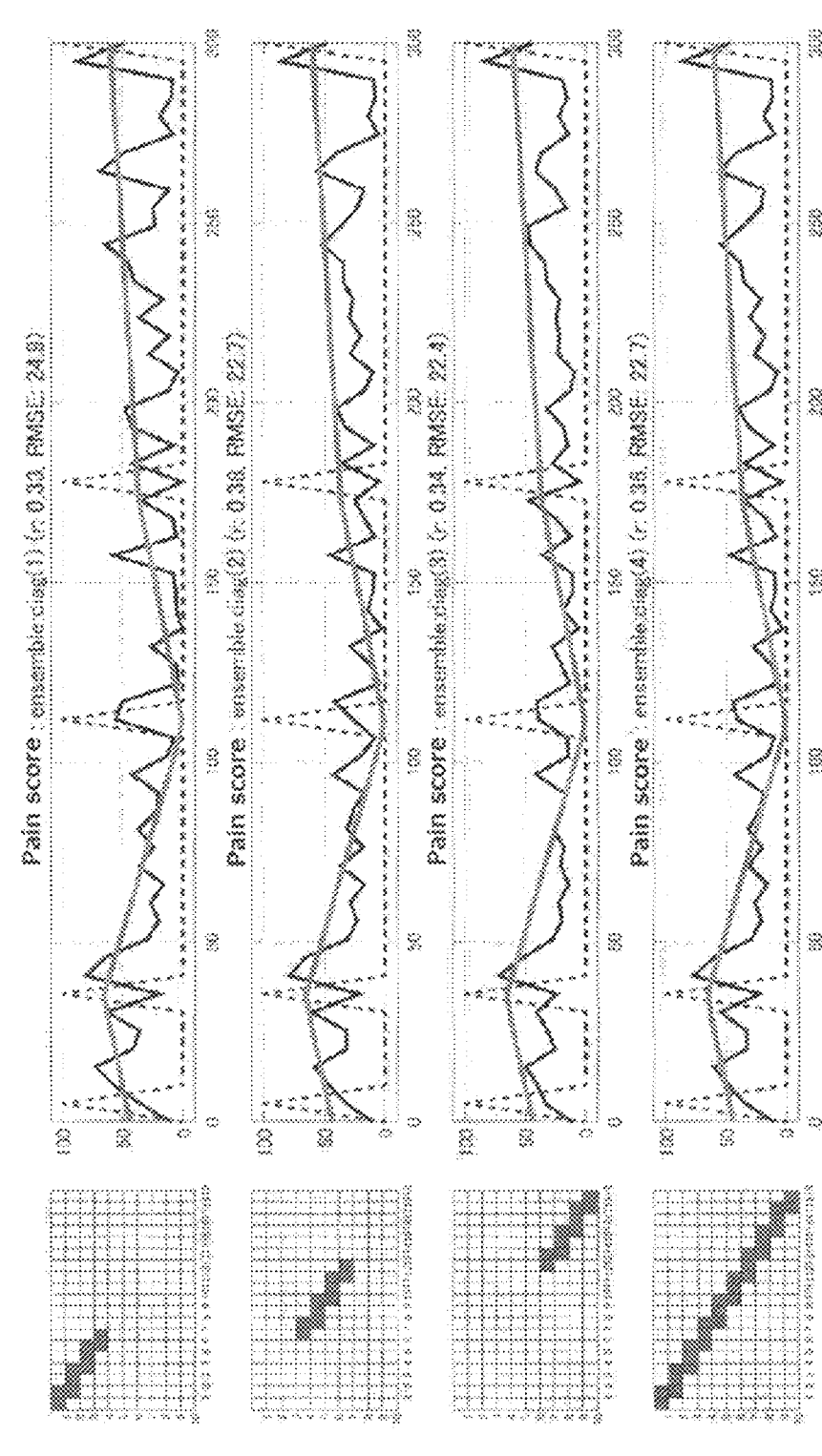
FIG. 62C shows results in Example 4.

FIG. 62C shows the result of the present example.

In FIG. 62C, the matrix on the left side expresses the combination of the used 19 standardization parameters and 10 models, where the row expresses the model and the column expresses the standardization parameter. The col red cell shows the selected combination. The ensemble learning (i.e., mean value) of what was selected corresponds to the pain score (black line) of the graph on the right side of FIG. 62C. The gray line of the graph on the right side of FIG. 62C shows NRS which is a subjective evaluation of the pain of a patient. The position of the triangle formed in a dotted line shows the timing when NRS is asked to the patient.

Among the four graphs, the first graph from the top shows the result of when using the first to fourth models and first to seventh standardization parameters, the second graph from the top shows the result of when using the fourth to seventh model and the seventh to thirteenth standardization parameters, the third graph from the top shows the result of when using the seventh to tenth models and thirteenth to nineteenth standardization parameters, and the fourth graph from the top shows the result of when using all models and standardization parameters.

It can be understood from the result of FIG. 62C that NRS corresponds to the pain score to some extent.

Example 5

Augmentation of Pain Analysis Result=Closed Eye Sample Augmentation

In the present example, a closed eye sample was used to perform pain analysis. In doing so, sample augmentation was performed.

(Methods and Materials)

(Closed Eye Sample)

A closed eye sample refers to reaction data against stimulation of when the eyes of a subject are closed. In this example, and in the eye-closing task of having t e subject close the eyes, acquired were reaction data, which is brainwaves data herein, to some gradual thermal stimulations from "no pain (36° C.)" to "having pain (48° C.)". "No pain (36° C.)" shows the state of when there is 36° C. of thermal stimulation, and "having pain (48° C.)" shows a state of when there is 48° C. of thermal stimulation.

The experimentation trial was as described below.

An experimentation (minimum_set_heat), in w ich acquiring minimum data would be enough, which was performed for algorithm development, was performed.

(1) First minimum_set_heat: gradual thermal stimulation (36° C. to 48° C.)

(2) Second minimum_set_heat: gradual thermal stimulation (36° C. to 48° C.)

In the minimum_set_heat, thermal stimulation, which the thermal stimulation was increased from 36° C. to 48° C. in a step-like manner, and the decreased from 48° C. to 36° C. in a step-like manner, was imposed.

(COVAS Template)

The (1) of the experimentation trial was performed on a plurality of healthy people (N=150) beforehand to acquire the COVAS data of N=150. A COVAS template was prepared beforehand by calculating the mean value of the COVAS data thereof. The COVAS template makes the gradual thermal stimulation of the (1) of the experimentation trial correspond to the subjective evaluation of the pain of the healthy people.

(Preprocessing)

The sampling rate was set to 1000 Hz.

The brainwave was measured by using a total of 18 ch, which are 6 ch of the forehead (monopolar electrode arrangement) added with the 6 ch of the bipolar electrode arrangement and the 6 ch of CAR (Common Average Reference) electrode arrangement.

Brainwaves data of 18 channels was cut out in the length of the COVAS template created beforehand with a trigger showing the initiation timing of thermal stimulation (pain stimulation) as the initiation point.

This causes the COVAS template to match with the length of the brainwaves data of 18 channels. The COVAS template can be made to correspond as a label to the brainwaves data used for learning, by matching the COVAS template with the length of the brainwaves data of 18 channels. In other words, the subjective evaluation of pain would be corresponded to the brainwaves data used for learning.

The data was collected while being divided into data for model creation and data for test (actual performance). The (1) of the experimentation trial is for model creation and the (2) of the experimentation trial is for test. The time window of 8 seconds was cut out while shifting one second at a time with respect to the entire length of the brainwaves data. The time window was shifted in the direction of the time axis to cut out a plurality of times to generate a plurality of original samples.

As a pre-processing, a dedicated noise processing method was applied to the plurality of original samples. Brainwaves data of each channel was cut out so as to secure 9 sequences while shifting an 8-second window 1 second at a time with respect to a 16-second brainwaves data of the original sample that underwent pre-processing. 4 types of features, absolute amplitude, entropy, frequency power from 8 frequency bands (2-5 Hz, 5-8 Hz, 8-14 Hz, 14-28 Hz, 28-58 Hz, 62-118 Hz, 122-178 Hz and 182-238 Hz) and coherence, were extracted from the brainwaves data of each channel. The four types of features (amplitude, frequency power, coherence and entropy) were bound and a total of 324 features were extracted. As a result, 324×9 features, with 324 feature and 9 chronological sequences determined as a unit, were acquired.

With respect to the extracted feature, a sample augmentation method was applied to each individual to increase the number of samples. The increased samples were used to create a model to be fitted to the individual using LSTM (Long short-term memory).

(Definition of Standardization Parameter for Searching a Model)

COVAS templates created beforehand were sorted in ascending order from the minimum value of zero to the maximum value of 100. From the sorted COVAS templates, 10 ranges were cut out from the minimum value 0 to the maximum value 1000 in the unit of 10 while shifting 10 at a time. Thes ranges were 10 types of standardization parameters, where the mean value and standard deviation of these 10 types of standardization parameters were calculated. For use in the off-line chronological data analysis thereafter, 10 mean values and 10 standard deviations were each preserved.

(Standardization of Feature Data by 10 Standardization Parameters)

From the sorted COVAS templates, 10 ranges were cut out from the minimum value of zero to the maximum value of 100 in the in the unit of 10 while shifting 10 at a time. Since these 10 ranges were 10 types of standardization parameters where the COVAS template was made to correspond to the brainwaves data, features made to correspond to the 10 types of standardization parameters are extracted. The extracted features were standardized (turned into z value) using a corresponding standardization parameter.

With respect to 10 standardized features, t e following steps were repeatedly performed to create 10 models (LSTM regression).

1) Regression: (Sample augmentation) Upon learning, when labels are equally present, it is understood that it is easier to acquire generalization capability, and thus, upon sample augmentation, a parameter regulating the number f augmentation samples for each label is defined so that the proportion of the values of the labels of the (sorted) COVAS templates corresponding to each feature would be equal.

2) Regression: (Sample augmentation) 5 samples are used as a unit and the samples generated by a random number from the multivariate normal distribution based on the mean value and covariance matrix thereof are increased by the parameters defined for each label in 1). The samples are increased by the number of repetition.

3) Regression: (Model creation: (learning)) The augmented sample is defined as a learning sample to be learned together with a corresponding label to create a model by LSTM regression.

Figure 63A:
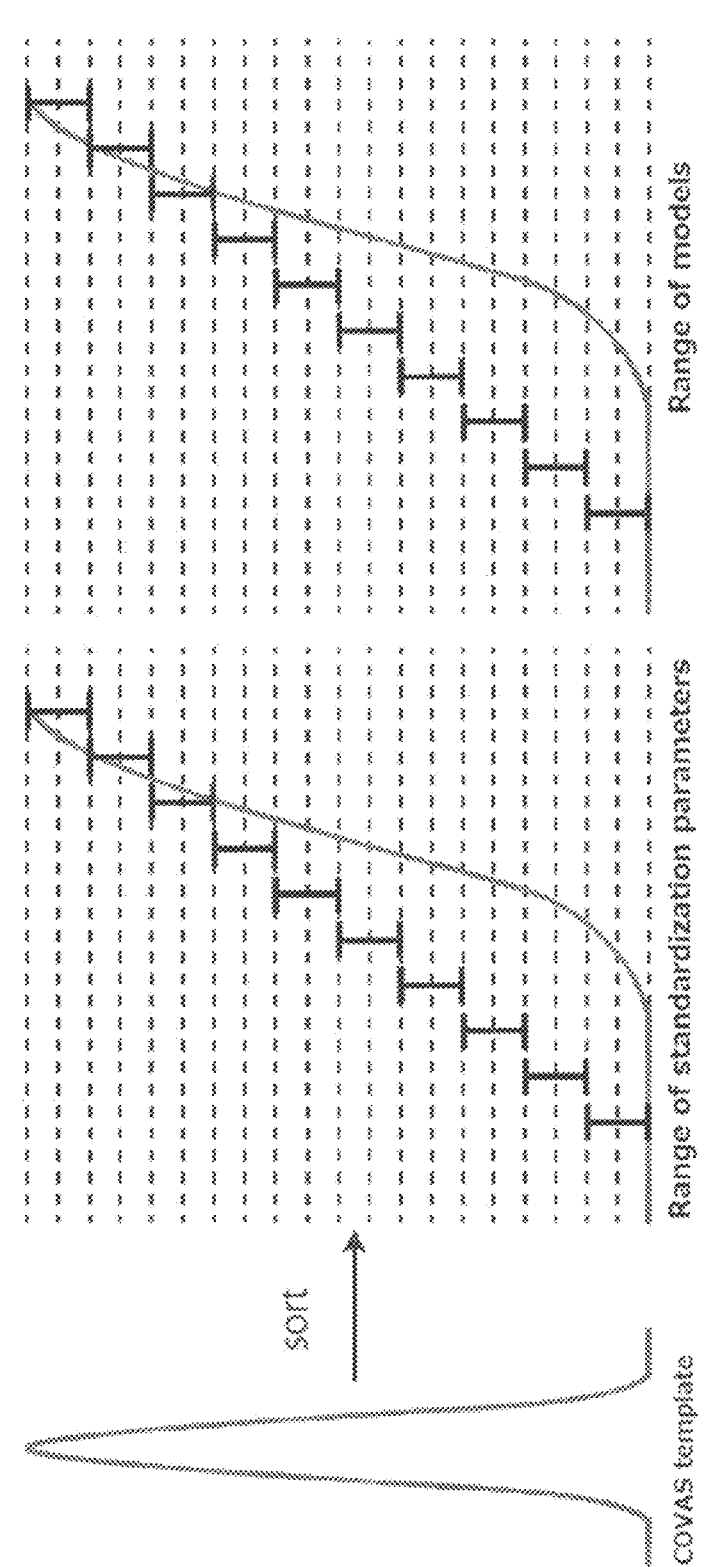
FIG. 63A shows the range of 19 types of standardization parameters cut out from the sorted COVAS templates and 10 models corresponding to 10 types of standardization parameters.

FIG. 63A shows the range of 19 types of standardization parameters cut out from the sorted COVAS templates and 10 models corresponding to 10 types of standardization parameters.

(Off-Line Chronological Data Analysis)

In order to search for the best combination from the combinations of 10 standardization parameters and 10 models, 10 standardization parameters and 10 models were used to calculate the result of 100 regressions. In the off-line chronological data analysis, features were first extracted with respect to the entirety of the time direction of test data. The data after feature extraction was retained in an unstandardized state (unstandardized feature). With respect to the unstandardized feature, each of the 10 standardized parameters was used to perform standardization (turning into z value) to calculate the standardization feature. In other words, regarding the i-th standardization parameter among the 10 standardization parameters ($0 < i \leq 10$), when mean $pi$ and standard deviation $\sigma i$ are set and unstandardized feature is set as x and the standardized feature regarding the standardization parameter i is set as x'i, calculation is performed by:

$$x'i = (x - \mu i)/\sigma i$$

The pain score was predicted by administering a standardization feature to a model.

In this example, from a 10×10 matrix, top several numbers of pieces (top 1, top 5, top 10, all) that satisfy the standard were secured beforehand based on the standard of threshold consisting of a correlation function and RMSE, where ensemble learning of pain score (prediction value of regression) was performed for each condition, and the correlation coefficient and RMSE (Root Mean Square Error) were calculated to display the result of the regression.
(Results)

Figure 63B:
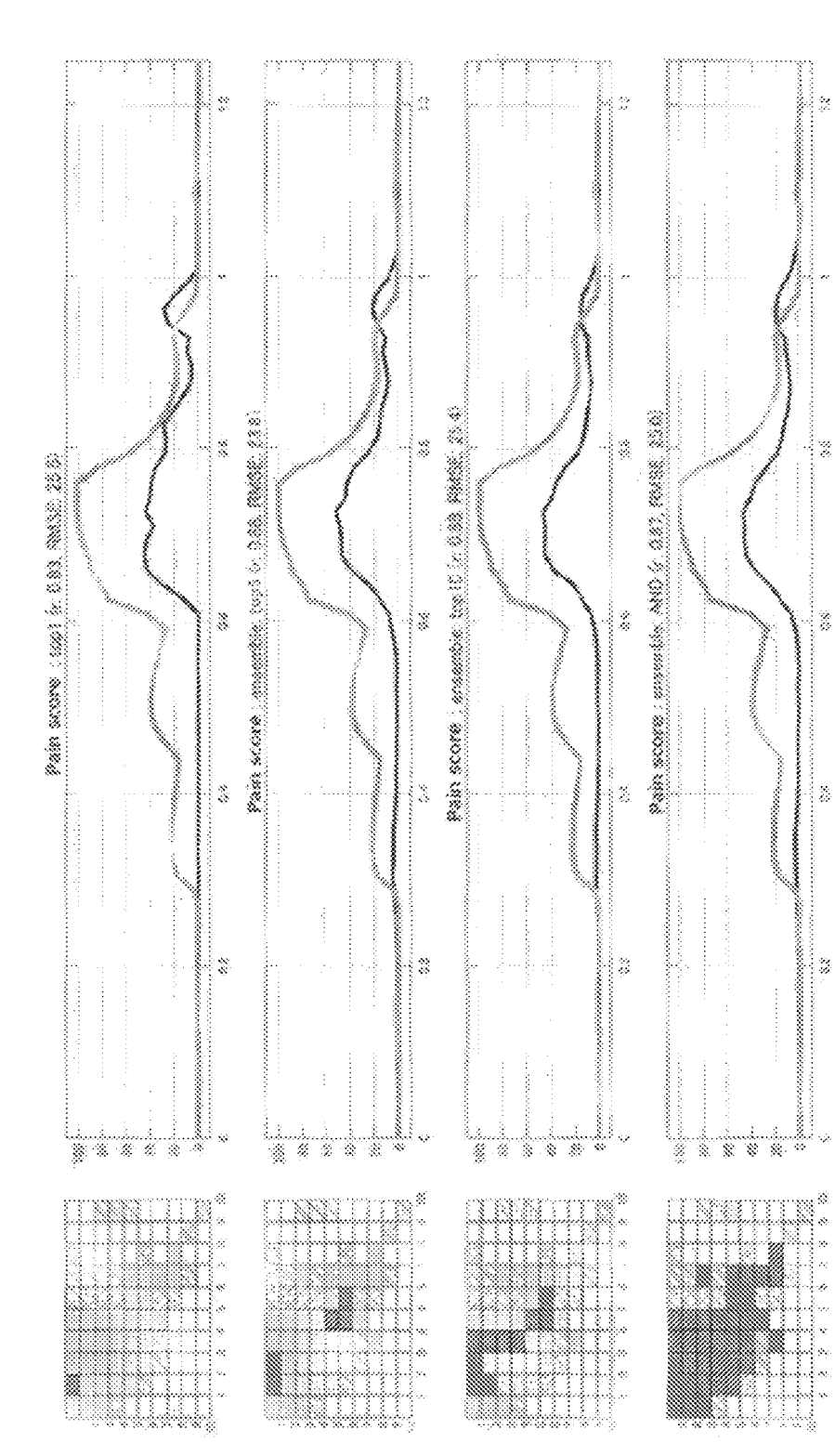
FIG. 63B shows results in Example 5.

FIG. 63B shows the result of the present example.

In FIG. 63B, the matrix on the left side expresses a combination of 10 standardization parameters and 10 models used, where the row expresses a model and the column expresses a standardization parameter. Coloring is performed based on whether or not the correlation coefficient and RMSE satisfy the threshold. The slanted lines express a combination in which RMSE is smaller than the threshold, the stipple expresses a combination in which the correlation coefficient is higher than the threshold, and the light color expresses a combination in which RMSE is smaller than the threshold and the correlation coefficient is higher than the threshold. The higher the correlation coefficient showing how well the fitting is, the better standard would be set, and the lower the RMSE showing an error, the better standard would be set. Among the light color combinations, those selecting the top 1, top 5, top 10 and all that satisfy the standard of RMSE being smaller than the threshold and the correlation coefficient being higher than the threshold are shown with the dark color, where each result is shown in the first graph, second, graph, third graph and fourth graph from the top, respectively.

The graph on the right side of FIG. 63B corresponds to the result of when the combination on the left side was used. The ensemble learning of the combinations selected with the dark color, i.e., mean value, expresses the pain score (back line: prediction value), and the gray line shows the template of COVAS (actual measurement value) which is the subjective evaluation of pain of a patient.

It can be understood from the result of FIG. 63B that the COVAS template (actual measurement value) corresponds to the pain score (prediction value) to some extent.
(Note)

As disclosed above, the present disclosure as been exemplified by the use of its preferred embodiments. However, it is understood that the scope of the present disclosure should be interpreted based solely on the Claims. It is also understood that any patent, patent application, and references cited herein should be incorporated herein by reference in the same manner as the contents are specifically described herein. The present application claims priority to Japanese Patent Application No. 2019-85779 filed on Apr. 26, 2020 with the Japan Patent Office. The entire content thereof is incorporated herein by reference.

INDUSTRIAL APPLICABILITY

The present invention is capable of differentiating physiological signals, such as pain, accurately, and enables diagnosis or therapy of pain in more detail.

The present invention can provide a method that can differentiate pain with a differentiation model sing fewer features or a model with high rate of improvement in differentiation accuracy, and can diagnose or treat pain more finely.

REFERENCE SIGNS LIST

1000: object
1100: system comprising a pain level differentiation/estimation apparatus
1110: pain level differentiation/estimation apparatus
1111: measurement unit

The invention claimed is:

1. A computer implemented method for building a machine learning model and for differentiating and diagnosing a pain level of an object during a surgery by standardizing the pain level, the computer including a memory, processor and an interface connected to an electroencephalograph, the method comprising:

acquiring, by the electroencephalograph, a plurality of brainwave data as reaction data from the object to store the brainwave data to the memory, the acquiring the plurality of brainwave data including:

acquiring a first brainwave data from the object being in a first state; and acquiring a second brainwave data from the object being in a second state; and building, by the processor, the machine learning model unique to the object for differentiating the pain level of the object on the first and the second brainwaves data, wherein the first brainwave data of the object are measured by using a stimulation application device in the first state with applying different levels of pain stimulation in a step-like manner to the object to store the first brainwave data to a storage device and the second brainwave data of the object are measured in the second state with applying no pain to the object to store the second brainwave data to the storage device and wherein the building the machine learning model includes:

I) the step of creating COVAS (computerized visual analog scale) template for standardizing the pain level, wherein the step of creating COVAS template includes:

a) the step of performing pain tests on a plurality of healthy subjects to acquire a plurality of COVAS data with applying different levels of the pain stimulation in a step-like manner to each of the healthy subjects by using the stimulation application device;

b) the step of averaging the plurality of COVAS data in each level of the pain stimulation to create COVAS templates, wherein each of the COVAS templates associates the averaged COVAS data with the corresponding level of the pain stimulation as a standardized label and includes information for showing a first trigger timing of initiation of the pain stimulation in the COVAS template; and II) the step of building the machine learning model for predicting a pain score by differentiating the pain level of the object, wherein the step of building the machine learning model includes:

c) the step of reading out the first and the second brainwave data from the storage device;

d) the step of cutting out the first and the second brainwaves data thereof based on the COVAS templates each corresponding to the level of the pain stimulation by matching the first trigger timing with a second trigger timing of initiation of the pain stimulation in the first and the second brainwaves data; and e) the step of learning the cut out brainwaves data thereof and the standardized label of the COVAS template corresponding to each of the cut out brainwaves data thereof as training data to create the machine learning model; and the method further comprising predicting, by the processor, the pain score of the object as an output of the machine learning model which receives as an input brainwave data collected from the object during the surgery.

2. The method of claim 1, wherein the step of learning the cut out brainwaves data or analysis data thereof includes:

the step of preprocessing the cut out brainwaves data by extracting feature values of absolute amplitude, entropy, frequency power from predetermined frequency bands and coherence from the brainwaves data of each brainwave measurement channel, the step of performing a sample augmentation method to increase the number of samples, and the step of creating, by using the increased samples, the machine learning model of LSTM (Long Short Term Memory) to be fitted to the object.

3. The method of claim 2, wherein the step of learning the cut out brainwaves data or analysis data thereof further includes:

the step of sorting COVAS templates in ascending order from the minimum value of zero to the maximum value, the step of cutting out, from the sorted COVAS templates, a predetermined number of ranges from the minimum value to the maximum value in a predetermined unit, the step of calculating standardization parameters for searching the machine learning model from the extracted feature values based on the mean value and the standard deviation of each of the predetermined number of ranges, and wherein the step of creating the machine learning model of LSTM includes the step of performing ensemble learning by using the standardization parameters.

4. A recording medium on which a program for building a machine learning model and for differentiating and diagnosing a pain level of an object during a surgery by standardizing the pain level, wherein when the program is executed by a computer system equipped with a processor, the program causes the processor to execute the method of claim 1.

5. A system for building a machine learning model and for differentiating and diagnosing a pain level of an object during a surgery by standardizing the pain level, comprising:

an acquisition means of acquiring, by the electroencephalograph, a plurality of brainwave data as reaction data from an object, the acquisition means including a first means for acquiring a first brainwave data from the object being in a first state and a second means for acquiring a second brainwave data from the object being in a second state; and a machine learning model building means for building a machine learning model unique to the object for differentiating a pain level of the object, based on the first and the second brainwaves data;

wherein the first brainwave data of the object are measured by using a stimulation application device in the first state with applying different levels of pain stimulation in a step-like manner to the object to store the first brainwave data to a storage device and the second brainwave data of the object are measured in the second state with applying no pain to the object to store the second brainwave data to the storage device and wherein the machine learning model building means includes:

I) a COVAS (computerized visual analog scale) template creating means for standardizing the pain level, wherein the COVAS template creating means includes:

a) means for performing pain tests on a plurality of healthy subjects to acquire a plurality of COVAS data with applying different levels of the pain stimulation in a step-like manner to each of the healthy subjects by using the stimulation application device;

b) means for averaging the plurality of COVAS data in each level of the pain stimulation to create COVAS templates, wherein each of the COVAS templates associates the averaged COVAS data with the corresponding level of the pain stimulation as a standardized label and includes information for showing a first trigger timing of initiation of the pain stimulation in the COVAS template; and II) a machine learning model building means for building the machine learning model to predict a pain score by differentiating the pain level of the object, wherein the machine learning model building means includes:

c) means for reading out the first and the second brainwave data from the storage device;

d) means for cutting out the first and the second brainwaves data thereof based on the COVAS templates each corresponding to the level of the pain stimulation by matching the first trigger timing with a second trigger timing of initiation of the pain stimulation in the first and the second brainwaves data; and e) means for learning the cut out brainwaves data thereof and the standardized label of the COVAS template corresponding to each of the cut out brainwaves data thereof as training data to create the machine learning model; and the system further comprising predicting means for predicting the pain score of the object as an output of the machine learning model which receives as an input brainwave data collected from the object during the surgery.

\* \* \* \* \*